US008674179B2

(12) United States Patent
Rozwadowski et al.

(10) Patent No.: US 8,674,179 B2
(45) **Date of Patent: *Mar. 18, 2014**

(54) MODIFYING THE DNA RECOMBINATION POTENTIAL IN EUKARYOTES

(75) Inventors: Kevin L. Rozwadowski, Saskatoon (CA); Derek J. Lydiate, Saskatoon (CA)

(73) Assignee: Her Majesty the Queen in Right of Canada, as represented by the Minister of Agriculture and Agri-Food, Saskatoon, Saskatchewan (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/114,645

(22) Filed: May 24, 2011

(65) Prior Publication Data

US 2011/0296547 A1 Dec. 1, 2011

Related U.S. Application Data

(60) Division of application No. 11/006,470, filed on Dec. 6, 2004, now Pat. No. 7,947,874, which is a continuation of application No. PCT/CA03/00821, filed on Jun. 6, 2003.

(60) Provisional application No. 60/386,901, filed on Jun. 6, 2002.

(51) Int. Cl.

| | |
|---|---|
| ***A01H 1/00*** | (2006.01) |
| ***C12N 15/82*** | (2006.01) |
| ***C12N 15/00*** | (2006.01) |
| ***C12N 15/74*** | (2006.01) |

(52) U.S. Cl.

USPC ........... 800/288; 800/278; 435/468; 435/483; 435/455

(58) Field of Classification Search

USPC ........................................................ 800/288

See application file for complete search history.

(56) References Cited

U.S. PATENT DOCUMENTS

| | | | | |
|---|---|---|---|---|
| 6,146,894 | A | 11/2000 | Nicolaides et al. | 435/440 |
| 7,947,874 | B2 | 5/2011 | Rozwadowski et al. | |
| 2002/0128460 | A1* | 9/2002 | Nicolaides et al. | 536/23.4 |
| 2004/0023388 | A1 | 2/2004 | Rozwadowski et al. | |

FOREIGN PATENT DOCUMENTS

| | | |
|---|---|---|
| WO | WO 01/61012 A1 | 8/2001 |
| WO | WO 01/62945 A1 | 8/2001 |
| WO | WO 02/22811 | 3/2002 |

OTHER PUBLICATIONS

Wu et al. 1994, J. of Bacteriology 176:5393-5400.*
Doe et al. 2000, the EMBO 19:2751-2762.*
Ainley et al., "Development of a heat shock inducible expression cassette for plants: Characterization of parameters for its use in transient expression assays," Plant Mol. Biol, 14: 949-967, (1990).
Forsburg, Susan L., "Only Connect: Linking Meiotic DNA Replication to Chromosome Dynamics," Molecular Cell, 9:4 pp. 703-711, (2002).
Lee et al., "Meiosis: how to create a specialized cell cycle," Current Opinion in Cell Biology, 13 pp. 770-777, (2001).
Böhner et al., "Transcriptional activator TGV mediates dexamethasone-inducible and tetracycline-inactivatable gene expression," The Plant Journal, 19:1, pp. 87-95, (1999).
Carrington et al., "Bipartite Signal Sequence Mediates Nuclear Translocation of the Plant Potyviral Nia Protein," The Plant Cell, 3: 953-962, (1991).
Chen et al., "The Role of the Mismatch Repair Machinery in Regulating Mitotic and Meiotic Recombination Between Diverged Sequences in Yeast," Genetics, 151: 1299-1313, (1999).
Chu et al., "The Transcriptional Program of Sporulation in Budding Yeast," Science, 282: 699-705, (1998).
Clark et al., "Functional analysis of human MutSα and MutSβ complexes in yeast," Nucleic Acids Research, vol. 27 No. 3, 736-742, (1999).
Culligan et al., "Evolutionary origin, diversification and specialization of eukaryotic MutS homolog mismatch repair proteins," Nucleic Acids Research., vol. 28 No. 2: 463-471, (2000).
Cupples et al., "A set of *lacZ* mutations in *Escherichia coli* that allow rapid detection of each of the six base substitutions," Proc. Natl. Acad. Sci. USA, 86: 5345-5349, (1989).
Datta et al., "Dual roles for DNA sequence identity and the mismatch repair system in the regulation of mitotic crossing-over in yeast," Proc. Natl. Acad. Sci. USA, 94: 9757-9762, (1997).
Dean et al., "Simplified Statistics for Small Numbers Of Observations," Anal. Chem. vol. 23, No. 4: 636-638 (1951).
Eisen, Jonathan A., "A phylogenomic study of the MutS family of proteins," Nucleic Acids Res., vol. 26 No. 18: 4291-4300, (1998).
Gari et al., "A set of vectors with a tetracycline-regulatable promoter system for modulated gene expression in *Saccharomyces cerevisiae*," Yeast, 13: 837-848, (1997).
Gatz et al., "Regulation of a modified CaMV 35S promoter by the Tn 10-encoded Tet repressor in transgenic tobacco," Mol. Gen Genet, 227: 229-237, (1991).
Gietz et al., "Studies on the Transformation of Intact Yeast Cells by the LiAc/SS-DNA/PEG Procedure," Yeast, 11: 355-360, (1995).
Gietz et al., "New yeast—*Escherichia coli* shuttle vectors constructed with in vitro mutagenized yeast genes lacking six-base pair restriction sites," Gene, 74: 527-534, (1988).
Goldfarb et al., "Synthetic peptides as nuclear localization signals," Nature, 322: 641-644, (1986).

(Continued)

*Primary Examiner* — Li Zheng

(74) *Attorney, Agent, or Firm* — Heslin Rothenberg Farley & Mesiti P.C.

(57) ABSTRACT

The present invention provides methods of modifying in vivo mutagenesis or homologous and homeologous recombination in a eukaryote. The method of modifying in vivo mutagenesis involves transforming a eukaryote with a nucleotide sequence capable of expressing a wild-type prokaryotic MutS, MutL, MutH, MutU, NLS-MutS, NLS-MutL, NLS-MutH, NLS-MutU protein, or a combination thereof, and expressing the protein. A method of modifying recombination between homologous chromosomes in an allopolyploid eukaryotic organism comprising, expressing a nucleotide sequence encoding prokaryotic NLS-MutS in combination with one or more than one of NLS-MutL, NLS-MutH, or NLS-MutU, within a germ cell of the allopolyploid eukaryotic organism is also disclosed.

15 Claims, 7 Drawing Sheets

(56) References Cited

OTHER PUBLICATIONS

Guyer et al., "Activation of Latent Transgenes in *Arabidopsis* Using a Hybrid Transcription Factor," Genetics, 149: 633-639, (1998).
Harfe, et al., "DNA Mismatch Repair and Genetic Instability," Annu. Rev. Genet., 34: 359-399, (2000).
Hopp et al., "A short polypeptide marker sequence useful for recombinant protein identification and purification," Bio/technology, 6: 1204-1210, (1998).
Joshi et al., "ATP-hydrolysis-dependent conformational switch modulates the stability of MutS-mismatch complexes," Nucleic Acids Res., vol. 28, No. 4: 853-861, (2000).
Kalderon et al., "A Short Amino Acid Sequence Able to Specify Nuclear Location," Cell, 39: 499-509, (1984).
Kleiner et al., "Construction of Multicopy Expression Vector for Regulated Overproduction of Porteins in *Klebsiella pneumoniae* and Other Enteric Bacterial," Journal of Gen Microbiol., 134: 1779-1784, (1988).
Klimyuk et al., "AtDMC1, the *Arabidopsis* homologue of the yeast DMC1 gene: characterization, transposon-induced allelic variation and meiosis-associated expression," The Plant J., 11(1): 1-14, (1997).
Kobayashi et al., "Characterization of cDNAs Induced in Meiotic Prophase in Lily Microsporocytes," DNA Res., 1: 15-26, (1994).
Labow et al., "Conversion of the *lac* Repressor into an Allosterically Regulated Transcriptional Activator for Mammalian Cells," Mol. Cell. Biol., vol. 10, No. 7: 3343-3356, (1990).
Lea et al., "The distribution of the numbers of mutant in bacterial populations," J. Genet., 49: 264-285, (1948).
Marra et al., "Recognition of DNA alterations by the mismatch repair system," Biochem. J., 338: 1-13, (1999).
Marsischky et al., "Redundancy of *Saccharomyces cerevisiae MSH3* and *MSH6* in *MSH2*-dependent mismatch repair," Genes Development, 10: 407-420, (1996).
Martinez et al., "Ecdysone agonist inducible transcription in transgenic tobacco plants," The Plant J., vol. 19, No. 1: 97-106, (1999).
Mett et al., "Copper-controllable gene expression system for whole plants," Proc. Natl. Acad. Sci. USA, 90: 4567-4571, (1993).
Mett et al., "A system for tissue-specific copper-controllable gene expression in transgenic plants: nodule-specific antisense of aspirate aminotransferase-$P_2$" Transgenic Res., 5: 105-113, (1996).
Moore et al., "A transcription activation system for regulated gene expression in transgenic plants," Proc. Natl. Acad. Sci., 95: 376-381, (1998).
Murray et al., "Condon usage in plant genes," Nucleic Acids Res., vol. 17, No. 2: 477-498, (1989).
Negritto et al., "Influence of DNA Sequence Identity on Efficiency of Targeted Gene Replacement," Mol Cell Biol, 17: 278-286, (1997).
Nelson et al., "Context Affects Nuclear Protein Localization in *Saccharomyces cerevisiae*," Mol Cell Biol, 9: 384-389, (1989).
Parkin et al., "Identification of the A and C genomes of amphidiploid *Brassica napus* (oilseed rape)," Genome, 38: 1122-1131, (1995).
Relić et al., "Interaction of the DNA modifying proteins VirD1 and VirD2 of *Agrobacterium tumefaciens*: Analyis of subcellular localization in mammalian cells," Proc. Natl. Acad. Sci. USA, 95: 9105-9110, (1998).
Robbins et al., "Two Interdependent Basic Domains in Nucleoplasmin Nuclear Targeting Sequence: Identification of a Class of Bipartite Nuclear Targeting Sequence," Cell, 64: 615-623, (1991).
Ross-Macdonald et al., "Mutation of a Meosis-Specific MutS Homolog Decreases Crossing Over but Not Mismatch Correction," Cell, 79: 1069-1080, (1994).
Russell et al., "Construction and analysis of in vivo activity of *E. coli* promoter hybrids and promoter mutants that after the −35 to −10 spacing," Gene, 20: 231-243, (1982).
S.L. Forsburg, "Only Connect: Linking Meiotic DNA Replication to Chromosome Dynamics," Molecular Cell., 9: 703-711, (2002).
Sardana, et al., "Construction and rapid testing of synthetic and modified toxin gene sequences *Cry*IA (*b* & *c*) by expression in maize endosperm culture," Plant Cell Rep., 15: 677-681, (1996).
Schneider et al., "Vectors for Expression of Cloned Genes in Yeast: Regulation, Overproduction, and Underproduction," Methods in Enzymol., 194: 373-388, (1991).
Schofield et al., "Interaction of *Escherichia coli* MutS and MutL at a DNA Mismatch," The J. of Biol. Chem., 276: 28291-28299, (2001).
Selva et al., "Differential effects of the mismatch repair genes *MSH2* and *MSH3* on homeologous recombination in *Saccharomyces cerevisiae*," Mol. Gen Genet., 257: 71-82, (1997).
Tinland et al., "The T-DNA-linked VirD2 protein contains two distinct functional nuclear localization signals," Proc. Natl. Acad. Sci. USA, 89: 7442-7446, (1992).
Toft et al., "*Msh2* status modulates both apoptosis and mutation frequency in the murine small intestine," Proc. Natl. Acad. Sci. USA, 96: 3911-3915, (1999).
Van der Krol, et al., "The Basic Domain of Plant B-ZIP Proteins Facilitates Import of a Reporter Protein into Plant Nuclei," The Plant Cell, 4: 667-675, (1991).
Varagona et al., "Nuclear Localization Signal(s) required for Nuclear Targeting of the Maize Regulatory Protein Opaque-2," The Plant Cell, 4: 1213-1227, (1992).
Weinmann et al., "A chimeric transactivator allows tetracycline-responsive gene expression in whole plants," The Plant J., vol. 5, No. 4: 559-569 (1994).
Yanofsky et al., "The protein encoded by the *Arabidopsis* homeotic gene *Agamous* resembles transcription factors," Nature, 346: 35-39, (1990).
Zhang et al., "Apoptosis Induced by Overexpression of *hMSH2* or *hMLH1*[1]," Cancer Res., 59: 3021-3027 (1999).
Hunter, et al., "The mismatch repair system contributes to meiotic sterility in an interspecific yeast hybrid," The EMBO Journal, 15:7, pp. 1726-1733, (1996).
de Wind, et al., "Inactivation of Mouse Msh2 Gene Results in Mismatch Repair Deficiency, Methylation Tolerance, Hyperrecombination, and Predisposition to Cancer," Cell, 82: 321-330 (1995).
Reenan, et al., "Isolation and Characterization of Two *Saccharomyces cerevisiae* Genes Encoding Homologs of the Bacterial HexA and MutS Mismatch Repair Proteins," Genetics, 132: 963-973 (1992).
Rayssiguier, et al., "The barrier to recombination between *Escherichia coli* and *Salmonella typhimurium* is disrupted in mismatch-repair mutants," Nature, 342 pp. 396-401 (1989).
Wu, et al., "Dominant Negative Mutator Mutations in the *mutS* Gene of *Escherichia coli*," Journal of Bacteriology, 176:17 pp. 5393-5400 (1994).
Argueso, J.L., Smith, D., Yi, J., Waase, M., Sarin, S., Alani, E.. 2002. Analysis of conditional mutations in the *Saccaromyces cerevisiae* MLH1 gene in mismatch repair and in meiotic crossing over. Genetics 160:909-921.
Blackwell, L. J., Bjornson, K.P., Allen, D.J., Modrich, P., 2001. Distinct MutS DNA-binding modes that are differentially modulated by ATP binding and hydrolysis. J. Biol. Chem. 276:34339-34347.
Iaccarino, I., Marra, G., Dufner, P., Jiricny, J. 2000. Mutation in the magnesium binding site of hMSH6 disables the hMutSalpha sliding clamp from translocating along DNA. J. Biol. Chem. 275:2080-2086.
Kato, R., Kataoka, M., Kamikubo, H., Kuramitsu, S. 2001. Direct observation of three conformations of MutS protein regulated by adenine nucleotides. J. Mol. Biol. 309:227-238.
Welz-Voegele, C., Stone, J.E., Tran, P.T., Kearney, H.M., Liskay, R.M., Petes, T.D., Jinks-Robertson, S. 2002. Alleles of the yeast Pms1 mismatch-repair gene that differentially affect recombination- and replication-related processes. Genetics 162:1131-1145.
Ramesh et al., "A Phylogenomic Inventory of Meiotic Genes: Evidence for Sex in Giardia and an Early Eukaryotic Origin of Meiosis", Current Biology, vol. 15, Jan. 26, 2005, 185-191.
Bogdanov et al., "Similarity of the Domain Structure of Proteins as a Basis for the Conservation of Meiosis", International Review of Cytology, vol. 257, 83-142, 2007.
Trude Schwarzacher, "Meiosis, recombination and chromosomes: a review of gene isolation and fluorescent in situ hybridization data in plants", Journal of Experimental Botany, vol. 54, No. 380, Plant Reproductive Biology Special Issue, 11-23, Jan. 2003.

(56) References Cited

OTHER PUBLICATIONS

Allen, D.J., Makhov, A., Grilley, M., Taylor J., Thresher, R., Modrich, P., Griffith, J.D., 1997, MutS mediates heteroduplex loop formation by a translocation mechanism, EMBO, J. 16:4467-4476.
Argueso, J.L., Smith, D., Yi, J., Waase, M., Sarin, S., Alani, E. 2002. Analysis of conditional mutations in the *Saccaromyces cerevisiae* MLH1 gene in mismatch repair and in meiotic crossing over. Genetics 160:909-921.
Blackwell, L. J., Bjomson, K.P., Allen, D.J., Modrich, P., 2001. Distinct MutS DNA-binding modes that are differentially modulated by ATP binding and hydrolysis. J. Biol. Chem. 276:34339-34347.
Blackwell, L.J., Martik, D., Bjornson, K.P., Bjomson, E.S., Modrich, P. 1998. Nucleotide-promoted release of hMutSalpha from heteroduplex DNA is consistent with an ATP-dependent translocation mechanism. J. Biol. Chem. 273:32055-32062.
Drotschmann, K., Clark, A.B., Tran, H.T., Resnick, M.A., Gordenin, D.A., Kunkel, T.A. 1999. Mutator phenotypes of yeast strains heterozygous for mutations in the MSH2 gene. PNAS 96:2970-2975.
Feng, G., Winkler, M.E. 1995. Single-step purifications of His6-MutH, His6-MutL and His6-MutS repair proteins of *Escherichia coli* K-12. Biotechniques 19:956-965.
Gill, D.R., Hatfull, G.F., Salmond, G.P. 1986. A new cell division operon in *Escherichia coli*. Mol. Gen Genet. 205:134:145.
Gradia, S., Acharya, S., Fishel, R., 1997. The human mismatch recognition complex hMSH2-hMSH6 functions as a novel molecular switch. Cell 91:995:1005.
Grilley, M., Welsh, K.M., Su, S.S., Modrich, P. 1989. Isolation and characterization of the *Escherichia coli* mutL gene product. J. Biol. Chem. 264:1000-1004.
Haber, L.T., Walker, G.C. 1991. Altering the conserved nucleotides binding motif in the *Salmonella typhimurium* MutS mismatch repair protein affects both its ATPase and mismatch binding activities. EMBO J. 10:2707-2715.
laccarino, I., Marra, G., Dufner, P., Jiricny, J. 2000. Mutation in the magnesium binding site of hMSH6 disables the hMutSalpha sliding clamp from translocating along DNA. J. Biol. Chem. 275:2080-2086.
Junop, M.S., Obmolova, G., Rausch, K., Hseih, P., Yang, W. 2001. Composite active site of an ABC ATPase: MutS uses ATP to verify mismatch recognition and authorize DNA repair. Mol. Cell 7:1-12.
Kato, R., Kataoka, M., Kamikubo, H., Kuramitsu, S. 2001. Direct observation of three conformations of MutS protein regulated by adenine nucleotides. J. Mol. Biol, 309:227-238.
Obmolova, G., Ban, C., Hsieh, P., Yang, W. 2000. Crystal structures of mismatch repair protein MutS and its complex with a substrate DNA. Nature 407:703-710.
Studamire, B., Quach, T., Alani, E., 1998. *Saccharomyces cerevisiae* Msh2p and Msh6p ATPase activities are both required during mismatch repair. Mol. Cell Biol. 18:7590-7601.
Walker, J.E., Saraste, M., Runswick, M.J., Gay, N.J. 1982. Distantly related sequences in the alpha- and beta-submits of ATP synthase, myosin, kinases and other ATP-requiring enzymes and a common nucleotide binding fold. EMBO J. 1:945-951.
Welz-Voegele, C., Stone, J.E., Tran, P.T., Keamey, H.M., Liskay, R.M., Petes, T.D., Jinks-Robertson, S. 2002. Alleles of the yeast Pms1 mismatch-repair gene that differentially affect recombination- and replication-related processes. Genetics 162:1131-1145.
Worth, L. Jr., Bader, T., Yang, J., Clark, S. 1998. Role of MutS ATPase activity in Muts, L-dependent block of invitro strand tranfer. J. Biol. Chem. 273-23176-23182.
Drotschmann, K., Aronshtam, A., Fritz, H., Marinus, M.G. 1998. The *Escherichia coli* MutL protein stimulates binding of Vsr and MutS to heteroduplex DNA. Nucl. Acids Research 26:948-953.
Schurko, Andrew M., et al., “Using a meiosis detection toolkit to investigate ancient asexual “scandals” and the evolution of sex”, BioEssays vol. 30(6), 2008, 579-589.
Schurko, Andrew M., et al., “Meiosis genes in *Daphnia pulex* and the role of parthenogenesis in genome evolution”, BMC Evolutionary, BMC Evolutionary Biology 2009, vol. 9(78), 1-27.
Christopher R. Trotta et al., “Coordinated nuclear export of 60S ribosomal subunits and NMD3 in verebrates”, The EMBO Journal, vol. 22(11), pp. 2841-2851, 2003.
Restriction Requirement dated Jun. 27, 2006 for US 2004/0023388.
Restriction Requirement dated Nov. 16, 2006 for US 2004/0023388.
Office Action dated Jun. 11, 2007 for US 2004/0023388.
Restriction Requirement dated Jan. 2, 2009 for US 2004/0023388.
Final Office Action dated Sep. 2, 2009 for US 2004/0023388.
Office Action dated Dec. 28, 2010 for US 2004/0023388.
Final Office Action dated Sep. 9, 2011 for US 2004/0023388.
Advisory Action dated Dec. 30, 2011 for US 2004/0023388.
Office Action dated Aug. 30, 2013 for US 2004/0023388.

* cited by examiner

NLS-MutS nucleotide sequence

GGATCCAAAAAAATGGCTCCTAAGAAGAAGAGAAAGGTTGGAGGAGGACC
CGGGAGTGCAATAGAAAATTTCGACGCCCATACGCCCATGATGCAGCAGT
ATCTCAGGCTGAAAGCCCAGCATCCCGAGATCCTGCTGTTTTACCGGATG
GGTGATTTTTATGAACTGTTTTATGACGACGCAAAACGCGCGTCGCAACT
GCTGGATATTTCACTGACCAAACGCGGTGCTTCGGCGGGAGAGCCGATCC
CGATGGCGGGGATTCCCTACCATGCGGTGGAAAACTATCTCGCCAAACTG
GTGAATCAGGGAGAGTCCGTTGCCATCTGCGAACAAATTGGCGATCCGGC
GACCAGCAAAGGTCCGGTTGAGCGCAAAGTTGTGCGTATCGTTACGCCAG
GCACCATCAGCGATGAAGCCCTGTTGCAGGAGCGTCAGGACAACCTGCTG
GCGGCTATCTGGCAGGACAGCAAAGGTTTCGGCTACGCGACGCTGGATAT
CAGTTCCGGGCGTTTTCGCCTGAGCGAACCGGCTGACCGCGAAACGATGG
CGGCAGAACTGCAACGCACTAATCCTGCGGAACTGCTGTATGCAGAAGAT
TTTGCTGAAATGTCGTTAATTGAAGGCCGTCGCGGCCTGCGCCGTCGCCC
GCTGTGGGAGTTTGAAATCGACACCGCGCGCCAGCAGTTGAATCTGCAAT
TTGGGACCCGCGATCTGGTCGGTTTTGGCGTCGAGAACGCGCCGCGCGGA
CTTTGTGCTGCCGGTTGTCTGTTGCAGTATGCGAAAGATACCCAACGTAC
GACTCTGCCGCATATTCGTTCCATCACCATGGAACGTGAGCAGGACAGCA
TCATTATGGATGCCGCGACGCGTCGTAATCTGGAAATCACCCAGAACCTG
GCGGGTGGTGCGGAAAATACGCTGGCTTCTGTGCTCGACTGCACCGTCAC
GCCGATGGGCAGCCGTATGCTGAAACGCTGGCTGCATATGCCAGTGCGCG
ATACCCGCGTGTTGCTTGAGCGCCAGCAAACTATTGGCGCATTGCAGGAT
TTCACCGCCGGGCTACAGCCGGTACTGCGTCAGGTCGGCGACCTGGAACG
TATTCTGGCACGTCTGGCTTTACGAACTGCTCGCCCACGCGATCTGGCCC
GTATGCGCCACGCTTTCCAGCAACTGCCGGAGCTGCGTGCGCAGTTAGAA
ACTGTCGATAGTGCACCGGTACAGGCGCTACGTGAGAAGATGGGCGAGTT
TGCCGAGCTGCGCGATCTGCTGGAGCGAGCAATCATCGACACACCGCCGG
TGCTGGTACGCGACGGTGGTGTTATCGCATCGGGCTATAACGAAGAGCTG
GATGAGTGGCGCGCGCTGGCTGACGGCGCGACCGATTATCTGGAGCGTCT
GGAAGTCCGCGAGCGTGAACGTACCGGCCTGGACACGCTGAAAGTTGGCT
TTAATGCGGTGCACGGCTACTACATTCAAATCAGCCGTGGGCAAAGCCAT
CTGGCACCCATCAACTACATGCGTCGCCAGACGCTGAAAAACGCCGAGCG
CTACATCATTCCAGAGCTAAAAGAGTACGAAGATAAAGTTCTCACCTCAA

Figure 2A-1

AAGGCAAAGCACTGGCACTGGAAAAACAGCTTTATGAAGAGCTGTTCGAC
CTGCTGTTGCCGCATCTGGAAGCGTTGCAACAGAGCGCGAGCGCGCTGGC
GGAACTCGACGTGCTGGTTAACCTGGCGGAACGGGCCTATACCCTGAACT
ACACCTGCCCGACCTTCATTGATAAACCGGGCATTCGCATTACCGAAGGT
CGCCATCCGGTAGTTGAACAAGTACTGAATGAGCCATTTATCGCCAACCC
GCTGAATCTGTCGCCGCAGCGCCGCATGTTGATCATCACCGGTCCGAACA
TGGGCGGTAAAAGTACCTATATGCGCCAGACCGCACTGATTGCGCTGATG
GCCTACATCGGCAGCTATGTACCGGCACAAAAAGTCGAGATTGGACCTAT
CGATCGCATCTTTACCCGCGTAGGCGCGGCAGATGACCTGGCGTCCGGGC
GCTCAACCTTTATGGTGGAGATGACTGAAACCGCCAATATTTTACATAAC
GCCACCGAATACAGTCTGGTGTTAATGGATGAGATCGGGCGTGGAACGTC
CACCTACGATGGTCTGTCGCTGGCGTGGGCGTGCGCGGAAAATCTGGCGA
ATAAGATTAAGGCATTGACGTTATTTGCTACCCACTATTTCGAGCTGACC
CAGTTACCGGAGAAAATGGAAGGCGTCGCTAACGTGCATCTCGATGCACT
GGAGCACGGCGACACCATTGCCTTTATGCACAGCGTGCAGGATGGCGCGG
CGAGCAAAAGCTACGGCCTGGCGGTTGCAGCTCTGGCAGGCGTGCCAAAA
GAGGTTATTAAGCGCGCACGGCAAAAGCTGCGTGAGCTGGAAAGCATTTC
GCCGAACGCCGCCGCTACGCAAGTGGATGGTACGCAAATGTCTTTGCTGT
CAGTACCAGAAGAAACTTCGCCTGCGGTCGAAGCTCTGGAAAATCTTGAT
CCGGATTCACTCACCCCGCGTCAGGCGCTGGAGTGGATTTATCGCTTGAA
GAGCCTGGTGTAATAACTGCAG

Figure 2A-2

NLS_MutL NUCLEOTIDE SEQUENCE

```
GGATCCAAAAAAATGGCTCCTAAGAAGAAGAGAAAGGTTGGAGGAGGACC
CGGGCCAATTCAGGTCTTACCGCCACAACTGGCGAACCAGATTGCCGCAG
GTGAGGTGGTCGAGCGACCTGCGTCGGTAGTCAAAGAACTAGTGGAAAAC
AGCCTCGATGCAGGTGCGACGCGTATCGATATTGATATCGAACGCGGTGG
GGCGAAACTTATCCGCATTCGTGATAACGGCTGCGGTATCAAAAAAGATG
AGCTGGCGCTGGCGCTGGCTCGTCATGCCACCAGTAAAATCGCCTCTCTG
GACGATCTCGAAGCCATTATCAGCCTGGGCTTTCGCGGTGAGGCGCTGGC
GAGTATCAGTTCGGTTTCCCGCCTGACGCTCACTTCACGCACCGCAGAAC
AGCAGGAAGCCTGGCAGGCCTATGCCGAAGGGCGCGATATGAACGTGACG
GTAAAACCGGCGGCGCATCCTGTGGGGACGACGCTGGAGGTGCTGGATCT
GTTCTACAACACCCCGGCGCGGCGCAAATTCCTGCGCACCGAGAAAACCG
AATTTAACCACATTGATGAGATCATCCGCCGCATTGCGCTGGCGCGTTTC
GACGTCACGATCAACCTGTCGCATAACGGTAAAATTGTGCGTCAGTACCG
CGCAGTGCCGGAAGGCGGGCAAAAAGAACGGCGCTTAGGCGCGATTTGCG
GCACCGCTTTTCTTGAACAAGCGCTGGCGATTGAATGGCAACACGGCGAT
CTCACGCTACGCGGCTGGGTGGCCGATCCAAATCACACCACGCCCGCACT
GGCAGAAATTCAGTATTGCTACGTGAACGGTCGCATGATGCGCGATCGCC
TGATCAATCACGCGATCCGCCAGGCCTGCGAAGACAAACTGGGGGCCGAT
CAGCAACCGGCATTTGTGTTGTATCTGGAGATCGACCCACATCAGGTGGA
CGTCAACGTGCACCCCGCCAAACACGAAGTGCGTTTCCATCAGTCGCGTC
TGGTGCATGATTTTATCTATCAGGGCGTGCTGAGCGTGCTACAACAGCAA
CTGGAAACGCCGCTACCGCTGGACGATGAACCCCAACCTGCACCGCGTTC
CATTCCGGAAAACCGCGTGGCGGCGGGGCGCAATCACTTTGCAGAACCGG
CAGCTCGTGAGCCGGTAGCTCCGCGCTACACTCCTGCGCCAGCATCAGGC
AGTCGTCCGGCTGCCCCCTGGCCGAATGCGCAGCCAGGCTACCAGAAACA
GCAAGGTGAAGTGTATCGCCAGCTTTTGCAAACGCCCGCGCCGATGCAAA
AATTAAAAGCGCCGGAACCGCAGGAACCTGCACTTGCGGCGAACAGTCAG
AGTTTTGGTCGGGTACTGACTATCGTCCATTCCGACTGTGCGTTGCTGGA
GCGCGACGGCAACATTTCACTTTTATCCTTGCCAGTGGCAGAACGTTGGC
TGCGTCAGGCACAATTGACGCCGGGTGAAGCGCCCGTTTGCGCCCAGCCG
CTGCTGATTCCGTTGCGGCTAAAAGTTTCTGCCGAAGAAAAATCGGCATT
AGAAAAAGCGCAGTCTGCCCTGGCGGAATTGGGTATTGATTTCCAGTCAG
ATGCACAGCATGTGACCATCAGGGCAGTGCCTTTACCCTTACGCCAACAA
AATTTACAAATCTTGATTCCTGAACTGATAGGCTACCTGGCGAAGCAGTC
CGTATTCGAACCTGGCAATATTGCGCAGTGGATTGCACGAAATCTGATGA
GCGAACATGCGCAGTGGTCAATGGCACAGGCCATAACCCTGCTGGCGGAC
GTGGAACGGTTATGTCCGCAACTTGTGAAAACGCCGCCGGGTGGTCTGTT
ACAATCTGTTGATTTACATCCGGCGATAAAAGCCCTGAAAGATGAGTGAT
                  GACTGCAG
```

Figure 2B

NLS-MutH Nucleotide Sequence

GGATCCAAAAAAATGGCTCCTAAGAAGAAGAGAAAGGTTGGAGGAGGACC
CGGGCCAATTCAGGTCTTACCGCCACAACTGGCGAACCAGATTGCCGCAG
GTGAGGTGGTCGAGCGACCTGCGTCGGTAGTCAAAGAACTAGTGGAAAAC
AGCCTCGATGCAGGTGCGACGCGTATCGATATTGATATCGAACGCGGTGG
GGCGAAACTTATCCGCATTCGTGATAACGGCTGCGGTATCAAAAAAGATG
AGCTGGCGCTGGCGCTGGCTCGTCATGCCACCAGTAAAATCGCCTCTCTG
GACGATCTCGAAGCCATTATCAGCCTGGGCTTTCGCGGTGAGGCGCTGGC
GAGTATCAGTTCGGTTTCCCGCCTGACGCTCACTTCACGCACCGCAGAAC
AGCAGGAAGCCTGGCAGGCCTATGCCGAAGGGCGCGATATGAACGTGACG
GTAAAACCGGCGGCGCATCCTGTGGGACGACGCTGGAGGTGCTGGATCT
GTTCTACAACACCCCGGCGCGGCGCAAATTCCTGCGCACCGAGAAAACCG
AATTTAACCACATTGATGAGATCATCCGCCGCATTGCGCTGGCGCGTTTC
GACGTCACGATCAACCTGTCGCATAACGGTAAAATTGTGCGTCAGTACCG
CGCAGTGCCGGAAGGCGGGCAAAAAGAACGGCGCTTAGGCGCGATTTGCG
GCACCGCTTTTCTTGAACAAGCGCTGGCGATTGAATGGCAACACGGCGAT
CTCACGCTACGCGGCTGGGTGGCCGATCCAAATCACACCACGCCCGCACT
GGCAGAAATTCAGTATTGCTACGTGAACGGTCGCATGATGCGCGATCGCC
TGATCAATCACGCGATCCGCCAGGCCTGCGAAGACAAACTGGGGGCCGAT
CAGCAACCGGCATTTGTGTTGTATCTGGAGATCGACCCACATCAGGTGGA
CGTCAACGTGCACCCCGCCAAACACGAAGTGCGTTTCCATCAGTCGCGTC
TGGTGCATGATTTTATCTATCAGGGCGTGCTGAGCGTGCTACAACAGCAA
CTGGAAACGCCGCTACCGCTGGACGATGAACCCCAACCTGCACCGCGTTC
CATTCCGGAAAACCGCGTGGCGGCGGGGCGCAATCACTTTGCAGAACCGG
CAGCTCGTGAGCCGGTAGCTCCGCGCTACACTCCTGCGCCAGCATCAGGC
AGTCGTCCGGCTGCCCCCTGGCCGAATGCGCAGCCAGGCTACCAGAAACA
GCAAGGTGAAGTGTATCGCCAGCTTTTGCAAACGCCCGCGCCGATGCAAA
AATTAAAAGCGCCGGAACCGCAGGAACCTGCACTTGCGGCGAACAGTCAG
AGTTTTGGTCGGGTACTGACTATCGTCCATTCCGACTGTGCGTTGCTGGA
GCGCGACGGCAACATTTCACTTTTATCCTTGCCAGTGGCAGAACGTTGGC
TGCGTCAGGCACAATTGACGCCGGGTGAAGCGCCCGTTTGCGCCCAGCCG
CTGCTGATTCCGTTGCGGCTAAAAGTTTCTGCCGAAGAAAAATCGGCATT
AGAAAAAGCGCAGTCTGCCCTGGCGGAATTGGGTATTGATTTCCAGTCAG
ATGCACAGCATGTGACCATCAGGGCAGTGCCTTTACCCTTACGCCAACAA
AATTTACAAATCTTGATTCCTGAACTGATAGGCTACCTGGCGAAGCAGTC
CGTATTCGAACCTGGCAATATTGCGCAGTGGATTGCACGAAATCTGATGA
GCGAACATGCGCAGTGGTCAATGGCACAGGCCATAACCCTGCTGGCGGAC
GTGGAACGGTTATGTCCGCAACTTGTGAAAACGCCGCCGGGTGGTCTGTT
ACAATCTGTTGATTTACATCCGGCGATAAAAGCCCTGAAAGATGAGTGAT
GACTGCAG

Figure 2C

NLS-MutU Nucleotide Sequence

GCCATGGACGTTTCTTACCTGCTCGACAGCCTTAATGACAAACAGCGCGA
AGCGGTGGCCGCGCCACGCAGCAACCTTCTGGTGCTGGCGGGCGCGGGCA
GTGGTAAGACGCGCGTACTGGTGCATCGTATCGCCTGGTTGATGAGCGTG
GAAAACTGCTCGCCATACTCGATTATGGCGGTGACGTTTACCAACAAAGC
GGCGGCGGAGATGCGTCATCGTATCGGGCAACTGATGGGCACGAGCCAGG
GCGGTATGTGGGTCGGCACCTTCCACGGGCTGGCGCACCGTTTGCTGCGT
GCGCACCATATGGACGCCAATCTGCCGCAGGATTTCCAGATCCTCGACAG
TGAAGACCAGCTACGCCTGCTTAAGCGTCTGATCAAAGCCATGAACCTCG
ACGAGAAGCAGTGGCCGCCGCGGCAGGCAATGTGGTACATCAACAGCCAG
AAAGATGAAGGCCTGCGTCCGCATCATATTCAAAGCTACGGTAATCCGGT
GGAGCAGACCTGGCAGAAGGTGTATCAGGCGTATCAGGAAGCGTGTGACC
GCGCGGGCCTGGTGGACTTCGCCGAGCTGCTGCTGCGCGCTCACGAGTTG
TGGCTTAACAAGCCGCATATCCTGCAACACTACCGCGAACGTTTTACCAA
TATCCTGGTGGACGAATTCCAGGATACCAACAACATTCAGTACGCGTGGA
TCCGCCTGCTGGCGGGCGACACCGGCAAAGTGATGATCGTCGGTGATGAC
GACCAGTCAATCTACGGCTGGCGCGGGGCGCAGGTGGAGAATATTCAGCG
TTTCCTTAATGATTTCCCCGGTGCCGAAACTATTCGTCTGGAGCAAAACT
ACCGCTCTACCAGCAATATTCTGAGCGCCGCTAACGCCCTGATTGAAAAC
AATAACGGGCGTCTGGGTAAAAAACTGTGGACCGATGGCGCGGACGGTGA
GCCTATTTCCCTCTATTGCGCTTTTAACGAACTCGATGAAGCGCGTTTTG
TGGTTAACCGCATCAAAACCTGGCAGGACAACGGCGGAGCGCTTGCCGAG
TGCGCCATTCTCTACCGCAGCAACGCCCAGTCGCGGGTGCTCGAAGAGGC
GTTATTGCAGGCCAGTATGCCGTACCGTATTTACGGCGGGATGCGCTTCT
TCGAACGCCAGGAAATCAAAGATGCGCTCTCGTATCTGCGCCTGATTGCC
AACCGCAACGACGACGCGGCCTTTGAGCGTGTGGTGAATACGCCAACGCG
GGGTATTGGTGACCGGACGCTGGACGTGGTACGTCAGACATCGCGCGATC
GCCAGTTAACACTCTGGCAGGCATGTCGTGAGCTGTTGCAGGAAAAAGCC
CTCGCCGGGCGAGCTGCCAGCGCCTTGCAGCGATTTATGGAATTAATCGA
CGCCTTAGCGCAGGAAACTGCCGATATGCCGCTGCATGTACAGACTGACC
GGGTAATTAAAGACTCCGGCCTGCGTACCATGTATGAGCAGGAGAAGGGC
GAAAAAGGTCAGACGCGTATCGAAAACTTAGAGGAACTGGTGACGGCAAC
GCGCCAGTTCAGCTACAACGAAGAAGACGAAGATTTAATGCCGCTGCAGG
CGTTCCTCTCCCATGCGGCACTGGAAGCAGGTGAAGGGCAGGCGGATACC
TGGCAGGATGCGGTGCAGTTGATGACGCTACACTCGGCGAAAGGCCTGGA
GTTCCCGCAGGTGTTTATCGTTGGTATGGAAGAGGGCATGTTCCCAAGCC
AGATGTCGCTGGATGAAGGCGGGCGTCTGGAAGAAGAACGCCGTCTGGCC
TACGTTGGCGTAACCCGCGCGATGCAGAAACTGACGCTGACCTACGCGGA
AACCCGCCGTCTGTATGGTAAAGAGGTTTACCATCGCCCGTCGCGCTTTA
TCGGCGAGCTGCCGGAAGAGTGTGTGGAAGAGGTGCGCCTGCGCGCCACG
GTAAGCCGCCCGGTCAGCCATCAGCGGATGGGTACGCCGATGGTCGAGAA
CGACAGCGGCTACAAGCTCGGCCAGCGCGTACGCCACGCTAAGTTTGGTG
AAGGCACCATTGTCAATATGGAAGGCAGCGGTGAGCATAGCCGTTTGCAG
GTGGCATTTCAGGGCCAGGGTATTAAATGGCTGGTGGCGGCATACGCCCG
GCTGGAGTCGGTGGGCGCCGGTGGAGGTGGAGGTGGAGGTGGACCCGGGC
TTTCAAAGCGTCCGCGTGAAGATGATGATGGAGAACCGAGTGAACGCAAA
CGCGAGAGAGATGAGGTTAACGGTGATTACAAGGATGATGATGATAAGTA
ATAACTGCAGGAT

Figure 2D

NLS-MutS RS Nucleotide Sequence

GGATCCAAAACAATGGCTCCTAAGAAGAAGAGGAAGGTTGGTGGAGGTGA
TTACAAGGATGATGATGATAAGGGTGGAGGTGGAGGTGGAGGTGGAGGTG
GAGGTGGAATGTCTGCTATCGAGAACTTCGATGCTCACACCCCTATGATG
CAGCAGTACCTCAGGCTCAAGGCTCAGCACCCTGAGATCCTCCTCTTCTA
CAGGATGGGAGATTTCTACGAGCTCTTCTACGATGATGCTAAGAGGGCTT
CTCAGCTCCTCGATATCTCTCTCACCAAGAGGGGAGCTTCTGCTGGAGAG
CCTATCCCTATGGCTGGAATCCCTTACCACGCTGTTGAGAACTACCTCGC
TAAGCTTGTTAACCAGGGAGAGTCTGTTGCTATCTGCGAGCAGATCGGAG
ATCCTGCTACCTCTAAGGGACCTGTTGAGAGGAAGGTTGTTAGGATCGTT
ACCCCTGGAACCATCTCTGATGAGGCTCTCCTCCAGGAGAGGCAGGATAA
CCTCCTCGCTGCTATCTGGCAGGATTCTAAGGGATTCGGATACGCTACCC
TCGATATCTCTTCTGGAAGGTTCAGGCTCTCTGAGCCTGCTGATAGGGAG
ACCATGGCTGCTGAGCTCCAGAGGACCAACCCTGCTGAGCTCCTCTACGC
TGAGGATTTCGCTGAGATGTCTCTCATCGAGGGAAGGAGGGGACTCAGGA
GGAGGCCTCTCTGGGAGTTCGAGATCGATACCGCTAGGCAGCAGCTCAAC
CTCCAGTTCGGAACCAGGGATCTCGTTGGATTCGGAGTTGAGAACGCTCC
TAGGGGACTCTGCGCTGCTGGATGCCTCCTCCAGTACGCTAAGGATACCC
AGAGGACCACCCTCCCTCACATCAGGTCTATCACCATGGAGAGGGAGCAG
GATTCTATCATCATGGATGCTGCTACCAGGAGGAACCTCGAGATCACCCA
GAACCTCGCTGGAGGAGCTGAGAACACCCTCGCTTCTGTTCTCGATTGCA
CCGTTACCCCTATGGGATCTAGGATGCTCAAGAGGTGGCTCCACATGCCT
GTTAGGGATACCAGGGTTCTCCTCGAGAGGCAGCAGACCATCGGAGCTCT
CCAGGATTTCACCGCTGGACTCCAGCCTGTTCTCAGGCAGGTTGGAGATC
TCGAGAGAATCCTCGCTAGGCTCGCTCTCAGGACCGCTAGGCCTAGGGAT
CTCGCTAGGATGAGGCACGCTTTCCAGCAGCTCCCTGAGCTCAGGGCTCA
GCTCGAGACCGTTGATTCTGCTCCTGTTCAGGCTCTCAGGGAGAAGATGG
GAGAGTTCGCTGAGCTCAGGGATCTCCTCGAGAGGGCTATCATCGATACC
CCTCCTGTTCTCGTTAGGGATGGAGGAGTTATCGCTTCTGGATACAACGA
GGAGCTCGATGAGTGGAGGGCTCTCGCTGATGGAGCTACCGATTACCTCG
AGAGGCTCGAGGTTAGGGAGAGGGAGAGGACCGGACTCGATACCCTCAAG
GTTGGATTCAACGCTGTTCACGGATACTACATCCAGATCTCTAGGGGACA
GTCTCACCTCGCTCCTATCAACTACATGAGGAGGCAGACCCTCAAGAACG
CTGAGAGGTACATCATCCCTGAGCTCAAGGAGTACGAGGATAAGGTTCTC
ACCTCTAAGGGAAAGGCTCTCGCTCTCGAGAAGCAGCTCTACGAGGAGCT
CTTCGATCTCCTCCTCCCTCACCTCGAGGCTCTCCAGCAGTCTGCTTCTG
CTCTCGCTGAGCTCGATGTTCTCGTTAACCTCGCTGAGAGGGCTTACACC
CTCAACTACACCTGCCCTACCTTCATCGATAAGCCTGGAATCAGGATCAC
CGAGGGAAGGCACCCTGTTGTTGAGCAGGTTCTCAACGAGCCTTTCATCG
CTAACCCTCTCAACCTCTCTCCTCAGAGGAGGATGCTCATCATCACCGGA
CCTAACATGGGAGGAAAGTCTACCTACATGAGGCAGACCGCTCTCATCGC
TCTCATGGCTTACATCGGATCTTACGTTCCTGCTCAGAAGGTTGAGATCG
GACCTATCGATAGGATCTTCACCAGGGTTGGAGCTGCTGATGATCTCGCT
TCTGGAAGGTCTACCTTCATGGTTGAGATGACCGAGACCGCTAACATCCT
CCACAACGCTACCGAGTACTCTCTCGTTCTCATGGATGAGATCGGAAGGG
GAACCTCTACCTACGATGGACTCTCTCTCGCTTGGGCTTGCGCTGAGAAC
CTCGCTAACAAGATCAAGGCTCTCACCCTCTTCGCTACCCACTACTTCGA
GCTCACCCAGCTCCCTGAGAAGATGGAGGGAGTTGCTAACGTTCACCTCG
ATGCTCTCGAGCACGGAGATACCATCGCTTTCATGCACTCTGTTCAGGAT
GGAGCTGCTTCTAAGTCTTACGGACTCGCTGTTGCTGCTCTCGCTGGAGT
TCCTAAGGAGGTTATCAAGAGGGCTAGGCAGAAGCTCAGGGAGCTCGAGT
CTATCTCTCCTAACGCTGCTGCTACCCAGGTTGATGGAACCCAGATGTCT
CTCCTCTCTGTTCCTGAGGAGACCTCTCCTGCTGTTGAGGCTCTCGAGAA
CCTCGATCCTGATTCTCTCACCCCTAGGCAGGCTCTCGAGTGGATCTACA
GGCTCAAGTCTCTCGTTTAATGATGAGCGGCCGCGAATTC

Figure 2E

SEQUENCE LISTING

```
<160> NUMBER OF SEQ ID NOS: 32

<210> SEQ ID NO 1
<211> LENGTH: 2622
<212> TYPE: DNA
<213> ORGANISM: Artificial sequence
<220> FEATURE:
<223> OTHER INFORMATION: NLS-MutS (MutS from E.coli fused to NLS from
      SV40 T=Antigen)

<400> SEQUENCE: 1

ggatccaaaa aaatggctcc taagaagaag agaaaggttg gaggaggacc cgggagtgca     60

atagaaaatt tcgacgccca tacgcccatg atgcagcagt atctcaggct gaaagcccag    120

catcccgaga tcctgctgtt ttaccggatg ggtgattttt atgaactgtt ttatgacgac    180

gcaaaacgcg cgtcgcaact gctggatatt tcactgacca aacgcggtgc ttcggcggga    240

gagccgatcc cgatggcggg gattccctac catgcggtgg aaaactatct cgccaaactg    300

gtgaatcagg gagagtccgt tgccatctgc gaacaaattg gcgatccggc gaccagcaaa    360

ggtccggttg agcgcaaagt tgtgcgtatc gttacgccag gcaccatcag cgatgaagcc    420

ctgttgcagg agcgtcagga caacctgctg gcggctatct ggcaggacag caaaggtttc    480

ggctacgcga cgctggatat cagttccggg cgttttcgcc tgagcgaacc ggctgaccgc    540

gaaacgatgg cggcagaact gcaacgcact aatcctgcgg aactgctgta tgcagaagat    600

tttgctgaaa tgtcgttaat tgaaggccgt cgcggcctgc gccgtcgccc gctgtgggag    660
```

```
tttgaaatcg acaccgcgcg ccagcagttg aatctgcaat ttgggacccg cgatctggtc    720

ggttttggcg tcgagaacgc gccgcgcgga ctttgtgctg ccggttgtct gttgcagtat    780

gcgaaagata cccaacgtac gactctgccg catattcgtt ccatcaccat ggaacgtgag    840

caggacagca tcattatgga tgccgcgacg cgtcgtaatc tggaaatcac ccagaacctg    900

gcgggtggtg cggaaaatac gctggcttct gtgctcgact gcaccgtcac gccgatgggc    960

agccgtatgc tgaaacgctg gctgcatatg ccagtgcgcg atacccgcgt gttgcttgag   1020

cgccagcaaa ctattggcgc attgcaggat ttcaccgccg ggctacagcc ggtactgcgt   1080

caggtcggcg acctggaacg tattctggca cgtctggctt tacgaactgc tcgcccacgc   1140

gatctggccc gtatgcgcca cgctttccag caactgccgg agctgcgtgc gcagttagaa   1200

actgtcgata gtgcaccggt acaggcgcta cgtgagaaga tgggcgagtt tgccgagctg   1260

cgcgatctgc tggagcgagc aatcatcgac acaccgccgg tgctggtacg cgacggtggt   1320

gttatcgcat cgggctataa cgaagagctg gatgagtggc gcgcgctggc tgacggcgcg   1380

accgattatc tggagcgtct ggaagtccgc gagcgtgaac gtaccggcct ggacacgctg   1440

aaagttggct ttaatgcggt gcacggctac tacattcaaa tcagccgtgg gcaaagccat   1500

ctggcaccca tcaactacat gcgtcgccag acgctgaaaa acgccgagcg ctacatcatt   1560

ccagagctaa aagagtacga agataaagtt ctcacctcaa aaggcaaagc actggcactg   1620

gaaaaacagc tttatgaaga gctgttcgac ctgctgttgc cgcatctgga agcgttgcaa   1680

cagagcgcga gcgcgctggc ggaactcgac gtgctggtta acctggcgga acgggcctat   1740

accctgaact acacctgccc gaccttcatt gataaaccgg gcattcgcat taccgaaggt   1800

cgccatccgg tagttgaaca agtactgaat gagccattta tcgccaaccc gctgaatctg   1860

tcgccgcagc gccgcatgtt gatcatcacc ggtccgaaca tgggcggtaa aagtacctat   1920

atgcgccaga ccgcactgat tgcgctgatg gcctacatcg gcagctatgt accggcacaa   1980

aaagtcgaga ttggacctat cgatcgcatc tttacccgcg taggcgcggc agatgacctg   2040

gcgtccgggc gctcaacctt tatggtggag atgactgaaa ccgccaatat tttacataac   2100

gccaccgaat acagtctggt gttaatggat gagatcgggc gtggaacgtc cacctacgat   2160

ggtctgtcgc tggcgtgggc gtgcgcggaa aatctggcga ataagattaa ggcattgacg   2220

ttatttgcta cccactattt cgagctgacc cagttaccgg agaaaatgga aggcgtcgct   2280

aacgtgcatc tcgatgcact ggagcacggc gacaccattg cctttatgca cagcgtgcag   2340

gatggcgcgg cgagcaaaag ctacggcctg gcggttgcag ctctggcagg cgtgccaaaa   2400

gaggttatta agcgcgcacg gcaaaagctg cgtgagctgg aaagcatttc gccgaacgcc   2460

gccgctacgc aagtggatgg tacgcaaatg tctttgctgt cagtaccaga agaaacttcg   2520

cctgcggtcg aagctctgga aaatcttgat ccggattcac tcaccccgcg tcaggcgctg   2580

gagtggattt atcgcttgaa gagcctggtg taataactgc ag                      2622
```

<210> SEQ ID NO 2
<211> LENGTH: 1908
<212> TYPE: DNA
<213> ORGANISM: Artificial sequence
<220> FEATURE:
<223> OTHER INFORMATION: NLS-MutL (MutL from E.coli fused to NLS from SV40 T-Antigen)

<400> SEQUENCE: 2

```
ggatccaaaa aaatggctcc taagaagaag agaaaggttg gaggaggacc cgggccaatt     60

caggtcttac cgccacaact ggcgaaccag attgccgcag gtgaggtggt cgagcgacct    120
```

gcgtcggtag tcaaagaact agtggaaaac agcctcgatg caggtgcgac gcgtatcgat 180
attgatatcg aacgcggtgg ggcgaaactt atccgcattc gtgataacgg ctgcggtatc 240
aaaaaagatg agctggcgct ggcgctggct cgtcatgcca ccagtaaaat cgcctctctg 300
gacgatctcg aagccattat cagcctgggc tttcgcggtg aggcgctggc gagtatcagt 360
tcggtttccc gcctgacgct cacttcacgc accgcagaac agcaggaagc ctggcaggcc 420
tatgccgaag ggcgcgatat gaacgtgacg gtaaaaccgg cggcgcatcc tgtggggacg 480
acgctggagg tgctggatct gttctacaac accccggcgc ggcgcaaatt cctgcgcacc 540
gagaaaaccg aatttaacca cattgatgag atcatccgcc gcattgcgct ggcgcgtttc 600
gacgtcacga tcaacctgtc gcataacggt aaaattgtgc gtcagtaccg cgcagtgccg 660
gaaggcgggc aaaaagaacg gcgcttaggc gcgatttgcg gcaccgcttt tcttgaacaa 720
gcgctggcga ttgaatggca acacggcgat ctcacgctac gcggctgggt ggccgatcca 780
aatcacacca cgcccgcact ggcagaaatt cagtattgct acgtgaacgg tcgcatgatg 840
cgcgatcgcc tgatcaatca cgcgatccgc caggcctgcg aagacaaact gggggccgat 900
cagcaaccgg catttgtgtt gtatctggag atcgacccac atcaggtgga cgtcaacgtg 960
caccccgcca aacacgaagt gcgtttccat cagtcgcgtc tggtgcatga ttttatctat 1020
cagggcgtgc tgagcgtgct acaacagcaa ctggaaacgc cgctaccgct ggacgatgaa 1080
ccccaacctg caccgcgttc cattccggaa aaccgcgtgg cggcggggcg caatcacttt 1140
gcagaaccgg cagctcgtga gccggtagct ccgcgctaca ctcctgcgcc agcatcaggc 1200
agtcgtccgg ctgccccctg gccgaatgcg cagccaggct accagaaaca gcaaggtgaa 1260
gtgtatcgcc agcttttgca aacgcccgcg ccgatgcaaa aattaaaagc gccggaaccg 1320
caggaacctg cacttgcggc gaacagtcag agttttggtc gggtactgac tatcgtccat 1380
tccgactgtg cgttgctgga gcgcgacggc aacatttcac ttttatcctt gccagtggca 1440
gaacgttggc tgcgtcaggc acaattgacg ccgggtgaag cgcccgtttg cgcccagccg 1500
ctgctgattc cgttgcggct aaaagtttct gccgaagaaa aatcggcatt agaaaaagcg 1560
cagtctgccc tggcggaatt gggtattgat ttccagtcag atgcacagca tgtgaccatc 1620
agggcagtgc ctttaccctt acgccaacaa aatttacaaa tcttgattcc tgaactgata 1680
ggctacctgg cgaagcagtc cgtattcgaa cctggcaata ttgcgcagtg gattgcacga 1740
aatctgatga gcgaacatgc gcagtggtca atggcacagg ccataaccct gctggcggac 1800
gtggaacggt tatgtccgca acttgtgaaa acgccgccgg gtggtctgtt acaatctgtt 1860
gatttacatc cggcgataaa agccctgaaa gatgagtgat gactgcag 1908

<210> SEQ ID NO 3
<211> LENGTH: 1908
<212> TYPE: DNA
<213> ORGANISM: Artificial sequence
<220> FEATURE:
<223> OTHER INFORMATION: NLS-MutH (MutH from E.coli fused to NLS from SV40 T-Antigen)

<400> SEQUENCE: 3
ggatccaaaa aaatggctcc taagaagaag agaaaggttg gaggaggacc cgggccaatt 60
caggtcttac cgccacaact ggcgaaccag attgccgcag gtgaggtggt cgagcgacct 120
gcgtcggtag tcaaagaact agtggaaaac agcctcgatg caggtgcgac gcgtatcgat 180
attgatatcg aacgcggtgg ggcgaaactt atccgcattc gtgataacgg ctgcggtatc 240

-continued

```
aaaaaagatg agctggcgct ggcgctggct cgtcatgcca ccagtaaaat cgcctctctg    300

gacgatctcg aagccattat cagcctgggc tttcgcggtg aggcgctggc gagtatcagt    360

tcggtttccc gcctgacgct cacttcacgc accgcagaac agcaggaagc ctggcaggcc    420

tatgccgaag ggcgcgatat gaacgtgacg gtaaaaccgg cggcgcatcc tgtggggacg    480

acgctggagg tgctggatct gttctacaac accccggcgc ggcgcaaatt cctgcgcacc    540

gagaaaaccg aatttaacca cattgatgag atcatccgcc gcattgcgct ggcgcgtttc    600

gacgtcacga tcaacctgtc gcataacggt aaaattgtgc gtcagtaccg cgcagtgccg    660

gaaggcgggc aaaaagaacg gcgcttaggc gcgatttgcg gcaccgcttt tcttgaacaa    720

gcgctggcga ttgaatggca acacggcgat ctcacgctac gcggctgggt ggccgatcca    780

aatcacacca cgcccgcact ggcagaaatt cagtattgct acgtgaacgg tcgcatgatg    840

cgcgatcgcc tgatcaatca cgcgatccgc caggcctgcg aagacaaact gggggccgat    900

cagcaaccgg catttgtgtt gtatctggag atcgacccac atcaggtgga cgtcaacgtg    960

caccccgcca aacacgaagt gcgtttccat cagtcgcgtc tggtgcatga ttttatctat   1020

cagggcgtgc tgagcgtgct acaacagcaa ctggaaacgc cgctaccgct ggacgatgaa   1080

ccccaacctg caccgcgttc cattccggaa aaccgcgtgg cggcggggcg caatcacttt   1140

gcagaaccgg cagctcgtga gccggtagct ccgcgctaca ctcctgcgcc agcatcaggc   1200

agtcgtccgg ctgccccctg gccgaatgcg cagccaggct accagaaaca gcaaggtgaa   1260

gtgtatcgcc agcttttgca aacgcccgcg ccgatgcaaa aattaaaagc gccggaaccg   1320

caggaacctg cacttgcggc gaacagtcag agttttggtc gggtactgac tatcgtccat   1380

tccgactgtg cgttgctgga gcgcgacggc aacatttcac ttttatcctt gccagtggca   1440

gaacgttggc tgcgtcaggc acaattgacg ccgggtgaag cgcccgtttg cgcccagccg   1500

ctgctgattc cgttgcggct aaaagtttct gccgaagaaa aatcggcatt agaaaaagcg   1560

cagtctgccc tggcggaatt gggtattgat ttccagtcag atgcacagca tgtgaccatc   1620

agggcagtgc ctttaccctt acgccaacaa aatttacaaa tcttgattcc tgaactgata   1680

ggctacctgg cgaagcagtc cgtattcgaa cctggcaata ttgcgcagtg gattgcacga   1740

aatctgatga gcgaacatgc gcagtggtca atggcacagg ccataaccct gctggcggac   1800

gtggaacggt tatgtccgca acttgtgaaa acgccgccgg gtggtctgtt acaatctgtt   1860

gatttacatc cggcgataaa agccctgaaa gatgagtgat gactgcag                1908
```

<210> SEQ ID NO 4
<211> LENGTH: 16
<212> TYPE: PRT
<213> ORGANISM: Artificial sequence
<220> FEATURE:
<223> OTHER INFORMATION: NLS of AGAMOUS protein

<400> SEQUENCE: 4

```
Arg Ile Glu Asn Thr Thr Asn Arg Gln Val Thr Phe Cys Lys Arg Arg
1               5                   10                  15
```

<210> SEQ ID NO 5
<211> LENGTH: 18
<212> TYPE: PRT
<213> ORGANISM: Artificial sequence
<220> FEATURE:
<223> OTHER INFORMATION: NLS of TGA-1A protein

<400> SEQUENCE: 5

```
Arg Arg Leu Ala Gln Asn Arg Glu Ala Ala Arg Lys Ser Arg Leu Arg
```

1 5 10 15

Lys Lys

<210> SEQ ID NO 6
<211> LENGTH: 21
<212> TYPE: PRT
<213> ORGANISM: Artificial sequence
<220> FEATURE:
<223> OTHER INFORMATION: NLS of TGA-1B protein

<400> SEQUENCE: 6

Lys Lys Arg Ala Arg Leu Val Arg Asn Arg Glu Ser Ala Gln Leu Ser
1 5 10 15

Arg Gln Arg Lys Lys
20

<210> SEQ ID NO 7
<211> LENGTH: 18
<212> TYPE: PRT
<213> ORGANISM: Artificial sequence
<220> FEATURE:
<223> OTHER INFORMATION: NLS of O2 NLS B protein

<400> SEQUENCE: 7

Arg Lys Arg Lys Glu Ser Asn Arg Glu Ser Ala Arg Arg Ser Arg Tyr
1 5 10 15

Arg Lys

<210> SEQ ID NO 8
<211> LENGTH: 45
<212> TYPE: PRT
<213> ORGANISM: Artificial sequence
<220> FEATURE:
<221> NAME/KEY: misc_feature
<222> LOCATION: (11)..(42)
<223> OTHER INFORMATION: "Xaa" is any amino acid

<400> SEQUENCE: 8

Lys Lys Asn Gln Lys His Lys Leu Lys Met Xaa Xaa Xaa Xaa Xaa Xaa
1 5 10 15

Xaa Xaa Xaa Xaa Xaa Xaa Xaa Xaa Xaa Xaa Xaa Xaa Xaa Xaa Xaa Xaa
20 25 30

Xaa Xaa Xaa Xaa Xaa Xaa Xaa Xaa Xaa Xaa Lys Arg Lys
35 40 45

<210> SEQ ID NO 9
<211> LENGTH: 16
<212> TYPE: PRT
<213> ORGANISM: Artificial sequence
<220> FEATURE:
<223> OTHER INFORMATION: NLS of nucleoplasmin protein

<400> SEQUENCE: 9

Lys Arg Pro Ala Ala Thr Lys Lys Ala Gly Gln Ala Lys Lys Lys Lys
1 5 10 15

<210> SEQ ID NO 10
<211> LENGTH: 17
<212> TYPE: PRT
<213> ORGANISM: Artificial sequence
<220> FEATURE:
<223> OTHER INFORMATION: NLS of NO38 protein

<400> SEQUENCE: 10

Lys Arg Ile Ala Pro Asp Ser Ala Ser Lys Val Pro Arg Lys Lys Thr 1 5 10 15

Arg

<210> SEQ ID NO 11
<211> LENGTH: 17
<212> TYPE: PRT
<213> ORGANISM: Artificial sequence
<220> FEATURE:
<223> OTHER INFORMATION: NLS of N1/N2 protein

<400> SEQUENCE: 11

Lys Arg Lys Thr Glu Glu Glu Ser Pro Leu Lys Asp Lys Asp Ala Lys
1 5 10 15

Lys

<210> SEQ ID NO 12
<211> LENGTH: 17
<212> TYPE: PRT
<213> ORGANISM: Artificial sequence
<220> FEATURE:
<223> OTHER INFORMATION: NLS of Glucocorticoid receptor

<400> SEQUENCE: 12

Arg Lys Cys Leu Gln Ala Gly Met Asn Leu Glu Ala Arg Lys Thr Lys
1 5 10 15

Lys

<210> SEQ ID NO 13
<211> LENGTH: 17
<212> TYPE: PRT
<213> ORGANISM: Artificial sequence
<220> FEATURE:
<223> OTHER INFORMATION: NLS of Glucocorticoid a receptor

<400> SEQUENCE: 13

Arg Lys Cys Leu Gln Ala Gly Met Asn Leu Glu Ala Arg Lys Thr Lys
1 5 10 15

Lys

<210> SEQ ID NO 14
<211> LENGTH: 17
<212> TYPE: PRT
<213> ORGANISM: Artificial sequence
<220> FEATURE:
<223> OTHER INFORMATION: NLS of Glucocorticoid b receptor

<400> SEQUENCE: 14

Arg Lys Cys Leu Gln Ala Gly Met Asn Leu Glu Ala Arg Lys Thr Lys
1 5 10 15

Lys

<210> SEQ ID NO 15
<211> LENGTH: 17
<212> TYPE: PRT
<213> ORGANISM: Artificial sequence
<220> FEATURE:
<223> OTHER INFORMATION: NLS of Progesterone receptor

<400> SEQUENCE: 15

Arg Lys Cys Cys Gln Ala Gly Met Val Leu Gly Gly Arg Lys Phe Lys
1 5 10 15

Lys

<210> SEQ ID NO 16
<211> LENGTH: 17
<212> TYPE: PRT
<213> ORGANISM: Artificial sequence
<220> FEATURE:
<223> OTHER INFORMATION: NLS of Androgen receptor

<400> SEQUENCE: 16

Arg Lys Cys Tyr Glu Ala Gly Met Thr Leu Gly Ala Arg Lys Leu Lys
1 5 10 15

Lys

<210> SEQ ID NO 17
<211> LENGTH: 17
<212> TYPE: PRT
<213> ORGANISM: Artificial sequence
<220> FEATURE:
<223> OTHER INFORMATION: NLS of p53 protein

<400> SEQUENCE: 17

Arg Arg Cys Phe Glu Val Arg Val Cys Ala Cys Pro Gly Arg Asp Arg
1 5 10 15

Lys

<210> SEQ ID NO 18
<211> LENGTH: 44
<212> TYPE: DNA
<213> ORGANISM: Artificial sequence
<220> FEATURE:
<223> OTHER INFORMATION: 5'Bam-EcMut oligonucleotide primer; see Table 2

<400> SEQUENCE: 18
cgggatccaa aaaaatgtct gctatagaaa atttcgacgc ccat 44

<210> SEQ ID NO 19
<211> LENGTH: 30
<212> TYPE: DNA
<213> ORGANISM: Artificial sequence
<220> FEATURE:
<223> OTHER INFORMATION: 3'Pst-EcMut oligonucleotide primer; see Table 2

<400> SEQUENCE: 19
aactgcagtt attacaccag gctcttcaag 30

<210> SEQ ID NO 20
<211> LENGTH: 77
<212> TYPE: DNA
<213> ORGANISM: Artificial sequence
<220> FEATURE:
<223> OTHER INFORMATION: Bam-NLS-Sma-EcMut oligonucleotide primer; see Table 2

<400> SEQUENCE: 20
cgggatccaa aaaaatggct cctaagaaga agagaaaggt tggaggagga cccgggagtg 60
caatagaaaa tttcgac 77

<210> SEQ ID NO 21
<211> LENGTH: 71
<212> TYPE: DNA
<213> ORGANISM: Artificial sequence
<220> FEATURE:
<223> OTHER INFORMATION: EcoRV-NLS-Sma-EcMut oligonucleotide primer; see Table 2

<400> SEQUENCE: 21
cggatatcat ggctcctaag aagaagagaa aggttggagg aggacccggg agtgcaatag 60
aaaatttcga c 71

<210> SEQ ID NO 22
<211> LENGTH: 31
<212> TYPE: DNA
<213> ORGANISM: Artificial sequence
<220> FEATURE:
<223> OTHER INFORMATION: EcMutL-5'Sma oligonucleotide primer; see Table 2

<400> SEQUENCE: 22
gaattccccg ggccaattca ggtcttaccg c 31

<210> SEQ ID NO 23
<211> LENGTH: 31
<212> TYPE: DNA
<213> ORGANISM: Artificial sequence
<220> FEATURE:
<223> OTHER INFORMATION: EcMutL-3'Pst oligonucleotide primer; see Table 2

<400> SEQUENCE: 23
aaactgcagt catcactcat ctttcagggc t 31

<210> SEQ ID NO 24
<211> LENGTH: 32
<212> TYPE: DNA
<213> ORGANISM: Artificial sequence
<220> FEATURE:
<223> OTHER INFORMATION: MutH-5'BamSfo oligonucleotide primer; see Table 2

<400> SEQUENCE: 24
atcggatccg gcgccatgtc ccaacctcgc cc 32

<210> SEQ ID NO 25
<211> LENGTH: 42
<212> TYPE: DNA
<213> ORGANISM: Artificial sequence
<220> FEATURE:
<223> OTHER INFORMATION: MutH-3'XhoNot oligonucleotide primer; see Table 2

<400> SEQUENCE: 25
atcctcgagc ggccgctcac tactggatca gaaaatgacg gg 42

<210> SEQ ID NO 26
<211> LENGTH: 107
<212> TYPE: DNA
<213> ORGANISM: Artificial sequence
<220> FEATURE:
<223> OTHER INFORMATION: NLS-FLAG-Gly-sense oligonucleotide

<400> SEQUENCE: 26
gatccaaaaa aatggctcct aagaagaaga gaaaggttaa cggtgattac aaggatgatg 60
atgataagcc cgggggtgga ggtggaggtg gaggtggagg tggaggc 107

<210> SEQ ID NO 27
<211> LENGTH: 102
<212> TYPE: DNA
<213> ORGANISM: Artificial sequence
<220> FEATURE:
<223> OTHER INFORMATION: NLS-FLAG-Gly-antisense oligonucleotide

<400> SEQUENCE: 27
gcctccacct ccacctccac ctccacctcc acccccggct tatcatcatc atccttgtaa 60

```
tcaccgttaa cctttctctt cttcttagga gccatttttt tg                   102


<210> SEQ ID NO 28
<211> LENGTH: 2690
<212> TYPE: DNA
<213> ORGANISM: Artificial sequence
<220> FEATURE:
<223> OTHER INFORMATION: NLS-MutS RS codon-optomized for expression in
      crucifers

<400> SEQUENCE: 28

ggatccaaaa caatggctcc taagaagaag aggaaggttg gtggaggtga ttacaaggat     60

gatgatgata agggtggagg tggaggtgga ggtggaggtg gaggtggaat gtctgctatc    120

gagaacttcg atgctcacac ccctatgatg cagcagtacc tcaggctcaa ggctcagcac    180

cctgagatcc tcctcttcta caggatggga gatttctacg agctcttcta cgatgatgct    240

aagagggctt ctcagctcct cgatatctct ctcaccaaga ggggagcttc tgctggagag    300

cctatcccta tggctggaat cccttaccac gctgttgaga actacctcgc taagcttgtt    360

aaccagggag agtctgttgc tatctgcgag cagatcggag atcctgctac ctctaaggga    420

cctgttgaga ggaaggttgt taggatcgtt acccctggaa ccatctctga tgaggctctc    480

ctccaggaga ggcaggataa cctcctcgct gctatctggc aggattctaa gggattcgga    540

tacgctaccc tcgatatctc ttctggaagg ttcaggctct ctgagcctgc tgatagggag    600

accatggctg ctgagctcca gaggaccaac cctgctgagc tcctctacgc tgaggatttc    660

gctgagatgt ctctcatcga gggaaggagg ggactcagga ggaggcctct ctgggagttc    720

gagatcgata ccgctaggca gcagctcaac ctccagttcg gaaccaggga tctcgttgga    780

ttcggagttg agaacgctcc taggggactc tgcgctgctg gatgcctcct ccagtacgct    840

aaggataccc agaggaccac cctccctcac atcaggtcta tcaccatgga gagggagcag    900

gattctatca tcatggatgc tgctaccagg aggaacctcg agatcaccca gaacctcgct    960

ggaggagctg agaacaccct cgcttctgtt ctcgattgca ccgttacccc tatgggatct   1020

aggatgctca agaggtggct ccacatgcct gttagggata ccagggttct cctcgagagg   1080

cagcagacca tcggagctct ccaggatttc accgctggac tccagcctgt tctcaggcag   1140

gttggagatc tcgagagaat cctcgctagg ctcgctctca ggaccgctag gcctagggat   1200

ctcgctagga tgaggcacgc tttccagcag ctccctgagc tcagggctca gctcgagacc   1260

gttgattctg ctcctgttca ggctctcagg gagaagatgg gagagttcgc tgagctcagg   1320

gatctcctcg agagggctat catcgatacc cctcctgttc tcgttaggga tggaggagtt   1380

atcgcttctg gatacaacga ggagctcgat gagtggaggg ctctcgctga tggagctacc   1440

gattacctcg agaggctcga ggttagggag agggagagga ccggactcga taccctcaag   1500

gttggattca acgctgttca cggatactac atccagatct ctaggggaca gtctcacctc   1560

gctcctatca actacatgag gaggcagacc ctcaagaacg ctgagaggta catcatccct   1620

gagctcaagg agtacgagga taaggttctc acctctaagg gaaaggctct cgctctcgag   1680

aagcagctct acgaggagct cttcgatctc ctcctccctc acctcgaggc tctccagcag   1740

tctgcttctg ctctcgctga gctcgatgtt ctcgttaacc tcgctgagag ggcttacacc   1800

ctcaactaca cctgccctac cttcatcgat aagcctggaa tcaggatcac cgagggaagg   1860

caccctgttg ttgagcaggt tctcaacgag cctttcatcg ctaaccctct caacctctct   1920

cctcagagga ggatgctcat catcaccgga cctaacatgg gaggaaagtc tacctacatg   1980
```

aggcagaccg ctctcatcgc tctcatggct tacatcggat cttacgttcc tgctcagaag 2040
gttgagatcg gacctatcga taggatcttc accagggttg gagctgctga tgatctcgct 2100
tctggaaggt ctaccttcat ggttgagatg accgagaccg ctaacatcct ccacaacgct 2160
accgagtact ctctcgttct catggatgag atcggaaggg gaacctctac ctacgatgga 2220
ctctctctcg cttgggcttg cgctgagaac ctcgctaaca agatcaaggc tctcaccctc 2280
ttcgctaccc actacttcga gctcacccag ctccctgaga agatggaggg agttgctaac 2340
gttcacctcg atgctctcga gcacggagat accatcgctt tcatgcactc tgttcaggat 2400
ggagctgctt ctaagtctta cggactcgct gttgctgctc tcgctggagt tcctaaggag 2460
gttatcaaga gggctaggca gaagctcagg gagctcgagt ctatctctcc taacgctgct 2520
gctacccagg ttgatggaac ccagatgtct ctcctctctg ttcctgagga gacctctcct 2580
gctgttgagg ctctcgagaa cctcgatcct gattctctca cccctaggca ggctctcgag 2640
tggatctaca ggctcaagtc tctcgtttaa tgatgagcgg ccgcgaattc 2690

<210> SEQ ID NO 29
<211> LENGTH: 2313
<212> TYPE: DNA
<213> ORGANISM: Artificial sequence
<220> FEATURE:
<223> OTHER INFORMATION: NLS-MutU (MutU from E.coli fused to C-terminal NLS fo VirD2 protein)

<400> SEQUENCE: 29
gccatggacg tttcttacct gctcgacagc cttaatgaca aacagcgcga agcggtggcc 60
gcgccacgca gcaaccttct ggtgctggcg ggcgcgggca gtggtaagac gcgcgtactg 120
gtgcatcgta tcgcctggtt gatgagcgtg gaaaactgct cgccatactc gattatggcg 180
gtgacgttta ccaacaaagc ggcggcggag atgcgtcatc gtatcgggca actgatgggc 240
acgagccagg gcggtatgtg ggtcggcacc ttccacgggc tggcgcaccg tttgctgcgt 300
gcgcaccata tggacgccaa tctgccgcag gatttccaga tcctcgacag tgaagaccag 360
ctacgcctgc ttaagcgtct gatcaaagcc atgaacctcg acgagaagca gtggccgccg 420
cggcaggcaa tgtggtacat caacagccag aaagatgaag gcctgcgtcc gcatcatatt 480
caaagctacg gtaatccggt ggagcagacc tggcagaagg tgtatcaggc gtatcaggaa 540
gcgtgtgacc gcgcgggcct ggtggacttc gccgagctgc tgctgcgcgc tcacgagttg 600
tggcttaaca agccgcatat cctgcaacac taccgcgaac gttttaccaa tatcctggtg 660
gacgaattcc aggataccaa caacattcag tacgcgtgga tccgcctgct ggcgggcgac 720
accggcaaag tgatgatcgt cggtgatgac gaccagtcaa tctacggctg gcgcggggcg 780
caggtggaga atattcagcg tttccttaat gatttccccg gtgccgaaac tattcgtctg 840
gagcaaaact accgctctac cagcaatatt ctgagcgccg ctaacgccct gattgaaaac 900
aataacgggc gtctgggtaa aaaactgtgg accgatggcg cggacggtga gcctatttcc 960
ctctattgcg cttttaacga actcgatgaa gcgcgttttg tggttaaccg catcaaaacc 1020
tggcaggaca acggcggagc gcttgccgag tgcgccattc tctaccgcag caacgcccag 1080
tcgcgggtgc tcgaagaggc gttattgcag gccagtatgc cgtaccgtat ttacggcggg 1140
atgcgcttct tcgaacgcca ggaaatcaaa gatgcgctct cgtatctgcg cctgattgcc 1200
aaccgcaacg acgacgcggc ctttgagcgt gtggtgaata cgccaacgcg gggtattggt 1260
gaccggacgc tggacgtggt acgtcagaca tcgcgcgatc gccagttaac actctggcag 1320
gcatgtcgtg agctgttgca ggaaaaagcc ctcgccgggc gagctgccag cgccttgcag 1380
cgatttatgg aattaatcga cgccttagcg caggaaactg ccgatatgcc gctgcatgta 1440
cagactgacc gggtaattaa agactccggc ctgcgtacca tgtatgagca ggagaagggc 1500
gaaaaaggtc agacgcgtat cgaaaactta gaggaactgg tgacggcaac gcgccagttc 1560
agctacaacg aagaagacga agatttaatg ccgctgcagg cgttcctctc ccatgcggca 1620
ctggaagcag gtgaagggca ggcggatacc tggcaggatg cggtgcagtt gatgacgcta 1680
cactcggcga aaggcctgga gttcccgcag gtgtttatcg ttggtatgga agagggcatg 1740
ttcccaagcc agatgtcgct ggatgaaggc gggcgtctgg aagaagaacg ccgtctggcc 1800
tacgttggcg taacccgcgc gatgcagaaa ctgacgctga cctacgcgga aacccgccgt 1860
ctgtatggta aagaggttta ccatcgcccg tcgcgcttta tcggcgagct gccggaagag 1920
tgtgtggaag aggtgcgcct gcgcgccacg gtaagccgcc cggtcagcca tcagcggatg 1980
ggtacgccga tggtcgagaa cgacagcggc tacaagctcg gccagcgcgt acgccacgct 2040
aagtttggtg aaggcaccat tgtcaatatg gaaggcagcg gtgagcatag ccgtttgcag 2100
gtggcatttc agggccaggg tattaaatgg ctggtggcgg catacgcccg gctggagtcg 2160
gtgggcgccg gtggaggtgg aggtggaggt ggacccgggc tttcaaagcg tccgcgtgaa 2220
gatgatgatg gagaaccgag tgaacgcaaa cgcgagagag atgaggttaa cggtgattac 2280
aaggatgatg atgataagta ataactgcag gat 2313

<210> SEQ ID NO 30
<211> LENGTH: 34
<212> TYPE: DNA
<213> ORGANISM: Artificial sequence
<220> FEATURE:
<223> OTHER INFORMATION: UVR-5'BglNco oligonucleotide for amplifying MutU

<400> SEQUENCE: 30
atcagatctg ccatggacgt ttcttacctg ctcg 34

<210> SEQ ID NO 31
<211> LENGTH: 47
<212> TYPE: DNA
<213> ORGANISM: Artificial sequence
<220> FEATURE:
<223> OTHER INFORMATION: UVR-3'XhoNotSfo oligonucleotide for amplifying MutU

<400> SEQUENCE: 31
atcctcgagg cggccgctta ggcgcccacc gactccagcc gggcgta 47

<210> SEQ ID NO 32
<211> LENGTH: 141
<212> TYPE: DNA
<213> ORGANISM: Artificial sequence
<220> FEATURE:
<223> OTHER INFORMATION: pNML27 sequence encoding eight glycine residues, followed by 22 residues of C-terminal NLS of VirD2, followed by FLAG peptide

<400> SEQUENCE: 32
ggcgccggtg gaggtggagg tggaggtgga cccgggcttt caaagcgtcc gcgtgaagat 60
gatgatggag aaccgagtga acgcaaacgc gagagagatg aggttaacgg tgattacaag 120
gatgatgatg ataagtaata a 141

MODIFYING THE DNA RECOMBINATION POTENTIAL IN EUKARYOTES

The invention relates to methods of modulating the recombinogenic potential and in vivo mutagenesis of eukaryotic cells. The present invention provides methods of modulating the homeologous recombination potential, meiotic homologous recombination potential of eukaryoteic cells, or mitotic homologous recombination potential in vegetative eukaryotic cells, and to organisms produced according to the process.

BACKGROUND OF THE INVENTION

Homologous recombination refers to the exchange of homologous segments anywhere along a length of two DNA nucleotide sequences. In normal mitotic and meiotic cell cycle processes, homologous recombination may occur during spontaneous strand breaks of the DNA in the case of mitotic cells, or it may be catalysed by a specific enzyme such as SPO11 in the case of meiosis. Upon formation of the double-strand breaks, the exposed double-stranded ends are thought to be resected by an exonuclease activity that degrades the DNA to generate single-stranded DNA (ssDNA) ends which have a 3' hydroxyl group. The single-stranded ends may then be acted upon by strand invasion proteins such as RecA homologues. Many of these proteins may be specific to mitotic or meiotic cells, whereas other proteins act in both mitotic and meiotic cells. Strand invasion, pairing of homologous nucleotide sequences and formation of initial crossovers (chiasmata) between the sister chromatids in vegetative cells and non-sister chromatids in meiotic cells is followed by branch migration, DNA replication and strand displacement. Resolution of the crossovers formed between paired chromatids may be enhanced by proteins known as resolvases which have been characterized in a variety of organisms.

Homologous recombination may be employed to genetically engineer DNA sequences in an organism and provides a basis for performing specific targeted alterations in the genome of an organism. Targeted homologous recombination has been proposed to create transgenic organisms such as plants and animals. A transgenic organism is one that contains a copy of a gene or nucleotide sequence from another species. Homologous recombination permits the targeted change to be incorporated into homologous sites in the chromosomes of the organism so that the change may be passed on to the organism's progeny.

There are a variety of references that disclose methods of modulating homologous recombination in an organism. For example, WO 02/22811 discloses methods of modifying the level or functional activity of factors such as enzymes or other catalytic proteins to modify the frequency of meiotic homologous recombination in a eukaryotic cell. The invention provides methods of increasing meiotic homologous recombination in a eukaryote by transforming a cell with an activator of homologous recombination or inhibiting meiotic homologous recombination by transforming a cell with an inhibitor of meiotic recombination. While the patent application discloses several methods for modulating homologous recombination, there is a need in the art for alternate methods of modulating homologous and homeologous recombination in an organism.

PCT applications WO 01/62945, WO 01/61012 and U.S. Pat. No. 6,146,894 to Nicolaides et al., disclose methods for generating hypermutable yeast, plants and mammalian cells, respectively. The references teach expressing a dominant negative allele of an endogenous mismatch repair gene in a cell to generate hypermutable cells and organisms. By introduction of the dominant negative alleles, new cell lines and organism varieties can be prepared more efficiently than by relying on the natural rate of mutation. Specifically, WO 01/61012 discloses transforming a cell or transgenic plant with a dominant negative allele encoding a protein which is part of a mismatch repair complex such as MutS or MutL homologues of the bacterial, yeast, fungal, insect, plant or mammalian genes.

Although the patents and applications suggest that the disclosed methods result in hypermutable cells, a major problem with such systems is that it may take an excessively long time for the hypermutable cells to recombine to give a specific desired mutation. Further there is no suggestion in any of the references of a method of increasing or decreasing homeologous recombination during inter or intraspecies breeding. Thus, there is a need in the art for novel methods of increasing or decreasing the recombinogenic potential of cells, for example during meiosis. There is a need in the art for novel methods of increasing or decreasing homeologous recombination during inter or intraspecies breeding. Further there is a need for alternate sources of mismatch repair proteins, for example, prokaryotic proteins including MutS, for use in in vivo mutagenesis It is an object of the present invention to overcome disadvantages of the prior art.

The above object is met by a combination of the features of the main claims. The sub claims disclose further advantageous embodiments of the invention.

SUMMARY OF THE INVENTION

The invention relates to methods of modulating the recombinogenic potential and in vivo mutagenesis of eukaryotic cells. The present invention provides methods of modulating the homeologous recombination potential, meiotic homologous recombination potential of eukaryoteic cells, or mitotic homologous recombination potential in vegetative eukaryotic cells, and to organisms produced according to the process.

According to the present invention there is provided a method of increasing the recombination potential of a eukaryotic cell comprising the steps of a) providing the eukaryotic cell with a nucleotide sequence capable of expressing a wild-type prokaryotic MutS, MutL, MutH, MutU protein or a combination thereof, and;
b) expressing the wild-type prokaryotic MutS, MutL, MutH, MutU protein or a combination thereof.

The recombination potential may comprise homeologous recombination potential, meiotic homologous recombination potential, homologous recombination potential in a vegetative cell, or any combination thereof.

Also provided by the present invention is a method of increasing homeologous recombination between two eukaryotic organisms comprising the steps of a) providing a first eukaryotic organism with a nucleotide sequence capable of expressing a wild-type prokaryotic MutS, MutL, MutH, MutU protein or a combination thereof within a germ cell,
b) mating the first organism with a second organism to produce a first progeny, and
c) mating the first progeny, and obtaining a second progeny comprising a hybrid chromosome.

Preferably, the first organism and second organism are closely related. Further the eukaryotic cell or organism may be any animal, plant or yeast. In an embodiment of the present invention, the eukaryotic cell or organism is a plant, animal, or yeast or a cell derived therefrom. Plant cells may be monocots or dicots, for example, selected from the group consisting of *Brassica, Sinapis, Triticum, Zea, Hordeum, Avena, Oryza, Glycine, Linum, Medicago, Lens, Pisum, Cicer, Solanum, Lycopersicon, Secale, Populus, Gossypium, Raphanus, Triflorium, Phaseolus, Bromus, Phleum, Agropyron, Helianthus, Beta, Malus, Prunus, Cucurbita, Phoenix, Abies, Acer, Quercus, Olea, Allium, Washingtonia, Papaver, Rosa, Carthamus, Vicia, Fragaria, Lotus, Onobrychis, Trigonella, Vigna, Citrus, Geranium, Daucus, Arabidopsis, Atropa, Capsicum, Picea, Pyrus, Pinus, Hyoscyamus, Nicotiana, Arachus, Asparagus, Heterocatlis, Nemesia, Pelargonium, Panicum, Penniserum, Ranunculus, Senecio, Salpiglossis, Cucarnis, Browallia, Cedrus, Lolium, Sorghum, Datura, Petunia, Digitalis, Majorana, Cichorium, Lactuca, Antirrhinum*, and *Manihot.*

The method of the present invention as defined above also contemplates embodiments wherein wild-type prokaryotic MutS, MutL, MutH, MutU protein or a combination thereof, is capable of maintaining mismatches between dissimilar nucleotide sequences but exhibits diminished or no mismatch repair activity in the eukaryotic cell. The MutS protein may be *E. coli* MutS protein. Further, the MutS protein may further comprise a NLS sequence.

Also, the invention provides a method as defined above wherein the nucleotide sequence further comprises one or more regulatory regions for controlling transcription and translation of the MutS protein. In an embodiment of the present invention, the one or more regulatory regions may comprise an S-phase promoter, a pre-meiotic promoter, a meiotic promoter or a preferentially meiotic promoter.

Further, the present invention provides a method as defined above and further comprising the step of expressing one or more additional factors that promote homologous recombination. The one or more additional factors may be selected from the group consisting of factors that promote double strand breaks in DNA, factors involved in resection of nucleotide strands, factors involved in strand invasion, resolvases or chromatin remodeling proteins. Such factors may be selected from the group consisting of SPO11, MRE11, RAD50, XRS2/NBS1, RecA homologues, DMC1, RAD51, RAD 52, RAD54, RAD55, RAD57, TIDI, MSH4, MSH5, historic acetylases, synaptonemal complex proteins, WRN, BLM, SGS1 and any combination thereof.

According to the present invention there is also provided a method of increasing the recombination potential of a eukaryotic cell comprising the steps of a) providing the eukaryotic cell with a nucleotide sequence capable of expressing a wild-type prokaryotic NLS-MutS, NLS-MutL, NLS-MutH, NLS-MutU protein or a combination thereof, and;

b) expressing the wild-type prokaryotic NLS-MutS, NLS-MutL, NLS-MutH, NLS-MutU protein or a combination thereof.

The present invention also provides a method of decreasing the homeologous recombination potential of a eukaryotic cell comprising the steps of a) providing the cell with a genetic construct capable of overexpressing MSH2, MutS, MutL, MutH, MutU, a combination of MutS, Muts, MutH, MutU, or an alternate endogenous mismatch repair protein, and;

b) expressing the MSH2, MutS, MutL, MutH, MutU, a combination of MutS, Muts, MutH, MutU, or alternate endogenous mismatch repair protein, in the cell.

Further, the present invention provides a method of decreasing homeologous recombination between two eukaryotic organisms comprising the steps of a) providing a first eukaryotic organism with a nucleotide sequence capable of overexpressing MSH2, MutS, MutL, MutH, MutU, a combination of MutS, Muts, MutH, MutU, or alternate endogenous mismatch repair protein in a germ cell, and;

b) mating the first organism with a second organism to produce progeny.

Also according to the present invention, there is provided a method of increasing homologous recombination between dissimilar nucleotide sequences in a eukaryote, comprising the steps of:

a) transforming the eukaryote with a first nucleotide sequence capable of expressing a MutS, MutL, MutH, MutU protein, or a combination thereof, and a second nucleotide sequence comprising a nucleotide targeting sequence, and;

b) expressing the MutS, MutL, MutH, MutU protein, or a combination thereof, in the presence of the nucleotide targeting sequence.

The method of the present invention as defined above also provides a method of increasing interspecies or intraspecies homeologous recombination during breeding of two eukaryotic organisms.

There is a need in the art for a technology employing prokaryotic mismatch repair (MMR) proteins to manipulate mutation frequency and/or homeologous recombination frequency in eukaryotic cells. Manipulation of endogenous eukaryotic MMR proteins to modify mutation frequency, homeologous recombination frequency, or both, is not a desirable approach because altering the activity of these proteins can induce cellular apoptosis. Therefore manipulating the activity of endogenous eukaryotic MMR proteins can lead to decreased viability, vigour and productivity of host eukaryotic systems. In contrast, due to the evolutionary distance between prokaryotic and eukaryotic MMR protein, prokaryotic MMR proteins may be expressed in eukaryotic host cells without initiating cellular apoptosis. Therefore the methods of the present invention may be used for genome manipulation through modulation of mutation frequency and homeologous recombination frequency.

MutS, MutL, MutH, MutU, in addition to associated exonucleases, from *E. coli* may also be used to manipulate endogenous eukaryotic MMR processes. Similarly, MutS, MutL, MutH, MutU, in addition to associated exonucleases, obtained from other prokaryotes may be used to manipulate endogenous eukaryotic MMR processes. Non-limiting examples of prokaryotes from which MutS, MutL, MutH, MutU, may be obtained include: *Salmonella typhimurium; Haemophilus influenzae; Azotobacter vinelandii; Neisseria gonorrhoeae; Synechocyslis* spp.; *Treponema pallidum; Borelia burgdorferi; Streptococcus pneumoniae; Streptococcus pyogenes; Bacillus subtilis; Thermus thermophilus; Thermus aquaticus; Deinococcus radiodurans; Thermotoga maritime; Aquifex aeolicus; Aquifex pyrophilus; Chlamydia trachomatis*; and *Helicobacter pylori.*

Additionally, MutS, MutL, MutH or MutU may be modified to have improved properties for affecting the activity of endogenous eukaryotic MMR processes. Such properties may include enhanced affinity for mismatches and/or increased stability when bound to mismatches. Modified MutS, MutL, MutH or MutU proteins may be developed by exchanging and/or combining portions of these proteins from the various prokaryotic species listed above. Alternatively, in vitro evolution techniques like gene shuffling may be applied to obtain new prokaryotic MMR proteins with beneficial properties for affecting the activity of endogenous eukaryotic MMR processes.

There is a need in the art for improved methods for gene targeting in eukaryotic systems. The efficiency of gene targeting is increased in MMR-deficient eukaryotic cells, but reliance on MMR-mutants to decrease MMR activity can be detrimental to the eukaryotic system due to increased mutation frequency and cellular apoptosis (Zhang, H, Richards, B, Wilson, T, Lloyd, M, Cranston, A, Thorburn, A, Fishel, R, Meuth, M: Apoptosis induced by overexpression of hMSH2 or hMLH1. Cancer Res. 59: 3021-3027, 1999) leading to decreased viability, vigour and productivity. The method disclosed in the present invention, to suppress endogenous eukaryotic MMR activity using prokaryotic MMR proteins, is therefore a valuable discovery for gene targeting applications. By linking the prokaryotic MMR genes to regulatable or transiently expressed promoters, or by breeding out cassettes expressing these genes after the desired genetic events have been accomplished, then the mutation load on the host genome may be minimized. However, while the prokaryotic MMR proteins are being expressed, the genome of the host eukaryotic cells may be more efficiently manipulated by gene targeting.

This summary does not necessarily describe all necessary features of the invention but that the invention may also reside in a sub-combination of the described features.

BRIEF DESCRIPTION OF THE DRAWING

These and other features of the invention will become more apparent from the following description in which reference is made to the appended drawings wherein:

FIG. 1 shows two non-limiting representative embodiments of a nucleotide targeting sequence hybridized to a genomic nucleotide sequence.

FIG. 2 shows nucleotide sequences of NLS-MutS (FIG. 2A; SEQ ID NO:1), NLS-MutL (FIG. 2B; SEQ ID NO:2), NLS-MutH (FIG. 2C; SEQ ID NO:3), NLS-MutU, comprising a fusion with a C-terminal NLS (FIG. 2D, SEQ ID NO:28) and NLS-MutS RS, that has been codon optimized for expression in Crucifiers (FIG. 2E, SEQ ID NO:27).

DESCRIPTION OF PREFERRED EMBODIMENT

Figure 1A:
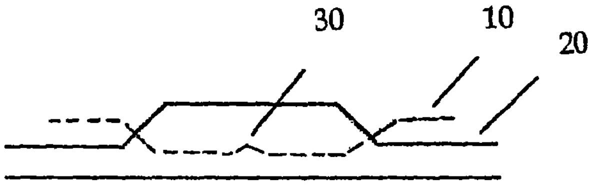
FIG. 1A depicts a nucleotide targeting sequence hybridized to the complementary copy of a genomic nucleotide. The nucleotide targeting sequence comprises one nucleotide mismatch with the genomic nucleotide sequence.

The invention relates to methods of modulating the recombinogenic potential and in vivo mutagenesis of eukaryotic cells. The present invention provides methods of modulating the homeologous recombination potential, meiotic homologous recombination potential of eukaryoteic cells, or mitotic homologous recombination potential in vegetative eukaryotic cells, and to organisms produced according to the process.

The following description is of a preferred embodiment by way of example only and without limitation to the combination of features necessary for carrying the invention into effect.

The present invention provides methods of enhancing in vivo mutagenesis or homeologous recombination in a eukaryote. The method of enhancing in vivo mutagenesis generally involves transforming a eukaryote with a nucleotide sequence capable of expressing a wild-type prokaryotic protein that is involved in the process of mismatch repair, for example but not limited to prokaryotic MutS, MutL, MutH, MutU protein, or a combination thereof, or a modified MutS, MutL, MutH, MutU protein, or a combination thereof, and expressing the protein.

The method of increasing homeologous recombination between two eukaryotic organisms involves providing a first eukaryotic organism with a nucleotide sequence capable of expressing a wild-type prokaryotic protein that is involved in mismatch repair, for example, but not limited to prokaryotic MutS, MutL, MutH, MutU protein, or a combination thereof, or a modified MutS, MutL, MutH, MutU protein, or a combination thereof, within a germ cell, and mating the first organism with a second organism to produce progeny.

Expression of a wild-type prokaryotic MutS, MutL, MutH, MutU protein, or a combination thereof, in a eukaryotic cell may increase the homeologous recombination potential, meiotic homologous recombination potential or mitotic homologous recombination potential of the cell. For example, but not to be considered limiting, a germ cell comprising the MutS, MutL, MutH, MutU protein, or a combination thereof, may exhibit increased homeologous recombination when mated with a second germ cell to produce progeny. The genome of the progeny may comprise a greater number of genetic variants compared to progeny produced in the absence of the MutS, MutL, MutH, or MutU protein, or a combination thereof. Similarly, cells comprising MutS, MutL, MutH, MutU protein, or a combination thereof, that undergo meiosis may exhibit a greater frequency of non-sister chromatid exchange than do cells which lack the MutS, MutL, MutH or MutU protein, or a combination thereof. Further, somatic cells may exhibit increased homologous recombination of sister chromatids in the presence of the MutS, MutL, MutH, MutU protein, or a combination thereof, compared to cells that lack the protein.

By the term "prokaryotic wild-type MutS protein" or "MutS protein", "MutL protein", "MutH protein" or "MutU protein", it is meant any wild-type MutS, MutL, MutH or MutU protein from a prokaryotic organism. Preferably, the MutS, MutL, MutH or MutU protein is capable of binding to nucleotide mismatch regions in DNA, but exhibits diminished or no mismatch repair activity compared to the natural endogenous mismatch repair systems of the host eukaryote, such as, but not limited to MSH2 proteins, or the like. Examples of organisms from which these proteins may be obtained, which are not to be considered limiting in any manner, include *Salmonella typhimurium; Haemophilus influenzae; Azotobacter vinelandii; Neisseria gonorrhoeae; Synechocystis* spp.; *Treponema pallidum; Borelia burgdorferi; Streptococcus pneumoniae; Streptococcus pyogenes; Bacillus subtilis; Thermus thermophiles; Thermus aquaticus; Deinococcus radiodurans; Thermotoga maritime; Aquifex aeolicus; Aquifex pyrophilus; Chlamydia trachomatis*; and *Helicobacter pylori*. Modified, or derivatives of MutS, MutL, MutH or MutU may also be used. Such derivatives include NLS-MutS, NLS-MutL, NLS-MutU, or NLS-MutH or mutant MutS, MutL, MutH or MutU protein, for example but not limited to $MutS^{501}$, or $NLS\text{-}MutS^{501}$. Non-limiting examples of nucleotide sequences encoding NLS-MutS, NLS-MutL, NLS-MutH, NLS-MutU or NLS-MutS RS protein are found in FIGS. 2A-E, and SEQ ID NO's: 1-3, 28 and 27, respectively. NLS-MutS RS is an NLS-MutS sequence that is codon optimized for expression in crucifers.

Variants of MutS, MutL, MutH or MutU proteins may also be used as described herein. Variants include proteins that exhibit altered affinity to mismatches and that may be obtained from a variety of sources, for example but not limited to an archaebacterial source. Such variant proteins may be prepared by mixing wild type genes from different species in an in vitro recombination system (e.g. Maxygen). Furthermore, the nucleotide sequence encoding MutS, MutL, MutU or MutH maybe modified to optimize the codon usage within the eukaryotic host that the protein is to be expressed. Appropriate codons may be identified using specifies-specific codon tables (e.g. www.kazusa.or.jp/codon/). Methods to determine codon optimization are well known in the art.

By "codon optimization" it is meant the selection of appropriate DNA nucleotides for use within a structural gene or fragment thereof that approaches codon usage within a desired eukaryotic host. Therefore, an optimized gene or nucleic acid sequence refers to a gene in which the nucleotide sequence of a native or naturally occurring gene has been modified in order to utilize statistically-preferred or statistically-favored codons within a desired eukaryotic host. Any method may be used to determine a nucleotide sequence that favours host-specific expression. The nucleotide sequence typically is examined at the DNA level and the coding region optimized for expression in plants determined using any suitable procedure, for example as described in Sardana et al. (1996, Plant Cell Reports 15:677-681). A non-limiting examples example of a protein that has been codon optimized for expression in crucifers is NLS-MutS RS (FIG. 2D; SEQ ID NO:27 NO:28).

Another example of a method of codon optimization is based on the direct use, without performing any extra statistical calculations, of codon optimization tables such as those provided on-line at the Codon Usage Database through the NIAS (National Institute of Agrobiological Sciences) DNA bank in Japan (http://www.kazusa.or.jp/codon/). The Codon Usage Database contains codon usage tables for a number of different species, with each codon usage table having been statistically determined based on the data present in Genbank. A table of codon usage from highly expressed genes of dicotyledonous plants may be compiled using the data of Murray et al. (1989, Nuc Acids Res. 17:477-498).

The wild-type prokaryotic MutS, MutL, MutH, MutU protein, or a combination thereof, may further comprise a nuclear localization signal sequence (NLS) to produce a modified MutS, MutL, MutH, MutU protein. The use of an NLS to produce derivatives of MutS, MutL, MutU or MutH may promote targeting of the modified protein to the nuclear compartment. In an embodiment of the present invention that is not to be considered limiting in any manner, the prokaryotic wild-type MutS protein is *E. coli* MutS or *E. coli* MutS comprising a NLS (NLS-MutS). Additionally, derivatives of MutL, MutU and MutH proteins comprising a NLS (NLS-MutL, NLS-MutU and NLS-MutH), may also be used as described herein.

Nuclear localization signals (NLS) that may be employed in the present invention include, but are not limited to the NLS from the simian virus 40 large T-antigen (van der Krol and Chua, 1991, Plant Cell 3:667-6751 and the NLS signals shown in Table 1. Alternatively, any of the MutS, MutL, or MutH proteins may be fused to a C-terminal nuclear localization sequence. An example of a C-terminal NLS is that from the VirD2 protein which is functional in animal, yeast and plant cells (for example, Relic, B, Andjelkovic, M, Rossi, L, Nagamine, Y, Hohn, B: Interaction of the DNA modifying proteins VirD1 and VirD2 of *Agrobacterium tumefaciens*: analysis by subcellular localization in mammalian cells. Proc Natl Acad Sci USA 95: 9105-9110, 1998; Tinland, B, Koukolikova-Nicola, Z, Hall, M N, Hohn, B: The T-DNA-linked VirD2 protein contains two distinct functional nuclear localization signals. Proc Natl Acad Sci USA 89: 7442-7446, 1992).

TABLE 1 nuclear localization signals

| Nuclear Protein | Organism | NLS | Ref | SEQ ID NO: |
|---|---|---|---|---|
| AGAMOUS | A | RienttnrqvtfcKRR | 1 | 4 |
| TGA-1A | T | RRlaqnreaaRKsRIRKK | 2 | 5 |
| TGA-1B | T | KKRaRlvrnresaqlsRqRKK | 2 | 6 |
| O2 NLS B | Mz | RKRKesnresaRRsRyRK | 3 | 7 |
| NIa | V | KKnqkhklkm-32aa-KRK | 4 | 8 |
| Nucleoplasmin | X | KRpaatkkagqaKKKKI | 5 | 9 |
| NO38 | X | KRiapdsaskvpRKKtR | 5 | 10 |
| N1/N2 | X | KRKteeesplKdKdaKK | 5 | 11 |
| Glucocorticoid | | | | |
| receptor | M, R | RKclqagmnleaRKtKK | 5 | 12 |
| α receptor | H | RKclqagmnleaRKtKK | 5 | 13 |
| β receptor | H | RKclqagmnleaRKtKK | 5 | 14 |
| Progesterone receptor | C, H, Ra | RKccqagmvlggRKfKK | 5 | 15 |

TABLE 1-continued

| nuclear localization signals | | | | |
|---|---|---|---|---|
| Nuclear Protein | Organism | NLS | Ref | SEQ ID NO: |
| Androgen receptor | H | RKcyeagmtlgaRKIKK | 5 | 16 |
| p53 | C | RRcfevrvcacpgRdRK | 5 | 17 |

*A, *Arabidopsis*; X, *Xenopus*; M, mouse; R, rat; Ra, rabbit; H, human; C, chicken; T, tobacco; Mz, maize; V, potyvirus.

References:

1 Yanovsky et al., 1990, Nature, 346: 35-39

2 van der Krol and Chua, 1991, Plant Cell, 3: 667-675

3 Varagona et al., 1992, Plant Cell, 4: 1213-1227

4 Carrington et al., 1991, Plant Cell, 3: 953-962

5 Robbins et al., 1991, Cell, 64: 615-623.

By the term "homeologous recombination" it is meant genetic recombination between chromosomes or chromosome segments that have a close evolutionary relationship, and as a result have related DNA sequences, but that are not necessarily members of the same homologous pair of chromosomes. Homeologous chromosomes may comprise, but are not limited to equivalent chromosomes from related species.

By the term "recombination potential" it is meant the ability of a eukaryotic cell or gamete from the combination of two germ cells to undergo genetic recombination. For example, "homeologous recombination potential" includes, but is not limited to, the propensity for non-sister chromatids between organisms to undergo recombination. Similarly, "meiotic homologous recombination potential" refers, but is not limited to, the propensity for a eukaryotic cell to undergo recombination during meiosis, for example, but not limited to, recombination of non-sister chromatids. The term "mitotic homologous recombination potential" refers but is not limited to the propensity for a eukaryotic cell to undergo recombination during the mitotic cell cycle, for example, but not limited to, recombination of sister chromatids, or with an exogenously supplied DNA sequence that exhibits homology to a chromosomal locus.

By the term "eukaryote" or "eukaryotic cell", it is meant any non-human eukaryotic organism or cell derived therefrom, for example, but not limited to plants, animals, insects, or yeasts. The eukaryotic host may be transformed for example, with the nucleic sequence encoding MutS, MutL, MutH, MutU protein, or a combination thereof. In an embodiment of the present invention which is not meant to be limiting, the eukaryote is preferably a plant, more preferably a higher plant. Any monocot or dicot plant is contemplated by the present invention. Preferably the plant is a species from the genera *Brassica, Sinapis, Triticum, Zea, Hordeum, Avena, Oryza, Glycine, Linum, Medicago, Lens, Pisum, Cicer, Solanum, Lycopersicon, Secale, Populus, Gossypium, Raphanus, Triflorium, Phaseolus, Bromus, Phleum, Agropyron, Helianthus, Beta, Malus, Prunus, Cucurbita, Phoenix, Abies, Acer, Quercus, Olea, Allium, Washingtonia, Papaver, Rosa, Carthamus, Vicia, Fragaria, Lotus, Onobrychis, Trigonella, Vigna, Citrus, Geranium, Daucus, Arabidopsis, Atropa, Capsicum, Picea, Pyrus, Pinus, Hyoscyamus, Nicotiana, Arachus, Asparagus, Heterocatlis, Nemesia, Pelargonium, Panicum, Penniserum, Ranunculus, Senecio, Salpiglossis, Cucarnis, Browallia, Cedrus, Loltum, Sorghum, Datura, Petunia, Digitalis, Majorana, Cichorium, Lactuca, Antirrhinum*, and *Manihot.*

In an embodiment of the present invention, the nucleotide sequence capable of expressing MutS, MutL MutU or MutH protein, or a combination thereof, may further comprise one or more regulatory regions. By "regulatory region" or "regulatory element" it is meant a portion of nucleic acid typically, but not always, upstream of the protein coding region of a gene, which may be comprised of either DNA or RNA, or both DNA and RNA. When a regulatory region is active and in operative association with a gene, this may result in expression of the gene. A regulatory element may be capable of mediating organ specificity, or controlling developmental or temporal gene activation. A "regulatory region" includes promoter elements, core promoter elements exhibiting a basal promoter activity, elements that are inducible in response to an external, developmental or physiological stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element comprises a basal promoter element, responsible for the initiation of transcription, as well as other regulatory elements (as listed above) that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well.

In an embodiment of the present invention, the expression of MutS, MutL, MutH, MutU protein, or a combination thereof, or derivatives of MutS, MutL, MutH, MutU protein, or a combination thereof, for example comprising an NLS, may be meiosis-specific or preferentially-meiosis specific. A variety of regulatory sequences that are meiosis-specific or preferentially-meiosis specific are known in the art and any of such regulatory sequences may be employed by the present invention. For example, the regulatory sequence may comprise a meiosis-specific or preferentially-meiosis specific promoter (i.e. promoters that are expressed exclusively or primarily during meiosis, respectively) operably linked to a nucleotide sequence encoding MutS, MutL, MutU or MutH protein, or a derivative thereof. Examples of such promoters may be found in the meiotic recombination factor genes described herein, including homologues obtainable from species from yeast to plants and animals.

Expression of proteins during the pre-meiotic S-phase (e.g. B. Lee and A. Amon. 2002. Meiosis: how to create a specialized cell cycle. Current Opinion in Cell Biology. 13:770-777; S. L. Forsburg. 2002. Only connect: linking meiotic DNA replication to chromosome dynamics. Molecular Cell. 9:703-711) may also be desired. By regulating MMR disruption as a result of expressing MutS, MutL, MutH, MutU, or a combination thereof, to only occur in the pre-meiotic S-phase, only the gametes will become mutagenised and somatic tissues may remain pristine.

Specific examples of promoters tested to be meiosis-specific include, but are not limited to promoters from DMC1 (Klimyuk et al., 1997) and MSH4 (Ross et al., 1994). Additional promoters may be obtained from genes that are expressed in meiosis-specific manner (for example, see Kobayashi et al., 1994), genes that are induced during meiosis (Chu et al., 1998), or genes expressed in the pre-meitoic S-phase (B. Lee and A. Amon. 2002, Current Opinion in Cell Biology. 13:770-777; S. L. Forsburg. 2002, Molecular Cell. 9:703-711). Preferentially-meiotic promoters may include, but are not limited to promoters active in vegetative cells or germ-line cells which lead to meiotic cells, wherein expression is mediated sufficiently close to the onset of meiosis. Further, new promoters may be engineered to be meiosis-specific or preferentially meiotic, such as promoters that are initially active in both mitotic and meiotic cells. Such promoters may be modified by deletion or inactivation of mitotic expression elements so that their expression becomes preferential or specific during meiosis.

Further, certain transcription factors, for example, but not limited to NDT80 and promoter consensus sequences, for example, but not limited to URS1 are thought to be responsible for meiosis-specific expression (Chu et al., 1998). Constitutive or vegetatively active promoters may be converted to meiosis-specific or preferentially-meiotic promoters by modifying the promoter to contain the recognition sequences for meiosis-specific transcription factors and to be active only when the promoter binds these transcription factors.

Bipartite promoters may also be used to provide meiosis-specific expression. Bipartite systems typically consist of 1) a minimal promoter containing a recognition sequence for 2) a specific transcription factor. The bipartite promoter is usually inactive unless it is bound by the transcription factor. The nucleotide sequence encoding MutS, MutL, MutU or MutH may be placed behind the minimal promoter so that it is not expressed, and the transcription factor may be linked to a meiosis-specific promoter. The transcription factor may be a naturally occurring protein or a hybrid protein composed of a DNA-binding domain and a transcription-activating domain. Because the activity of the minimal promoter is dependent upon binding of the transcription factor, the operably-linked coding sequence will not be expressed in vegetative cells. In meiotic cells, the meiosis-specific promoter will be turned on facilitating expression of the transcription factor. The transcription factor will act in trans and bind to the DNA recognition sequence in the minimal promoter via the cognate DNA-binding domain. The activation domain of the transcription factor will then be in the appropriate context to aid recruitment of RNA polymerase and other components of the transcription machinery. This will cause transcription of the nucleotide sequence encoding MutS, MutL, MutU or MutH protein. With this bipartite system, the nucleotide sequence encoding MutS, MutL, MutU or MutH will only be expressed in cells entering or undergoing meiosis since the necessary transcription factor is linked to a meiosis-specific promoter and will only be expressed at the desired developmental stage (i.e. MutS, MutL, MutU or MutH protein will be expressed in a spatial and temporal pattern mirroring the meiosis-specific promoter expressing the transcription factor). Use of a bipartite system may have the advantage that if expression of the MutS, MutL, MutU or MutH protein is no longer required in a particular plant or animal line, then the transcription factor may be bred out, so that without the transcription factor present, the MutS, MutL, MutU or MutH protein is no longer expressed in the plant or animal line. Further, if expression of MutS, MutL, MutU or MutH protein is desired at a later stage, the promoter::transcription factor locus may be bred back into the line. In addition, the bipartite system may be used to modulate the level of expression of the MutS, MutL, MutU or MutH protein.

Minimal promoter elements in bipartite promoters may include, for example, but are not limited to:

1) truncated CaMV 35S (nucleotides −59 to +48 relative to the transcription start site) (Guyer et al., 1998);

2) DNA recognition sequences: *E. coli* lac operator (Moore et al., 1998; Labow et al., 1990), yeast GAL4 upstream activator sequence (Guyer et al., 1998); TATA BOX, transcription start site, and may also include a ribosome recruitment sequence.

Bipartite promoters may also include transcription factors such as: the yeast GAL4 DNA-binding domain fused to maize Cl transcription activator domain (Guyer et al., 1998); *E. coli* lac repressor fused to yeast GAL4 transcription activator domain (Moore et al., 1998); or the *E. coli* lac repressor fused to herpes virus VP16 transcription activator domain (Labow et al., 1990).

Meiosis-specific promoters may be used directly to express MutS, MutL, MutU or MutH protein. However, some meiosis-specific promoters may promote transcription at too low of a level (i.e. weakly expressed) or at too high of a level (i.e. strongly expressed) to achieve the desired effect on homeologous or homologous recombination frequency. Therefore, for example, but not to be considered limiting, a weak meiosis-specific promoter may be used to express a transcription factor which can promote a high level of MutS, MutL, MutU or MutH expression when it binds to a minimal promoter adjacent to the nucleotide sequence encoding MutS, MutL, MutU or MutH. Thus, while MutS, MutL, MutU or MutH might be expressed at a low level if it was directly fused to the meiosis-specific promoter, this promoter can indirectly facilitate high level expression of the nucleotide sequence expressing MutS, MutL, MutU or MutH by expressing a very active transcription factor. The transcription factor may be present at low levels but because it may be very effective at activating transcription of the minimal promoter fused to the nucleotide sequence encoding MutS, MutL, MutU or MutH, a higher level of MutS, MutL, MutU or MutH expression may be achieved than if the nucleotide sequence encoding MutSm MutL, MutU, or MutH was directly fused to the weak meiosis-specific promoter. In addition, the transcription factor may also be engineered so that its mRNA transcript is more stable or is more readily translated, or that the protein itself is more stable. Conversely, if the meiosis-specific promoter is too strong for a desired application, it may be used to express a transcription factor with low ability to promote transcription at the minimal promoter adjacent to the target gene.

In an alternative aspect of the invention, inducible promoters may be provided. The nucleotide sequence encoding a MutS, MutL, MutH, or MutU protein may be cloned behind an inducible or repressible promoter. The promoter may then be induced (or de-repressed) by appropriate external treatment of the organism when organismal development proceeds to a point when meiosis is initiated. Regulation of such promoters may be mediated by environmental conditions such as heat shock (Ainley et al., 1990), or chemical stimulus. Examples of chemically regulatable promoters active in plants and animals include, but are not limited to the ethanol, ecdysone, dexamethasone, tetracycline and copper systems (Montney et al., 1999; Bohner et al., 1999; Gatz et al., 1991; Weinmann et al., 1994; Mett et al., 1996).

In alternative embodiments, a meiosis-specific promoter may be used to express a heterologous RNA-polymerase which recognizes specific sequences not naturally present in the eukaryotic cell. For example, T7 RNA Polymerase may be used in eukaryotes to specifically promote transcription of a target gene linked to the T7 RNA Pol recruitment DNA sequence (Benton et al., 1990). A nucleotide sequence encoding, for example, but not limited to, a MutS protein may be operatively linked to a T7 RNA Pol recruitment sequence. Nucleotide sequences affecting homologous recombination may then be regulated by the expression of T7 RNA Polymerase.

The present invention provides a method using prokaryotic mismatch repair (MMR) proteins to manipulate mutation frequency and/or homeologous recombination frequency in eukaryotic cells. Manipulation of endogenous eukaryotic MMR proteins to modify mutation frequency, homeologous recombination frequency, or both, is not a desirable approach because altering the activity of these proteins can induce cellular apoptosis (Zhang, H, Richards, B, Wilson, T, Lloyd, M, Cranston, A, Thorburn, A, Fishel, R, Meuth, M: Apoptosis induced by overexpression of hMSH2 or hMLH1. Cancer Res. 59: 3021-3027, 1999). Therefore manipulating the activity of endogenous eukaryotic MMR proteins can lead to decreased viability, vigour and productivity of host eukaryotic systems. In contrast, due to the evolutionary distance between prokaryotic and eukaryotic MMR protein (Eisen, J A: A phylogenomic study of the MutS family of proteins. Nucleic Acids Res. 26: 4291-4300, 1998; Culligan, K M, Meyer-Gauen, G, Lyons-Weiler, J, Hays, J B: Evolutionary origin, diversification and specialization of eukaryotic MutS homolog mismatch repair proteins. Nucleic Acids Res 28: 463-471, 2000), prokaryotic MMR proteins may be expressed in eukaryotic host cells without initiating cellular apoptosis. Therefore the method provides an important alternative for genome manipulation through modulation of mutation frequency and homeologous recombination frequency.

MutS, MutL, MutH, or MutU, in addition to associated exonucleases, from *E. coli* may also be used to manipulate endogenous eukaryotic MMR processes. Similarly, MutS, MutL, MutH, or MutU, in addition to associated exonucleases, obtained from other prokaryotes may be used to manipulate endogenous eukaryotic MMR processes. Non-limiting examples of prokaryotes from which MutS, MutL, MutH, or MutU, may be obtained include *Salmonella typhimurium; Haemophilus influenzae; Azotobacter vinelandii; Neisseria gonorrhoeae; Synechocystis* spp.; *Treponema pallidum; Borelia burgdorferi; Streptococcus pneumoniae; Streptococcus pyogenes; Bacillus subtilis; Thermus thermophilus; Thermus aquaticus; Deinococcus radiodurans; Thermotoga maritime; Aquifex aeolicus; Aquifex pyrophilus; Chlamydia trachomatis*; and *Helicobacter pylori.*

Additionally, MutS, MutL, MutH or MutU may be modified to have improved properties for affecting the activity of endogenous eukaryotic MMR processes. Such properties may include enhanced affinity for mismatches and/or increased stability when bound to mismatches. Modified MutS, MutL, MutH or MutU proteins may be developed by exchanging and/or combining portions of these proteins from the various prokaryotic species listed above. Alternatively, in vitro evolution techniques like gene shuffling may be applied to obtain new prokaryotic MMR proteins with beneficial properties for affecting the activity of endogenous eukaryotic MMR processes.

The present invention also relates to a method for assisting gene targeting in eukaryotic systems. It is known that the efficiency of gene targeting is increased in MMR-deficient eukaryotic cells (Negritto, M T, Wu, X, Kuo, T, Chu, S, Bailis, A M: Influence of DNA sequence identity on efficiency of targeted gene replacement. Mol Cell Biol 17: 278-286, 1997). However, reliance on MMR-mutants to decrease MMR activity can be detrimental to the eukaryotic system due to increased mutation frequency and cellular apoptosis (Zhang, H, Richards, B, Wilson, T, Lloyd, M, Cranston, A, Thorburn, A, Fishel, R, Meuth, M: Apoptosis induced by overexpression of hMSH2 or hMLH1. Cancer Res. 59: 3021-3027, 1999) leading to decreased viability, vigour and productivity. The method as described herein, for example, to suppress endogenous eukaryotic MMR activity using prokaryotic MMR proteins, may be for gene targeting applications. By linking the prokaryotic MMR genes to regulatable or transiently expressed promoters, or by breeding out cassettes expressing these genes after the desired genetic events have been accomplished, then the mutation load on the host genome may be minimized. However, while the prokaryotic MMR proteins are being expressed, the genome of the host eukaryotic cells may be more efficiently manipulated by gene targeting.

Homeologous chromosomes are known to be present in the same nucleus in a wide range of polyploid plant species as well as in synthetic and natural plant interspecies hybrids. For example, but not to be considered limiting, in some crops such as wheat, entire chromosomes are homeologous. Hexaploid wheat has seven sets of distinct chromosomes each consisting of three collinear pairs of homologous chromosomes, 42 chromosomes in all. In *B. napus* (canola), some A-genome chromosomes (originating from *B. rapa*) such as N1 and N2 are collinear along their entire length with their C-genome counterparts (N11 and N12, respectively, originating from *B. oleracea*). In other crops such as maize, chromosome rearrangements have occurred during evolution so that collinear segments from homeologous chromosomes have been conserved rather than entire homeologous chromosomes. In a similar way, large portions of most A-genome chromosomes of *B. napus* (such as N3 and N4) are collinear with the corresponding portions of C-genome chromosomes (N13 and N14, respectively).

Homeologous recombination may allow the horizontal transfer of genetic variation between related species using interspecies hybrids as a bridge. For example, but not to be considered limiting, homeologous recombination may permit the acquisition of genes for disease resistance not normally found within the crop germplasm, from related species including wild relatives. Preferably, the method of the present invention is performed to transfer genetic material from direct progenitor species. For example, but not to be considered limiting, transfer into wheat of genes from two of the three diploid ancestors or transfer into *B. napus* of genes from its two diploid ancestors may be performed using the method of the present invention. Similarly, the method of the present invention may be employed to produce progeny from the crosses between less closely related species.

A representative example, which is not meant to be limiting in any manner includes the transfer of disease resistance into wheat from rye and transfer of the restoration of Ogura CMS (cytoplasmic male sterility) into canola (*B. napus*) from radish (*Raphanus sativum*). A potential problem with such crosses is that there are usually loci controlling important agronomic or quality characteristics that are linked to the locus controlling the particular trait under selection and that deleterious alleles at these linked loci may cause the co-inheritance of undesirable agronomic or quality characteristics along with inheritance of the new desired trait. An enduring problem is that this linkage drag may be very difficult to break because of the low frequency of homeologous recombination between the donor chromosome (carrying the segment of a homeologous chromosome on which the desired gene resides) and the normal crop chromosome not carrying the homeologous segment. An example of this problem is the transfer of the gene for restoration of Ogura CMS into canola from radish where the restorer gene is linked to a locus controlling seed glucosinolate content (a potentially important quality characteristic) and restorer lines express unacceptably high levels of glucosinolate accumulation in the seed.

The method of the present invention may increase the frequency of homeologous recombination in interspecies hybrids allowing for the identification of hybrid chromosomes (produced through homeologous recombination) wherein a homeologous recombination event had occurred in the interval separating the locus controlling the desired donor trait (such as disease resistance or CMS restoration) and a locus controlling quality or agronomic characteristics. Genetic markers may be employed by the method of the present invention to detect the products of such a homeologous recombination event. A variant of the recipient crop with an increased frequency of homeologous recombination may also offer the possibility of stimulating homeologous recombination in the desired interval when crossed with or when crossed to form an interspecies hybrid.

The method of the present invention may be employed to, for example, but not limited to, increase homeologous recombination in a eukaryote (for example see Example 4). Without wishing to be bound by theory, expression of MutS, MutL, MutU or MutH protein, or a combination thereof, in the eukaryote may function by disrupting or impairing the function of endogenous or native molecular machinery responsible for mismatch repair. In an embodiment of the present invention wherein the eukaryote is a plant or plant cell, the eukaryote may be a crop plant such as, but not limited to *B. napus*, or the progenitor species of a crop plant, such as *B. oleracea* or *B. rapa*. *B. oleracea* and *B. rapa* may be considered as the two species present in the ancestral interspecies hybrid that gave rise to *B. napus*.

According to the method of the present invention, a plant may be transformed with a nucleotide sequence capable of expressing, for example but not limited to, MutS protein. However, it is to be understood that a derivative of MutS, for example NLS-MutS, or other proteins, for example MutL, MutH, derivatives of MutL and MutH, for example NLS-MutL or NLS-MutH, or a combination of MutS, MutL or MutH, or derivatives thereof, may also be used. Expression of MutS may disrupt mis-match repair and promote homeologous recombination. The transgenic plant species may then be used as one parent (the recipient parent) in an interspecies cross with a donor parent. The donor parent is preferably from a species related to the recipient parent species and may carry a gene encoding a trait of interest. Any trait of interest is contemplated by the present invention, for example, but not limited to CMS or disease resistance. The interspecies hybrid formed from this interspecies cross (the amphihaploid) may then be subjected to chromosome doubling using a compound such as colchicine to produce an amphidiploid hybrid with two copies of each chromosome from each parent. A very much higher proportion of the gametes of the amphidiploid may be viable compared to the gametes of the amphihaploid. Because of the dominant effect of the disruption to the machinery responsible for mis-match repair, the frequency of homeologous recombination in the amphidiploid interspecies hybrid described above may be significantly elevated. This elevated frequency of homeologous recombination improves the possibility of a homeologous recombination event occurring in close proximity to the desirable donor gene of interest encoding the trait of interest.

The homeologous recombination event described above may produce a hybrid chromosome with a segment of chromosome from the recipient crop species closely adjacent to the locus from the homeologous donor chromosome that carries the gene controlling the trait of interest. Hybrid chromosomes with the desired structure are identified in the next generation, for example, by the appropriate application of genetic markers closely linked to the gene of interest and markers to loci in the homeologous region within the genome of the crop plant related to the donor species. The selection in the next generation of a chromosome resulting from a second homeologous recombination event, this time again close to the desired gene but on the other side of it, may result in a hybrid chromosome that is almost identical to a normal chromosome from the recipient crop species but which encodes a small internal segment from a donor chromosome. This segment of donor chromosome may carry the gene of interest from the donor species and can be collinear with the equivalent region of the native homeologous chromosome segment from the recipient crop species. The collinearity enhances subsequent breeding of the integrated donor segment between lines of the recipient crop species.

The hybrid chromosome described above may allow the introduction into a crop plant of a gene controlling a desirable trait without the associated introduction of alleles at linked loci that cause undesirable problems with agronomic performance or quality characteristics. The production and identification of a chromosome with the desired configuration may be enhanced by the method of the present invention.

In an alternate embodiment of the present invention, there is provided a method of decreasing the frequency of homeologous recombination or meiotic homologous recombination in a eukaryotic cell by overexpressing a native or a heterologous form of MSH2, or other key elements of the mis-match repair machinery either singly or in effective combinations during or immediately prior to meiosis. For example, which is not to be considered limiting in any manner, Example 3, Table 4, demonstrates that NLS-MUTS may be added to a eukaryotic host deficient in mismatch repair enzyme, to compliment endogenous mismatch repair activity. The reduced frequency of homeologous recombination may be desirable in varieties of amphipolyploid crop species, for example but not limited to canola. Further such a method may be employed to suppress homeologous or homologous recombination during backcrosses to a parent species to genetically fix or stabilize a desirable genotype.

Thus, in an embodiment, the present invention provides methods of plant and animal breeding, in which the frequency of non-sister chromatid exchange in meiotic homeologous recombination is modulated, prior to or during meiosis and gamete formation, when crossing a gamete from the parent organism with a second gamete to obtain progeny.

In an alternate embodiment of the present invention, the frequency of homeologous recombination (e.g see Example 3, Table 4) between non-sister chromatids during meiosis may be modified by expressing MutS, MutL, or both, of the present invention in the eukaryote thereby affecting one or more steps of the homeologous recombination process.

Homeologous recombination involves recombination between divergent sequences that are similar but not identical and whose recombination falls between the traditional categories of homologous and illegitimate (Selva, E M, Maderazo, A B, Lahue, R S: Differential effects of the mismatch repair genes MSH2 and MSH3 on homeologous recombination in *Saccharomyces cerevisiae*. Mol. Gen. Genet. 257: 71-82, 1997). Mismatch repair (MMR) processes regulate recombination between homeologous sequences that diverge by as little as a single base-pair to greater than 20% in both mitotic and meiotic cells (Selva, E M, et. al. Mol. Gen. Genet. 257: 71-82, 1997; Chen, W, Jinks-Robertson, S: The role of the mismatch repair machinery in regulating mitotic and meiotic recombination between diverged sequences in yeast. Genetics 151: 1299-1313, 1999). Such sequences may include those from related species where evolution has resulted in divergence of sequences in corresponding genes from the respective species. The ability to manipulate the frequency homeologous recombination during meiosis is a very desirable technology. Increasing meiotic homeologous recombination may be applied to promoting gene transfer between the genomes of different species brought together in an interspecific hybrid. In this manner the availability of genetic diversity to breeders of domestic crops and livestock may be increased. Alleles of genes encoding desirable production or quality traits present in other species but which were unusable to breeders due to genetic isolation could be more genetically attainable if meiotic homeologous recombination frequency could be increased. Conversely, an ability to reduce meiotic homeologous recombination frequency may be desirable to stabilize genomes where homeologous sequences exist. Such instances may exist in natural or synthetic amphipolyploid species where spontaneous exchanges between homeologous sequence may result in decreased vigour and/or productivity of the domestic crop or livestock species. Likewise suppressing recombination between homeologous sequences in vegetative cells leading to the germ-line is also important for stabilising the genomes of polyploidy species.

Homeologous recombination frequency is influenced by the activity of MMR processes. Part of the process of genetic recombination between two DNA sequences is the formation of heteroduplex DNA when a single strand of the donor DNA invades the recipient helix. During recombination between homeologous sequences, the sequence divergence between the sequences results in heteroduplex DNA that may have several mismatches. These mismatches may have similar structures as those which occur during DNA replication (described above). As a result, mismatches that occur during homeologous recombination events may be bound by MMR proteins. The recognition of mismatches during homeologous recombination events by MMR. proteins and subsequent activation of the MMR process may lead to dissolution of the homeologous recombination event and inhibition of formation of functional crossovers and genetic exchange between homeologous sequences. Genetic experiments have clearly demonstrated that reduced MMR activity may stimulate genetic recombination between homeologous sequences both during meiosis and in vegetative cells (Chen, W, Jinks-Robertson, S: The role of the mismatch repair machinery in regulating mitotic and meiotic recombination between diverged sequences in yeast. Genetics 151: 1299-1313, 1999; Hunter, N, Chambers, S R, Louis, E J, Borts, R H: The mismatch repair system contributes to meiotic sterility in an interspecific yeast hybrid. EMBO J. 15: 1726-1733, 1996). However, there is a need in the art for a method that can suppress the action of endogenous eukaryotic MMR activity and promote homeologous recombination without relying on mutations in endogenous MMR genes. Mutation of endogenous eukaryotic MMR proteins can result in activation of cellular apoptosis (Toft, N J, Winton, D J, Kelly, J, Howard, L A, Dekker, M, te Rjel, H, Arends, M J, Wyllie, A H, Margison, G P, Clarke, A R: Msh2 status modulates both apoptosis and mutation frequency in the murine small intestine. Proc. Natl. Acad. Sci. U.S.A 96: 3911-3915, 1999) leading to decreased host viability, vigour and productivity.

One example of a method to increase HeR frequency in eukaryotic cells is to express prokaryotic MMR proteins to suppress the activity of endogenous eukaryotic MMR processes. Without wishing to be bound by theory, the prokaryotic MMR proteins may act by binding to mismatches or other structural distortions that may occur in heteroduplex DNA formed during genetic recombination between homeologous sequences. By binding the mismatches, the prokaryotic MMR proteins may sequester the mismatches thereby inhibiting the binding and activation of the endogenous eukaryotic MMR proteins. Expression of the prokaryotic MMR proteins in the eukaryotic host may thereby increase homeologous recombination frequency by inhibiting the function of the endogenous MMR process.

In another embodiment, the present invention provides a method of increasing meiotic homeologous recombination in the context of breeding agricultural species, and plants and animals produced by such processes. Increased recombination frequency may be desirable to facilitate breeding of agricultural species, for example by facilitating the exchange of alleles at tightly linked genetic loci. Where breeding stock are modified to increase the level of meiotic homologous recombination, for example, the effort required to identify progeny which have lost an undesirable allele at a genetic locus of interest may be reduced. One aspect of the invention involves the modulation of meiotic homologous recombination frequency in plant breeding, for example, but not limited to *Brassica* spp., wheat, corn, soybean, barley, and the like.

Also, according to the present invention, there is provided a method of increasing homologous recombination between dissimilar nucleotide sequences in a eukaryote, comprising the steps of a) transforming or providing the eukaryote with a first nucleotide sequence capable of expressing a MutS, MutL, MutH, MutU protein, or a combination thereof, and a second nucleotide sequence comprising a nucleotide targeting sequence, and b) expressing the MutS, MutL, MutH, MutU protein, or combination thereof, in the presence of the nucleotide targeting sequence.

Further, either meiotic or mitotic homologous recombination may be enhanced by the method of the present invention. Similarities and differences between meiotic and mitotic recombination are discussed generally in WO 02/22811, which is herein incorporated by reference.

By the term "nucleotide targeting sequence" it is meant a nucleotide sequence that is substantially homologous to one or more regions of a genomic nucleotide sequence in the eukaryote. In this context, by "substantially homologous" it is meant that the nucleotide targeting sequence is capable of hybridizing to the corresponding nucleotide sequences within the nucleus of the eukaryote under normal physiological or cell culture conditions. In addition, a nucleotide targeting sequence is considered to be substantially homologous to the genomic nucleotide sequence if both sequences are capable of hybridizing under stringent hybridization conditions, for example, as defined in Maniatis et al., in Molecular Cloning (A Laboratory Manual), Cold Spring Harbor Laboratory (1982) p 387 to 389). An example of one such stringent hybridization condition may be hybridization at 4×SSC at 65° C. for about 8-16 hours or overnight, followed by washing in 0.1×SSC at 65° C. for an hour. Alternatively, a stringent hybridization condition could be in 50% formamide, 4×SSC at 42° C. for about 8-16 hours, or overnight, followed by washing in 0.1×SSC at 65° C. for an hour. However, other hybridization conditions are also contemplated by the present invention.

Figure 1B:
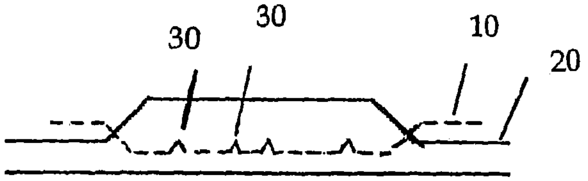
FIG. 1B shows a nucleotide targeting sequence hybridized to the complementary copy of a genomic nucleotide sequence. The nucleotide targeting sequence comprises multiple nucleotide mismatches with the genomic nucleotide sequence.

In an embodiment of the present invention, which is not meant to be limiting, the nucleotide targeting sequence may be identical to a genomic nucleotide sequence within the eukaryote, except for a single nucleotide mismatch. For example, FIG. 1A depicts an embodiment wherein the nucleotide targeting sequence (10) is hybridized to the complementary copy of the genomic nucleotide sequence (20). Also shown in FIG. 1A is a single base pair mismatch (30) that occurs during hybridization as a result of the difference between the nucleotide targeting sequence and the genomic nucleotide sequence. In such an embodiment, the single nucleotide mismatch is preferably located in the middle or near the middle of the nucleotide targeting sequence, such that the single nucleotide mismatch region is flanked by regions which are capable of hybridizing to the complementary strand of the genomic nucleotide sequence. In an alternate embodiment, the nucleotide targeting sequence may comprise more than one nucleotide mismatch, for example as shown in FIG. 1B.

Without wishing to be bound by theory, eukaryotic expression of a bacterial mutS protein, such as, but not limited to EcMutS (*E. coli* MutS) in the presence of a nucleotide targeting sequence may enhance homologous recombination of the nucleotide targeting sequence into the genome of the eukaryote by inhibiting the endogenous mismatch repair system of the eukaryote. Alternatively, MutS, MutL, MutH, MutU or a combination of MutS, MutL, MutU and MutH may be used. In such a manner, the present invention may be employed to introduce one or more mutations into the genome of a eukaryote. Without wishing to be limiting, the one or more mutations may be introduced into any desired nucleotide sequence, for example, but not limited to, a regulatory region, a promoter, enhancer, terminator, intron, exon, gene or coding region of interest or any combination thereof. Further, the present invention may be employed to generate additions or deletions in the genome of a eukaryote. The present invention may also be employed to integrate transgenic nucleotide sequences into the genome of a eukaryote. Such transgenic nucleotide sequences may also encode one or more transgenic proteins of interest.

Methods of transforming eukaryotic cells are well known in the art and any of such methods may be employed to transform the eukaryote according to the method of the present invention. In an embodiment of the present invention wherein the eukaryote is a plant or plant cell, transformation may be performed for example, but not limited to using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology,* 2d Ed. (1988); and Miki and Iyer, *Fundamentals of Gene Transfer in Plants*. In *Plant Metabolism,* 2d Ed. D T. Dennis, D H Turpin, D D Lefebrve, D B Layzell (eds), Addison Wesly, Langmans Ltd. London, pp. 561-579 (1997).

The present invention further contemplates expressing one or more additional proteins involved in promoting homologous recombination, for example, but not limited to factors that promote double strand breaks in DNA such as, but not limited to SPO11, factors involved in resection of nucleotide strands, such as, but not limited to MRE11, RAD50, and XRS2/NBS1, factors involved in strand invasion such as, but not limited to RecA homologues, DMC1, RAD51, RAD 52, RAD54, RAD55, RAD57, TIDI, MSI-14 and MSH5 or resolvase, BLM, WRN, SGS1, or chromatin remodeling proteins such as, but not limited to histone acetylases or synaptonemal complex proteins for example, but not limited to as described in WO 02/22811, WO 01/62945, WO 01/61012, U.S. Pat. No. 6,146,894, and references included therein, all of which are herein incorporated by reference.

The present invention also contemplates genetic constructs which may be employed in the method of the present invention and eukaryotes produced according to the methods as described herein.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

Example 1

Cloning and Evaluation of Muts, MutL and MutH Genes

Genes and genetic elements of interest were cloned using specific oligonucleotides designed to prime DNA synthesis in a polymerase chain reaction (PCR) with either cDNA or genomic DNA (gDNA) from the appropriate species as template. The primers were designed to incorporate convenient restriction sites into the amplicon to facilitate initial cloning of the gene or genetic element and subsequent subcloning into various expression or analytical vectors. Genes and genetic elements cloned and the oligonucleotide primers used to achieve this are described below.

PCR conditions were as described (*Current Protocols in Molecular Biology*. Ausubel, F M, Brent, R, Kingston, R E, Moore, D D, Seidman, J G, Smith, J A, Struhl, K eds. 2001. 1987. John Wiley and Sons, Inc) or as recommended by the supplier of the thermostable DNA polymerase Pfu (Stratagene), Pfx (Gibco BRL) or Taq (Pharmacia). PCR reactions were conducted using a thermocycler (Perkin-Elmer Model 9700) following the directions of the manufacturer. In some cases specific restriction fragments known to encode the gene or genetic element of interest, based on sequence information from genome databases, were directly cloned from complex mixtures of DNA fragments without any PCR amplification. In other cases, specific restriction fragments known to encode the gene or genetic element of interest based on restriction maps of plasmids encoding the desired components were subcloned into other vectors for various applications. DNA sequence of clones was determined at a commercial sequencing facility (National Research Council—Plant Biotechnology Institute, Saskatoon, Canada).

Strains of *Escherichia coli* were cultured at 37° C. following standard procedures (Current Protocols in Molecular Biology. Ausubel, F M, et al. eds. 2001. 1987. John Wiley and Sons, Inc.) with noted exceptions using TYS broth (per liter distilled water: 10 g Tryptone (Difco); 5 g yeast extract (Difco); 5 g NaCl (Sigma)) or TYS plates (i.e. TYS medium plus agar (1.5% (w/v); Sigma)) with appropriate levels of antibiotics (i.e. ampicillin (100 μg/ml); kanamycin (50 μg/ml); chloramphenicol (20 μg/ml); tetracycline (12 μg/ml)) where necessary to ensure selection and maintenance of plasmid constructs.

Cloning of Prokaryotic Mismatch Repair Proteins (MMR)

The genes encoding examples of prokaryotic MMR proteins were cloned from *E. coli*. Template DNA for amplifying MutS genes was either plasmid pMQ315, encoding wild type MutS, or pS501, encoding the $MutS^{501}$ mutant allele (Wu, T H, Marinus, M G: Dominant negative mutator mutations in the mutS gene of *Escherichia coli*. J. Bacteriol. 176: 5393-5400, 1994). Both plasmids were obtained from Dr. M. G. Marinus (Department of Pharmacology, University of Massachusetts Medical School, Worcester, Mass.) and described in (Wu, T H et al. 1994). PCR reactions were performed with approximately 1 μg of plasmid DNA as template, 1.0 pmol each of the forward and reverse primers, 0.2 mM dNTP's, 2.5 U Pfu (Stratagene) and Pfu buffer constituents provided by the manufacturer in a volume of 50 μl. The PCR was performed following standard procedures (*Current Protocols in Molecular Biology*. Ausubel, F M, et al. eds. 2001. 1987. John Wiley and Sons, Inc.). Table 2 lists the primers used to amplify the various genes described here. The reverse primer 3'Pst-EcMut was used in combination with the forward primers 5'Bam-EcMut, Bam-NLS-Sma-EcMut, or EcoRV-NLS-Sma-EcMut in separate respective reactions.

TABLE 2

Oligonucleotides for Amplifying and Modifying Target Gene

| Oligo name | Target | Sequence (5'-3') |
|---|---|---|
| 5'Bam-EcMut | MutS | CGGGATCCAAAAAAATGTCTGCTATAGAAAATTTCGA CGCCCAT (SEQ ID NO: 18) |
| 3'Pst-EcMut | MutS | AACTGCAGTTATTACACCAGGCTCTTCAAG (SEQ ID NO: 19) |
| Bam-NLS-Sma-EcMut | MutS | CGGGATCCAAAAAAATGGCTCCTAAGAAGAAGAGAAA GGTTGGAGGAGGACCCGGGAGTGCAATAGAAAATTTC GAC (SEQ ID NO: 20) |
| EcoRV-NLS-Sma-EcMut | MutS | CGGATATCATGGCTCCTAAGAAGAAGAGAAAGGTTGG AGGAGGACCCGGGAGTGCAATAGAAAATTTCGAC (SEQ ID NO: 21) |
| EcMutL-5'Sma | MutL | GAATTCCCCGGGCCAATTCAGGTCTTACCGC (SEQ ID NO: 22) |
| EcMutL-3'Pst | MutL | AAACTGCAGTCATCACTCATCTTTCAGGGCT (SEQ ID NO: 23) |
| MutH-5'BamSfo | MutH | ATCGGATCCGGCGCCATGTCCCAACCTCGCCC (SEQ ID NO: 24) |
| MutH-3'XhoNot | MutH | ATCCTCGAGCGGCCGCTCACTACTGGATCAGAAAATG ACGGG (SEQ ID NO: 25) |

Strains of *Saccharomyces cerevisiae* were cultured at 30° C. following standard procedures (Adams, A, Gottschling, D E, Kaiser, C A, Stearns, T: Methods in *Yeast Genetics*. Cold Spring Harbor Laboratory Press, (1997), *Current Protocols in Molecular Biology*. Ausubel, F M, et. al. eds. 2001. 1987. John Wiley and Sons, Inc) with noted exceptions using YPD broth (per liter: 10 g Bacto-yeast extract, 20 g Bacto-peptone, 20 g glucose) or YPD plates (i.e. YPD medium plus agar (2% (w/v)), or on minimal medium (SC) with appropriate amino acid supplements to ensure selection of plasmid constructs (Adams, A, Gottschling, D E, Kaiser, C A, Stearns, T: Methods in Yeast Genetics. Cold Spring Harbor Laboratory Press, (1997), Current Protocols in Molecular Biology. Ausubel, F M, et. al. eds. 2001. 1987. John Wiley and Sons, Inc).

After completion of the cycling, DNA fragments were resolved by agarose electrophoresis using a 1% gel and following standard procedures (Current Protocols in Molecular Biology. Ausubel, F M, et. al. eds. 2001. 1987. John Wiley and Sons, Inc.). DNA fragments of ~2.6 kilobase pair (kb) expected to correspond to MutS or derivatives were excised and the DNA recovered from the agarose using the Qiaquick Gel Extraction Kit (Qiagen) following the protocol supplied by the manufacturer. The amplicon and vector DNA were digested with restriction enzymes following standard procedures (Current Protocols in Molecular Biology. Ausubel, F M, et. al. eds. 2001. 1987. John Wiley and Sons, Inc.). The amplicon and vector DNA were purified by agarose electrophoresis and recovered as described above. Amplicon and vector DNA were then mixed in the presence of T4 DNA ligase (Gibco-BRL) to covalently link the two molecules following standard procedures in a final volume of 25 μl. After incubating the ligation reaction as described (Current Protocols in Molecular Biology. Ausubel, F M, et. al. eds. 2001. 1987. John Wiley and Sons, Inc.), 1 μl of glycogen (20 mg/ml) was added to the ligation mixture and made up to 100 μl with distilled water. After precipitation with ethanol, the DNA was resuspended in 4 μl of distilled water.

An appropriate *E. coli* strain (e.g. DH5α (Gibco-BRL)) was transformed with 2.5 μl of the concentrated ligation following standard procedures and plated on sterile TYS medium containing ampicillin. Putative clones were propagated in TYS broth and ampicillin. Plasmid DNA was isolated by standard alkaline-lysis "mini-prep" procedure. The DNA sequences of the resultant clones were determined at a commercial sequencing facility (National Research Council—Plant Biotechnology Institute, Saskatoon, Canada) to confirm they encoded intact copies of the respective genes. Cloning of all genes and genetic elements described in this invention followed these same principles, with noted exceptions. The MutS and $MutS^{501}$ genes amplified with 5'Bam-EcMut and 3'Pst-EcMut (see Table 2) were each cloned into pBluescript KS-(Stratagene) using BamHI and PstI resulting in the constructs pTK18 and pTK16, respectively. The MutS and $MutS^{501}$ genes amplified with BamNLS-Sma-EcMut and 3'Pst-EcMut (see Table 2) were each cloned into pBluescript KS (Stratagene) using BamHI and PstI resulting in the constructs pTK19 and pTK17, respectively. The MutS and $MutS^{501}$ genes amplified with EcoRV-NLS-Sma-EcMut and 3'Pst-EcMut (see Table 2) were each digested with PstI then cloned into SmaI and PstI sites of pBluescript KS-(Stratagene) resulting in the constructs pTK20 and pTK21, respectively. The constructs pTK19, pTK17, pTK20 and pTK21 all encode the nuclear localization sequence (NLS) corresponding to that found in simian virus 40 T-antigen (Kalderon, D, Roberts, B L, Richardson, W D, Smith, A E: A short amino acid sequence able to specify nuclear location. Cell 39: 499-509, 1984). This NLS has been demonstrated to function in animal, yeast and plant cells (Kalderon, D, Roberts, B L, Richardson, W D, Smith, A E: A short amino acid sequence able to specify nuclear location. Cell 39: 499-509, 1984; Goldfarb, D S, Gariepy, J, Schoolnik, G, Komberg, R D: Synthetic peptides as nuclear localization signals. Nature 322: 641-644, 1986; Nelson, M, Silver, P: Context affects nuclear protein localization in *Saccharomyces cerevisiae*. Mol. Cell Biol. 9: 384-389, 1989; van der Krol, A R, Chua, N H: The basic domain of plant B-ZIP proteins facilitates import of a reporter protein into plant nuclei. Plant Cell 3: 667-675, 1991). The resultant genes and cognate proteins were designated NLS-MutS and NLS-$MutS^{501}$. The sequences of NLS-MutS (SEQ ID NO:1), NLS-MutL (SEQ ID No:2), NLS-MutH (SEQ ID NO:3), NLS-MutU (SEQ ID NO:28), and a NLS-MutS RS (SEQ ID NO:27), comprising a codon-optimized sequence for expression in crucifers are shown in FIGS. 2A-E.

Alternatively, prokaryotic mismatch repair proteins may be fused to a C-terminal nuclear localisation sequence. An example of a C-terminal NLS is that from the VirD2 protein which is functional in animal, yeast and plant cells (Relic, B, Andjelkovic, M, Rossi, L, Nagamine, Y, Hohn, B: Interaction of the DNA modifying proteins VirD1 and VirD2 of *Agrobacterium tumefaciens*: analysis by subcellular localization in mammalian cells. Proc Natl Acad Sci USA 95: 9105-9110, 1998; Tinland, B, Koukolikova-Nicola, Z, Hall, M N, Hohn, B: The T-DNA-linked VirD2 protein contains two distinct functional nuclear localization signals. Proc Natl Acad Sci USA 89: 7442-7446; 1992).

NLS-MutS and NLS-$MutS^{501}$ genes were cloned into a vector capable of expressing the proteins in *E. coli* by the tac promoter (Russell, D, Bennet, G. Construction and analysis of in vivo activity of *E. coli* promoter hybrids and promoter mutants that alter the −35 to −10 spacing. Gene 20: 231-243, 1982), which is regulated by the gratuitous inducer IPTG. NLS-MutS was cloned into pDK5 (Kleiner, D, Paul, W, Merrick, M J: Construction of multicopy expression vectors for regulated over-production of proteins in *Klebsiella pneumoniae* and other enteric bacteria. J Gen Microbiol 134: 1779-1784; 1988) by digesting pDK5 first with EcoRI, making the ends blunt by treatment with the Klenow fragment of DNA polymerase following standard procedures (*Current Protocols in Molecular Biology*. Ausubel, F M, et al. eds. 2001. 1987. John Wiley and Sons, Inc.), then digesting with PstI. To this prepared vector the amplicon used to create pTK20 was ligated after first digesting with EcoRV and PstI. The resultant construct with NLS-MutS cloned into pDK5 was designated pTK22. To assemble a construct to express NLS-$MutS^{501}$ pTK22 and pTK21 were each digested with NcoI and PstI. The approximately 5.1 kb vector fragment derived from pTK22 encoding the 5' ~800 bp of NLS-MutS was then ligated to the ~1.8 kb fragment derived from pTK21 encoding the 3' portion of $MutS^{501}$ that contains the mutated sequence of this allele. The resulting assembly resynthesises the $MutS^{501}$ allele but is now linked to the SV40 NLS in pDK5. This construct encoding NLS-$MutS^{501}$ in pDK5 was designated $pTK_{24}$.

The MutL gene was also cloned from *E. coli*. Template DNA for amplifying the MutL was obtained by isolating genomic DNA from the ECOR70 strain (American Type Culture Collection #35389), following standard procedures (Current Protocols in Molecular Biology. Ausubel, F M, et. al. eds. 2001. 1987. John Wiley and Sons, Inc.). PCR reactions were performed with approximately 1 μg of genomic DNA as template, and the primers EcMutL-5'Sma and EcMutL-3'Pst. The ~1.9 kb amplicon was digested with PstI and cloned into the pBluescript KS-(Stratagene) digested with SmaI and PstI resulting in the construct pTK55. MutL was attached to the NLS-encoding sequence of pTK19 by using SmaI and PstI resulting in the construct pTK60.

The MutH gene was cloned using DNA from *E. coli* strain ECOR70 as template in a PCR reaction with the primers MutH-5'BamSfo and MutH-3'XhoNot. The amplicon was cloned in two different fashions. First, the amplicon was digested with BamHI and XhoI and ligated to a derivative of pENTR1A (Gibco-BRL) which encodes an *E. coli* ribosome binding site adjacent the vector SalI site. The resultant construct encoding the unmodified MutH was designated pTK180. Secondly, the amplicon was digested with SfoI and XhoI and cloned into a derivative of pENTR1A encoding an *E. coli* ribosome binding site, as per above, and the NLS from SV40 T-antigen. The NLS is followed by a sequence encoding the FLAG peptide (Hopp, T, Prickett, S, Price, V, Libby, R, March, C, Cerretti, D, Urdal, D, Conlon, P. A short polypeptide marker sequence useful for recombinant protein identification and purification. Bio/technology 6: 1204-1210, 1988), which enables detection of the fusion protein using commercially available antibodies (Sigma), and a tract of glycine residues to promote flexibility between MutH and the N-terminal additions. A pair of synthetic oligonucleotides were created which, when annealed together, can form a double-stranded DNA molecule which encodes the nuclear localization sequence corresponding to that found in simian virus 40 T-antigen (Kalderon, D, Roberts, B L, Richardson, W D, Smith, A E: A short amino acid sequence able to specify nuclear location. Cell 39: 499-509, 1984), the FLAG peptide and the glycine tract. The nucleotide sequence encoding these components were:

These oligonucleotides when annealed together form a cohesive end at the 5' end corresponding to the BamHI site and a cohesive end at the 3' end corresponding to the SfoI site. The two oligonucleotides were annealed together as per instructions supplied by the supplier (National Research Council—Plant Biotechnology Institute).

The resultant construct with MutH fused to the NLS-FLAG-Gly peptide was designated pTK181.

Plasmid constructs were assembled to facilitate expression of prokaryotic mismatch repair proteins and variants thereof in eukaryotic yeast using an expression system developed by Gari et al., (Gari, E, Piedrafita, L, Aldea, M, Herrero, E: A set of vectors with a tetracycline-regulatable promoter system for modulated gene expression in *Saccharomyces cerevisiae*. Yeast 13: 837-848, 1997). Briefly, the transcription promoters on these plasmids are a hybrid system developed by Gari et al. (1997) that permits suppression or induction of gene expression by varying growth medium constituents. This transcription control system employs components of the regulatory system controlling expression of tetracycline resistance in prokaryotes. As a result, in the presence of tetracycline or doxycycline, an analogue of tetracycline, transcription of the target gene is suppressed. Conversely, when tetracycline or doxycycline is absent efficient transcription of the target gene can occur. By varying the number of tetO sites in the promoter from two (i.e. Tet2x promoter) to seven (i.e. Tet7x promoter), the promoter strength can be increased ~2-fold. The combination of vector copy number (i.e. CEN-type vs. 2u-type with copy numbers of 1-2 plasmids per cell or up to 40 plasmids per cell, respectively; Schneider, J C, Guarente, L: Vectors for expression of cloned genes in yeast: regulation, overproduction, and underproduction. Methods Enzymol. 194: 373-388, 1991) and promoter strength allows gene expression to be varied ~5-fold.

Yeast expression plasmids using this system of gene regulation include pCM188, pCM189 and pCM190 as described by Gari et al., (Gari, E, Piedrafita, L, Aldea, M, Herrero, E: Yeast 13: 837-848, 1997), as well as derivatives thereof. These derivatives were based on the plasmids described by Geitz et al., (Gietz, R D, Sugino, A: New yeast-*Escherichia coli* shuttle vectors constructed with in vitro mutagenized yeast genes lacking six-base pair restriction sites. Gene 74: 527-534, 1988) and were created by subcloning an EcoRI-HindIII fragment encoding either the Tet2x (~2.6 kb) or Tet7x (~2.8 kb) promoter elements from pCM 188 or pCM190, respectively, into the EcoRI-HindIII site of YEplac112 (i.e. creating YEplac112-Tet7x), or YCplac22 (i.e. creating YCplac22-Tet2x), or YEplac181 (i.e. creating YEplac181-Tet2x) or YCplac111 (i.e. creating YCplac111-Tet2x). In addition, derivatives of these plasmids were created which contained the Destination cassette (Gibco BRL). pCM188 and pCM190 were each digested with BamHI and PstI and then treated with T4 polymerase to make the DNA ends blunt before ligation to the Destination-C cassette (Gibco BRL) to create pAS13 (i.e. pCM188-DEST) and pAS14 (i.e. pCM190-DEST).

Restriction enzyme analysis demonstrated that the Destination-C cassette in these vectors was in a sense orientation with regard to the promoter so that genes transferred into the Destination cassette would be functionally expressed. pAS13 and pAS14 were then each digested with XhoI and HindIII to release fragments encoding the Tet2x and Tet7x promoters, respectively, plus the attached Destination-C cassette. These fragments were then ligated to either YCplac22-Tet2x to create pAS22 (i.e. YCplac22-Tet2x-DEST), YEplac112-Tet7x to create pAS23 (i.e. YEplac112-Tet7x-DEST), YCplac111-Tet2x to create YCplac111-Tet2x-DEST, or YCplac111-Tet7x to create YCplac111-Tet7x-DEST.

The genes encoding prokaryotic mismatch repair proteins and derivatives thereof were subcloned into yeast expression vectors as follows:

MutS was subcloned from pTK18 into the YEplac112-Tet7x using BamHI and PstI resulting in the construct pTK42.

NLS-MutS was subcloned from pTK19 into YEplac112-Tet7x using BamHI and PstI resulting in the construct pTK37.

NLS-MutS was subcloned from pTK19 into pCM190 using BamHI and PstI resulting in the construct pTK40.

NLS-MutS was subcloned from pTK19 into YCplac22-Tet2x using BamHI and PstI resulting in the construct pTK43.

NLS-MutS$^{501}$ was subcloned from pTK17 into pCM190 using BamHI and PstI resulting in the construct pTK41.

NLS-MutL was subcloned from pTK60 into YEplac112-Tet7x using BamHI and PstI resulting in the construct pTK61.

Transfer of NLS-MutH to the yeast expression vector YEplac181-Tet7x-DEST was done using the Clonase reaction (InVitrogen) following the directions of the manufacturer.

MutU is amplified from an *E. coli* K12 genome using the following primers:

```
UVR-5'BglNco:
                                        (SEQ ID NO: 29)
ATCAGATCTGCCATGGACGTTTCTTACCTGCTCG
and

UVR-3'XhoNotSfo
                                        (SEQ ID NO: 30)
ATCCTCGAGGCGGCCGCTTAGGCGCCCACCGACTCCAGCCGGGCGTA.
```

After digestion with NcoI and NotI the MutU gene is cloned into the corresponding sites of pENTR11 (Gibco-BRL). To promote accumulation of MutU protein in the nucleus of a eukaryotic cell, the MutU gene may be engineered to encode a NLS. The MutU amplicon is digested with BglII and SfoI and ligated to the BamHI and SfoI sites of pNML27. pNML27 encodes a sequence:

```
                                        (SEQ ID NO: 31)
GGCGCCGGTGGAGGTGGAGGTGGAGGTGGACCCGGGCTTTCAAAGCGTCC

GCGTGAAGATGATGATGGAGAACCGAGTGAACGCAAACGCGAGAGAGATG

AGGTT AACGGTGATTACAAGGATGATGATGATAAGTAATAA,
```

which encodes eight glycine residues, followed by 22 residues encoding the C-terminal NLS of VirD2 (Relic, B, Andjelkovic, M, Rossi, L, Nagamine, Y, Hohn, B: Interaction of the DNA modifying proteins VirD1 and VirD2 of *Agrobacterium tumefaciens*: analysis by subcellular localization in mammalian cells. Proc Natl Acad Sci USA 95: 9105-9110, 1998; Tinland, B, Hall, M N, Hohn, B: The T-DNA-linked VirD2 protein contains two distinct functional nuclear localization signals. Proc Natl Acad Sci USA 89: 7442-7446; 1992), followed by the FLAG peptide (Hopp, T, Prickett, S, Price, V, Libby, R, March, C, Cerretti, D, Urdal, D, Conlon, P. A short polypeptide marker sequence useful for recombinant protein identification and purification. Bio/technology 6: 1204-1210, 1988).

Example 2

Functionality of Engineered Prokaryotic Mismatch Repair Proteins

To promote localisation of prokaryotic MMR proteins in the nucleus of eukaryotic cells the proteins may be engineered to encode a nuclear localisation sequence. (NLS). A NLS is a sequence of amino acid residues resident in many eukaryotic proteins that function in the host cell nucleus. The NLS interacts directly or indirectly with nuclear envelope proteins that facilitate transport of proteins from the cytosol, where protein synthesis occurs, into the nucleus.

Protein function can be very sensitive to perturbations of their folding and three-dimensional structure. Addition of amino acid residues to proteins may often cause structural perturbations that inhibit or even prohibit function. Therefore when engineering proteins, such as modifying one to encode an NLS, it is important to confirm functional activity is retained in the engineered protein.

To illustrate prokaryotic MMR proteins retain function in MMR processes when engineered to encode an NLS, the function of such proteins was evaluated using a genetic assay in *E. coli*. This assay was done in two ways. Firstly, a wild type MMR protein engineered to encode an NLS was assessed for its ability to complement a corresponding mutant gene in *E. coli*. Secondly, a mutant MMR protein engineered to encode an NLS was assessed for its ability to inhibit the function of the corresponding wild type protein in *E. coli*. The genetic assay employed the *E. coli* strains CC106 (Cupples, C G, Miller, J H: A set of lacZ mutations in *Escherichia coli* that allow rapid detection of each of the six base substitutions. Proc. Natl. Acad. Sci. U.S.A. 86: 5345-5349, 1989) and GM4257 (Wu, T H, Marinus, M G: Dominant negative mutator mutations in the mutS gene of *Escherichia coli*. J. Bacteriol. 176: 5393-5400, 1994).

CC106 encodes a mutant allele of the LacZ gene (i.e. $lacZ^{CC106}$) resulting from nucleotide 1384 (with respect to the A residue of the ATG start codon) being changed from G to A. This causes amino acid residue 461 in the LacZ protein to encode lysine versus glutamate. The result is a non-functional enzyme since the glutamate at position 461 is essential for enzyme activity. One can thus monitor mutation frequency resulting from changes in mismatch repair activity by monitoring reversion of the mutant $lacZ^{CC106}$ allele to $lacZ^+$. For example, during DNA replication a nucleotide may be inserted at position 1384 of $lacZ^{CC106}$ which could restore the sequence to encode a glutamate residue at position 461. However, MMR activities may act to maintain the mutant sequence. Inhibition of MMR function would thus act to promote conversion of $lacZ^{CC106}$ to $lacZ^+$. CC106 encodes wild-type alleles of MMR proteins so interference of the function of these proteins may result in an increased reversion frequency of $lacZ^{CC106}$ to lace.

The strain GM4257 is isogenic to CC106 except that it encodes a null allele of MutS, $mutS^-$. As a result of this mismatch repair defect, GM4257 has a high frequency of reversion of $lacZ^{CC106}$ to $lacZ^+$. Genetic complementation of the $mutS^-$ allele in GM4257 by a functional MutS protein may decrease the reversion frequency.

To assay reversion frequency of the $lacZ^{CC106}$ allele, a papillation assay was employed as described (Wu, T H, Marinus, M G: Dominant negative mutator mutations in the mutS gene of *Escherichia coli*. J. Bacteriol. 176: 5393-5400, 1994). In this assay *E. coli* strains are plated on MacConkey medium containing lactose. Colonies of cells unable to catabolyse lactose (e.g. due to a defective LacZ enzyme) are white whereas colonies catabolysing lactose appear red. Thus reversion of the $lacZ^{CC106}$ allele to $lacZ^+$ can produce red micro-colonies (i.e. papillae) within a majority white colony. The frequency of papillation is thus an indicator of mutation frequency.

Papillation frequency was determined for *E. coli* GM4257 expressing wild-type MutS engineered to encode a nuclear localisation sequence (i.e. pTK22), as well as for a control strain expressing the corresponding empty parental vector (i.e. pDK5) As shown in Table 3, the engineered NLS-MutS was very capable at complementing the $mutS^-$ allele of GM4257 as shown by the 10-fold decrease in papillation frequency when NLS-MutS was being expressed. This clearly demonstrates that prokaryotic MMR proteins can be engineered to encode a NLS and still maintain their function in recognizing DNA substrates with mismatched base pairs.

TABLE 3

Effect of a nuclear localization sequence on function of EcMutS[a]

| *E. coli* Genotype[b] | Plasmid | Gene | Papillation frequency (%)[c] |
|---|---|---|---|
| MutS | pDK5 | n/a | 5.5 ± 2.1 |
| | pTK24 | NLS-mutS[501d] | 37 ± 14.7 |
| mutS | pDK5 | n/a | 30.9 ± 2.7 |
| | pTK22 | NLS-MutS | 3.0 ± 2.0 |

[a]EcMutS was engineered to encode the nuclear localization sequence from SV40 T-antigen.
[b]Host strains were CC106 (MutS) or GM4257 (mutS) (Wu and Marinus, 1994).
[c]Represents the frequency of colonies with papillae when grown on MacConkey agar containing IPTG.
[d]501 allele encodes an amino acid change (G619D) within the P-loop motif of the ATP-binding site (Wu and Marinus, 1994).

Papillaton frequency was also determined for *E. coli* CC106 expressing the $mutS^{501}$ allele engineered to encode an NLS (i.e. pTK24). The $mutS^{501}$ allele has a mutation resulting in amino acid residue 619 being changed from glycine to aspartate (i.e. G619D). This alters the function of the P-loop motif which is involved in the binding and/or hydrolysis of ATP (Wu, T H, Marinus, M G, J. Bacteriol. 176: 5393-5400, 1994). Expression of $MutS^{501}$ in a wild-type *E. coli* strain can increase mutation frequency due to a dominant-negative effect where the mutant protein competes with the endogenous MutS protein thereby suppressing MMR function (Wu, T H, Marinus, M G, J. Bacteriol. 176: 5393-5400, 1994). Thus $MutS^{501}$ protein engineered to encode a NLS may also be expected to increase mutation frequency if the engineered protein is in a normal conformation. As shown in Table 3, the engineered NLS-MutS501 was very capable of inhibiting the endogenous MutS+ protein of CC106. This is reflected by the approximately 7-fold increase in papillation frequency when NLS-MutS501 was expressed. This clearly demonstrates that prokaryotic MMR proteins can be engineered to encode a NLS and still maintain their function in recognizing DNA substrates with mismatched base pairs.

Example 3

Effect of Prokaryotic Mismatch Repair Proteins on Mutation Frequency in Eukaryotic Cells Incorporation of additional, insufficient or incorrect nucleotide(s) often occurs during DNA replication. These mistakes in the newly synthesized stand are generally corrected by the proofreading activity of DNA polymerase. However, these mistakes may escape the proofreading activity and result in structural distortions of the DNA helix. These distortions, or mismatches, are recognized and repaired by the mismatch repair (MMR) machinery (Harfe, B D, Jinks-Robertson, S: DNA Mismatch Repair And Genetic Instability. Annu Rev. Genet. 34: 359, 2000; Marra, G, Schar, P: Recognition of DNA alterations by the mismatch repair system. Biochem. J. 338: 1-13, 1999). Disruption of the function of MMR processes can thus inhibit repair of replication errors leading to stabilization of the mutations and their passage to subsequent generations.

In eukaryotes the recognition of mismatches principally is done by the MSH2 protein which is highly conserved from lower eukaryotes like yeast to higher eukaryotes including plants and humans (Harfe, B D, Jinks-Robertson, S: DNA Mismatch Repair And Genetic Instability. Annu Rev. Genet. 34: 359, 2000; Marra, G, Schar, P: Recognition of DNA alterations by the mismatch repair system. Biochem. J. 338: 1-13, 1999; Eisen, J A: A phylogenomic study of the MutS family of proteins. Nucleic Acids Res. 26: 4291-4300, 1998; Culligan, K M, Meyer-Gauen, G, Lyons-Weiler, J, Hays, J B: Evolutionary origin, diversification and specialization of eukaryotic MutS homolog mismatch repair proteins. Nucleic Acids Res 28: 463-471, 2000). MSH2 may bind to mismatches alone or when complexed with two other conserved proteins, MSH6 or MSH3. The MSH2-MSH6 complex, referred to as MutSα, binds and participates in the repair of single base mismatches in addition to those consisting of 1-8 unpaired nucleotides (Clark, A B, Cook, M E, Tran, H T, Gordenin, D A, Resnick, M A, Kunkel, T A: Functional analysis of human MutSalpha and MutSbeta complexes in yeast. Nucleic Acids Res. 27: 736-742, 1999). The MSH2-MSH3 complex, referred to as MutSβ, participates mainly in repair of mismatches consisting of 1-8 unpaired nucleotides.

Disruption of MMR activities can lead to increases in mutation frequency by greater than 14000-fold (Clark, A B, Cook, M E, Tran, H T, Gordenin, D A, Resnick, M A, Kunkel, T A: Functional analysis of human MutSalpha and MutSbeta complexes in yeast. Nucleic Acids Res. 27: 736-742, 1999). Thus monitoring of mutation frequency can be used as the basis of a genetic assay to evaluate the effect of expressing prokaryotic MMR proteins on the function of endogenous MMR processes in a eukaryotic cell, To illustrate the effect of prokaryotic MMR proteins on eukaryotic MMR processes, *S. cerevisiae* was employed as a model system representative of eukaryotic organisms. Use of *S. cerevisiae* as a model eukaryotic cell is appropriate for the evaluation of MMR processes due to the high degree of conservation of MMR proteins and activities from yeast to humans and plants (Harfe, B D, Jinks-Robertson, S: Annu. Rev. Genet. 34: 359, 2000; Marra, G, Schar, P: Biochem. J. 338: 1-13, 1999; Eisen, J A: Nucleic Acids Res. 26: 4291-4300, 1998; Culligan, K M, et al. Nucleic Acids Res 28: 463-471, 2000). The complex MMR system of eukaryotes was established in the eukaryotic phylogenetic lineage prior to the divergence of fungal, plant and animal ancestors (Eisen, J A, Nucleic Acids Res. 26: 4291-4300, 1998).

The function of yeast MMR processes was evaluated by monitoring mutation frequency at the lys2::InsE-A14 allele (Clark, A B, et al. Nucleic Acids Res. 27: 736-742, 1999). The yeast Lys2 gene normally encodes aminoadipate-semialdehyde dehydrogenase activity which is essential for production of lysine, an essential amino acid. The lys2::InsE-A14 allele has a frame-shift mutation that inhibits expression of a functional enzyme. As a result, strains possessing this allele are auxotrophic for lysine (i.e. require the addition of lysine to the medium to grow). During DNA replication nucleotide insertions and deletions can occur within the lys2::InsE-A14 allele and escape the proof-reading activity of DNA polymerase resulting in base-pair mismatches. These base-pair insertions and deletions, if incorporated into the genome, could restore the reading frame of the lys2::InsE-A14 allele resulting in production of functional aminoadipate-semialdehyde dehydrogenase and conferral of lysine prototrophy (i.e. ability to grow in medium without supplemental lysine). Thus if the mismatches in the lys2::InsE-A14 allele are recognized and repaired by MMR machinery then the lys2::InsE-A14 allele will be returned to the wrong reading frame. This would result in maintenance of the mutant gene and lysine auxotrophy. However, if the mismatch is not recognized and repaired by MMR machinery then the reading frame of the lys2::InsEA14 allele may be changed resulting in production of a functional enzyme and conferral of lysine prototrophy.

Thus monitoring the frequency of lysine prototrophy may reflect the mutation frequency and, thereby, the function of MMR machinery. Therefore expression of a prokaryotic protein that could interfere with eukaryotic MMR processes could be expected to increase mutation frequency. This might result from the prokaryotic protein binding to, for example, genomic DNA mismatches. This, in effect, may sequester the mismatches thereby inhibiting the binding of the mismatches by the endogenous eukaryotic MMR proteins. Because of evolutionary distance between prokaryotic and eukaryotic MMR proteins (Eisen, J A, Nucleic Acids Res. 26: 4291-4300, 1998; Culligan, K M, et. al. Nucleic Acids Res 28: 463-471, 2000), the prokaryotic protein would not be able to effectively recruit and/or activate the endogenous eukaryotic MMR proteins. As a result, the MMR activity would be inhibited and the frequency of mutation at the lys2::InsE-A14 allele would be elevated. This would be reflected by elevated lysine prototrophy. In contrast, expression of prokaryotic proteins that could contribute to repairing mismatches in a eukaryotic cell might be expected to confer a decrease in mutation frequency of the lys2::InsE-A14 allele. This would be represented by a decrease in lysine prototrophy.

The strains of *S. cerevisiae* employed in this assay were E134 and DAG60 (Clark, A B, et. al. Nucleic Acids Res. 27: 736-742, 1999). The strains both encode the lys2::InsE-A14 allele and are isogenic except for the msh2-deletion allele possessed by DAG60. This mutation severely debilitates MMR activity resulting in greater than 14000-fold increase in mutation frequency in DAG60 vs. E134. To assess if prokaryotic MMR proteins could inhibit the function of eukaryotic MMR processes, E134 was transformed with constructs capable of expressing MutS (pTK42), NLS-MutS (pTK40), NLS-$MutS^{501}$ (pTK41), NLS-MutL (pTK61) or NLS-MutS in combination with NLS-MutL (pTK40 plus pTK61) as described above (see Example 1). E134 was also transformed with the empty parental vector (pCM190) to produce a control strain. All yeast transformations were done as per Geitz et al (Gietz, R D, Schiestl, R H, Willems, A R, Woods, R A: Studies on the transformation of intact yeast cells by the LiAc/SS-DNA/PEG procedure. Yeast 11: 355-360, 1995).

The strains were cultured in the presence of doxycycline (10 μg/ml on solid medium; 5 μg/ml in broth cultures) to repress expression of the test genes until the genetic assay was conducted. Eight to ten single colonies from each test strain were used to inoculate individual cultures of 5 ml SC-URA (for pCM190-based constructs) or SC-TRP (for YEplac112Tet7x- or YCplac22Tet2x-based constructs) or SC-URA-TRP (for combinations of constructs) in 50 ml culture tubes (Falcon). After 3 days of culture in a shaking incubator (225 RPM; 30° C.), aliquots of the cells were plated on YPD medium to determine viable cell number or on SC-LYS to identify lysine prototrophs. The data of viable cell number and lysine prototrophic cells was compiled, taking into consideration the dilution factors, and analysed by the method of the median (Lea, D, Coulson, C. The distribution of the numbers of mutants in bacterial populations. J. Genet. 49:264-285, 1948) with statistical analysis as described by Dixon and Massey (Dixon, W, Massey F: *Introduction to statistical analysis*. McGraw-Hill, Inc., New York, 1969). The lysine prototrophs represent events where a frame-shift mutation in the lys2::InsE-$A_{14}$ allele may have been stabilized by inhibition of the endogenous eukaryotic MMR processes by the expressed prokaryotic proteins. The results are presented in Table 4.

TABLE 4

Effect of expressing prokaryotic mismatch repair proteins on mutation frequency in eukaryotic cells.

| Strain[a] | Gene | Experiment | mutations/cell division[b] | Mutation Ratio[c] |
|---|---|---|---|---|
| E134/pCM 190 | n/a | 1<br>2 | $6.30 \times 10^{-7}$ | n/a |
| E134/pTK42 | MutS (w/o NLS) | 1<br>2 | $1.90 \times 10^{-5}$ | 84.8 |
| E134/pTK40 | NLS[d]-MutS | 1<br>2 | $3.83 \times 10^{-4}$ | 720.8 |
| E134/pTK41 | NLS-MutS$^{501}$ | 1<br>2 | $3.03 \times 10^{-4}$ | 545.5 |
| E134/pTK 61 | NLS-MutL | 1<br>2 | $1.09 \times 10^{-6}$ | 1.0 |
| E134/pTK 40; pTK 61 | NLS-MutS + NLS-MutL | 1<br>2 | $1.08 \times 10^{-4}$ | 121.9 |
| DAG60/pCM 190; YEp112Tet7x | n/a | 1 | $2.33 \times 10^{-2}$ | n/a |
| DAG60/pTK40 | NLS-MutS | 1 | $3.14 \times 10^{-3}$ | 0.5 |
| DAG60/pTK40; pTK61 | NLS-MutS ÷ NLS-MutL | 1 | $7.17 \times 10^{-4}$ | 0.1 |

[a]*Saccharomyces cerevisiae* strains E134 and DAG60 containing the empty vector(s) (i.e. pCM190, YEP112Tet7x) or a plasmid construct expressing the gene as indicated. E134 and DAG60 are isogenic except DAG60 encodes the null allele msh2 (Clark et al., 1999).

[b]Mutations detected in the lys2::InsE-$A_{14}$ mutant allele by scoring lysine prototrophy (Clark et al., 1999).

[c]Represents the ratio of mutants occurring in a strain expressing a particular gene versus the isogenic strain possessing the corresponding empty vector (determined using average data from the two experiments).

[d]The NLS from the SV40 T-antigen was engineered onto the N-terminus of the indicated proteins.

The data in Table 4 illustrates that prokaryotic mismatch repair proteins can function when expressed in eukaryotic cells. Expression of wild type MutS (pTK42) enhances mutation frequency by 85-fold over the control strain expressing the empty vector, and demonstrates that MutS may be inhibiting the function of endogenous MMR processes.

Without wishing to be bound by theory, a possible mode of action for this inhibition is that MutS may bind to the mismatches that occur during DNA replication, thereby inhibiting binding of the mismatches by the endogenous MSH2 protein acting alone or when complexed, for example, with MSH3 or MSH6. Thus the endogenous eukaryotic MMR proteins may not be able to facilitate repair of the mismatched bases and restore the normal genome sequence. As a result, the mutation becomes genetically stabilised and may be inherited by subsequent generations.

These results demonstrate that wild type prokaryotic MMR proteins may be used to inhibit eukaryotic MMR processes to increase the frequency of heritable mutations in genomic loci.

The data presented in Table 4 also illustrate that inhibition of endogenous eukaryotic MMR processes using prokaryotic MMR proteins may be enhanced by engineering the prokaryotic MMR proteins to encode a nuclear localization sequence. This is illustrated by the 8.5-fold increase in mutation frequency in cells expressing NLS-MutS (pTK40) versus MutS without a NLS (pTK42). The result is a greater than 700-fold increase in mutation frequency versus the control. This illustrates that MutS can be engineered to be very effective at inhibiting the function of endogenous eukaryotic MMR processes.

Without wishing to be bound by theory, the mode of action for this inhibitory effect may be the same as that for unmodified MutS described above, namely the ability of NLS-MutS to bind genomic mismatches and thereby inhibit recognition and repair of the mismatches by the endogenous MSH2 and associated proteins. However, the addition of a NLS to the prokaryotic protein will promote its localization to the nucleus, and thereby increase the frequency whereby genomic mismatches are sequestered by the prokaryotic MutS.

These results demonstrate that wild type prokaryotic MMR proteins may be used to inhibit endogenous eukaryotic MMR processes to increase the frequency of heritable mutations in genomic loci. In addition, the results illustrate that the degree of interference of endogenous eukaryotes MMR processes, and a resultant effect on mutation frequency of genomic loci, may be modulated by expressing prokaryotic MMR proteins with, or without an NLS.

The data of Table 4 further demonstrate that mutant forms of prokaryotic MMR proteins may be used to inhibit the function of endogenous eukaryotic MMR processes. This is illustrated by the greater than 500-fold increase in mutation frequency in cells expressing NLS-MutS$^{501}$ (pTK41) versus the control. MutS$^{501}$ is a mutant version of MutS that may be defective for ATP-binding and/or hydrolysis (Wu, T H, Marinus, M G: Dominant negative mutator mutations in the mutS gene of *Escherichia coli*. J. Bacteriol. 176: 5393-5400, 1994), as described above. ATP binding and/or hydrolysis may influence the affinity of MutS for mismatches and/or the stability of MutS-mismatch complexes (Joshi, A, Sen, S, Rao, B J: ATP-hydrolysis-dependent conformational switch modulates the stability of MutS-mismatch complexes. Nucleic Acids Res. 28: 853-861, 2000). This possible altered affinity and/or stability property of MutS$^{501}$ is reflected by the approximately 30% decrease in mutation frequency of NLS-MutS$^{501}$ (pTK41) versus NLS-MutS (pTK40).

These results demonstrate that mutant prokaryotic MMR proteins may be used to inhibit endogenous eukaryotic MMR processes to increase the frequency of heritable mutations in genomic loci. These results also illustrate that the degree of interference of endogenous eukaryotic MMR processes and resultant effect on mutation frequency of genomic loci may be modulated by expressing mutant or wild-type versions of MutS.

The data in Table 4 demonstrate that prokaryotic MutL does not have a significant effect on the function of endogenous eukaryotic MMR processes when expressed alone. This is reflected by the absence of a significant change in mutation frequency when NLS-MutL (pTK61) is expressed alone versus the control. However, when NLS-MutL (pTK61) is coexpressed with NLS-MutS (pTK40), the ability of NLS-MutS to inhibit the activity of endogenous eukaryotic MMR processes is suppressed. This is reflected by the approximately 6-fold decrease in mutation frequency in eukaryotic cells when NLS-MutL and NLS-MutS are coexpressed versus NLS-MutS alone. MutL may influence the affinity of MutS for mismatches and/or the stability of MutS-mismatch complexes (Schofield, M J, Nayak, S, Scott, T H, Du, C, Hsieh, P: Interaction of *Escherichia coli* MutS and MutL at a DNA mismatch. J. Biol. Chem. 276: 28291-28299, 2001).

Thus the results in Table 4 illustrate that the degree of interference of endogenous eukaryotic MMR processes and resultant effect on mutation frequency of genomic loci may be modulated by coexpressing more than one prokaryotic MMR protein. In addition to MutL and its derivatives, MutH (pTK) or NLS-MutH (pTK) may also be applied to modulate the activity of MutS and/or MutL in eukaryotic hosts.

To assess if prokaryotic MMR proteins may be able to facilitate repair of mismatches in eukaryotic genomes, the ability of prokaryotic MMR proteins to genetically complement a MMR-deficient eukaryotic host was assessed. As outlined above, the *S. cerevisiae* strain DAG60 is severely deficient for MMR due to a msh2-deletion allele. DAG60 was transformed with constructs expressing NLS-MutS (pTK40) alone or in combination with NLS-MutL (pTK61). The mutation frequency of these strains may then be compared to that of a control strain possessing the empty parental vectors of pTK40 and pTK61 to assess the ability of the prokaryotic proteins to complement the msh2 deficiency. A decrease in mutation frequency in cells expressing the prokaryotic MMR proteins suggests these proteins may facilitate repair of mismatches in a eukaryotic genome. Other prokaryotic MMR proteins that may be employed, alone or in combinations, to augment the activity of MutS, MutL and MutH expressed in eukaryotic cells include: helicases (e.g. MutU (UvrD)); 5' to 3' exonucleases (exoVII; RecJ); 3' to 5' exonucleases (exoI; exoX).

The data in Table 4 also demonstrate that prokaryotic MMR proteins may have an ability to repair mismatches in eukaryotic genomes. This is reflected by the 50% decrease in mutation frequency observed when NLS-MutS was expressed in DAG60. This potential for repair is enhanced a further 5-fold when NLS-MutL is coexpressed with NLS-MutS. The potential for repairing eukaryotic genomic mismatches may be enhanced further by coexpression of other prokaryotic MMR proteins such as MutH (pTK) or NLS-MutH (pTK). Other prokaryotic MMR proteins that may be employed, alone or in combinations, to augment the activity of MutS, MutL and MutH expressed in eukaryotic cells include: helicases (e.g. MutU (UvrD)); 5' to 3' exonucleases (exoVII; RecJ); 3' to 5' exonucleases (exoI; exoX). Thus the potential for repairing eukaryotic genomic mismatches may be enhanced by expression of prokaryotic MMR proteins.

Example 4

Effect of Prokaryotic Mismatch Repair Proteins on Homeologous Recombination Frequency in Eukaryotic Cells The results discussed above in Table 4 (Example 3) illustrate that expression of prokaryotic MMR proteins in eukaryotic cells can inhibit the function of endogenous eukaryotic MMR processes. Expression of prokaryotic MutS was shown to be particularly effective at inhibiting the function of endogenous eukaryotic MMR processes. This effect was more pronounced when MutS was engineered to encode a NLS (i.e. NLS-MutS). Therefore the potential of applying MutS and NLS-MutS to increase homeologous recombination (HeR) in eukaryotic cells was evaluated.

To illustrate the effect of prokaryotic MMR proteins on homeologous recombination (HeR) in eukaryotic cells, *S. cerevisiae* was employed as a model system representative of eukaryotic organisms. Use of *S. cerevisiae* as a model eukaryotic cell is highly justified in the evaluation of MMR-related processes due to the high degree of conservation of MMR functions from. yeast to humans and plants (Harfe, B D, Jinks-Robertson, S, Annu. Rev. Genet. 34: 359, 2000; Marra, G, Schar, P, Biochem. J. 338: 1-13, 1999; Eisen, J A, Nucleic Acids Res. 26: 4291-4300, 1998; Culligan, K M, et. al. Nucleic Acids Res 28: 463-471, 2000). A genetic assay was employed to demonstrate the effect of prokaryotic MMR proteins on homeologous recombination between non-sister chromatids during meiosis.

The assay used the diploid *S. cerevisiae* P119 strain (Ross-Macdonald, P, Roeder, G S: Mutation of a meiosis-specific MutS homolog decreases crossing over but not mismatch correction. Cell 79: 1069-1080, 1994) with genotype as follows: Mata THR4LEU2 his-4-S8 ura3-52 trp 1 CANUMata thr4 leu2 his-4-644 ura3 trp 1 can 1. P119 has a portion of chromosome #3 substituted with a portion of a chromosome from *S. carlsbergensis*. This substitution thus creates stretches of homeologous sequence between the native *S. cerevisiae* chromosome #3 and the introduced chromosomal fragment from *S. carlsbergensis*. Of particular interest is the his4 locus in P119. The HIS4 gene encodes histidinol dehydrogenase which participates in biosynthesis of histidine enabling cells to grow in the absence of this essential amino acid. However, P119 encodes heteroalleles at the his4 locus. The his-4-644 allele from *S. cerevisiae* on the Matα (e.g. maternal) chromosome has a mutation and encodes a non-functional protein. The his-4-S8 allele from *S. carlsbergensis* on the Mata (e.g. paternal) chromosome also has a mutation making its gene product non-functional. However, the mutation of the his-4-S8 allele is at a different position in the gene than the mutation in the his-4-644 allele. Because both maternal (i.e. his-4-644) and paternal (i.e. his-4-S8) alleles are ([both)] mutated, the diploid cell cannot make a functional gene product and is auxotrophic for histidine.

After meiosis, gametes and progeny that inherit only the maternal or paternal allele also cannot make a functional gene product and will remain auxotrophic. However, if a recombination event occurs whereby genetic information is exchanged between maternal and paternal chromosomes within the DNA region between the mutations carried by the two alleles, then a functional HIS4 allele can result. Progeny carrying this recombined allele resulting from exchange between homeologous sequences on non-sister chromatids may therefore encode a functional gene product (i.e. histidinol dehydrogenase) and be prototrophic. Scoring for the functional gene product may be used as a genetic assay to monitor exchange of genetic information between non-sister chromatids from homeologous sequences on maternal and paternal chromosomes by assaying for the frequency of histidine prototrophy in the products of meiosis.

Comparison of the DNA sequences of the wild-type HIS4 alleles from *S. cerevisiae* (Accession NC001135j and *S. carlsbergensis* (Accession U13062) demonstrates they are homeologous DNA sequences with 85% identity. Therefore monitoring recombination frequency between the his-4-644 and his-4-S8 heteroalleles is representative of homeologous recombination events in eukaryotic cells.

The exemplified assay system involves growth of a P119 strain expressing a prokaryotic MMR gene or combination of prokaryotic MMR genes. Principal prokaryotic genes of interest include MutS, MutL, MutH and MutU. Other prokaryotic MMR proteins that may be employed, alone or in combinations, to augment the activity of MutS, MutL and MutH expressed in eukaryotic cells include:

helicases (e.g. MutU (UvrD));

5' to 3' exonucleases (exoVII; RecJ);

3' to 5' exonucleases (exoI; exoX).

These genes may be engineered to produce cognate proteins encoding a nuclear localisation sequence to promote accumulation of the prokaryotic MMR protein(s) in the eukaryotic host nucleus. The P119 strain is induced to undergo meiosis. Progeny are assayed for viability and the ability to grow in the absence of histidine. By determining the number of histidine prototrophic and viable progeny in a given treatment, homeologous recombination frequency can be estimated (i.e. # histidine prototrophic progeny per # viable progeny). By comparing HeR frequency between different test genes, or combinations thereof, the effect of the test gene(s) being expressed on the frequency of HeR can be assessed.

To test the effect of different genes in strategies to modulate meiotic homeologous recombination frequency a gene expression system and plasmid vectors functional in *S. cerevisiae* were employed. The exemplified expression system used was based on the plasmids described by Gari et al. (Yeast 13: 837-848, 1997). Briefly, a series of *S. cerevisiae* expression vectors were created, as described above, with variation in vector copy-number per cell and variation in strength of transcription promoter. Therefore, by using different vectors combining different cell copy-number with different promoter strengths, the effect of expressing genes at different levels (up to ~5-fold) can be evaluated.

The exemplified regulatable expression system discloses strategies to affect meiotic homeologous recombination frequency by enabling the promotion of gene expression in cells preparing for and undergoing meiosis. By promoting transcription in cells specifically at this stage one suppresses the effects or artifactual results due to constitutive expression of test genes during all stages of vegetative growth leading to meiosis. For example, as described above, expression of prokaryotic MMR proteins in vegetative cells can result in elevated mutation frequency. Alternatively, a promoter could be used which is expressed during meiosis or is meiosis-specific.

In summary, the exemplified system involves cloning genes of interest into yeast expression vectors with the tetO-based promoter system (Gari, E, et. al. Yeast 13: 837-848, 1997). The cells are cultured in the presence of doxycycline to suppress expression of test genes during vegetative growth. The cells are prepared to undergo meiosis and the doxycycline is removed to enable expression of the test gene. The cells are induced to undergo meiosis and resulting progeny cells are tested for viability and frequency of prototrophy resulting from recombination between homeologous heteroalleles on non-sister chromatids. The frequency of meiotic homeologous recombination can thus be determined for each test gene enabling evaluation and comparison of strategies to modify meiotic homeologous recombination.

Expression plasmids based on pCM188, pCM189 and pCM190 have a functional URA3 gene whereas those based on YCplac22 and YEplac112 encode a functional TRP1 gene and therefore P119 cells possessing such plasmids will be able to synthesize uracil and/or tryptophan and be able to grow on medium lacking uracil and/or tryptophan. Cells were cultured in the presence of doxycycline (10 μg/ml for solid media; 5 μg/ml for liquid media) to repress expression of test genes until desired growth stages.

To assay meiotic homeologous recombination frequency, 10 single colonies from each test strain were used to first inoculate 3 ml of the appropriate minimal medium containing doxycycline (e.g. SC-TRP+DOX; doxycycline at 5 μg/ml) in a 15 ml tube (Falcon) which was then incubated at 30° C. with shaking (200 RPM) for ~1.5 d. Ten cultures were prepared for each test strain, including P119 possessing the parental expression vector without a test gene and P119 possessing the various expression plasmids containing the test genes. Cells from 1 ml of culture were pelleted by centrifugation at 9000 RPM for 2 min in a standard microcentrifuge (Brinkman) and resuspended in 1 ml of sterile-distilled water (SDW). The cells were used to inoculate 5 ml of SC-A pre-meiosis medium (per liter: 1.7 g yeast nitrogen free base (Difco), 5 g ammonium acetate (Sigma), 20 g potassium acetate (Sigma), 2 g amino acid drop out mix (Adams, A, Gottschling, D E, Kaiser, C A, Stearns, T: *Methods in Yeast Genetics*. Cold Spring Harbor Laboratory Press, 1997) in a 50 ml tube (Falcon) at a 1:50 dilution. The cultures were then incubated at 30° C. with shaking (225 RPM) for 2 days.

Aliquots of cells from each culture were then collected to assay for mitotic homeologous recombination frequency occurring during vegetative growth. Dilutions of these cells were plated on YPD medium to determine viable cell number, and plated on minimal media lacking histidine so as to estimate homeologous recombination at the test genomic locus in P119 (i.e. (SC-HIS). These plates were incubated at 30° C. for 2-4 d and then colonies were counted. The remaining cells in each culture in pre-meiosis medium were pelleted by centrifugation at 4000 RPM for 10 min at 4° C. and then resuspended in 4 ml SPM meiosis-induction medium (0.3% (w/v) potassium acetate, 0.02% (w/v) raffinose, 5 μg/ml histidine, 25 μg/ml leucine, 5 μg/ml uracil, 50 μg/ml threonine). The cells were again pelleted by centrifugation at 4000 RPM for 10 min at 4° C. and resuspended in 3.5 ml SPM meiosis-induction medium. Cultures were then incubated at 30° C. with shaking (225 RPM) for 2 d to enable cells to undergo meiosis.

Dilutions of the cells were made using SDW and cells were then plated on YPD to determine viable cell number, and on minimal media lacking histidine so as to estimate meiotic homeologous recombination at the test genomic locus in P119, as described above. Duplicate dilutions and plating of each culture were performed. Plates were incubated at 30° C. for 2-4 d and then colonies were counted.

Frequency of recombinants for each culture was determined by dividing the number of prototrophs conferred by restoration of function for the his4 test locus homeologous heteroallele by the viable cell number, taking into consideration the dilution factors. Meiotic homeologous recombination frequency for each culture was corrected when necessary for background recombinants occurring during vegetative growth by subtraction of the mitotic homeologous recombination frequency determined prior to placing the cells in SPM meiosis-induction medium. Mean values for the 10 replicates of each test strain were determined using the corrected values.

Inclusion of the values from all 10 replicates in determining the mean was evaluated by the Q-test (Dean, R B, Dixon, w: Anal. Chem. 23: 636-638, 1951) and values from individual replicates were excluded from the final mean if the statistic indicated a significant deviation from the values of other replicates. Comparison of means of meiotic homeologous recombination frequency from test genes to that from control strains was done to determine the effect of the test gene. Statistical significance of the differences between these values was confirmed by evaluation using Student's t-test (Devore, J L: *Probability and Statistics*. Duxbury Press, 1995). The results are present in Table 5.

sus pTK42. This expression difference may be expected due to the properties of the promoter and copy number of the parental vectors of pTK43 and pTK42. Elevated expression of NLS-MutS (pTK37) is also effective at increasing HeR frequency.

Considering the effectiveness of mutant MutS proteins (e.g. $MutS^{501}$) to inhibit the function of endogenous eukaryotic MMR processes in vegetative cells (e.g. pTK41, Table 4, Example 3), and considering the effectiveness of wild type MutS and NLS-MutS proteins expressed in vegetative and meiotic cells to modulate endogenous eukaryotic MMR processes, it is obvious that mutant versions of prokaryotic MMR proteins may

TABLE 5

Effect of expressing prokaryotic mismatch repair proteins on meiotic homeologous recombination frequency in eukaryotic cells

| Gene | Experiment | Plasmid Construct | Vector | Promoter[c] | Copy Number[c] | Prototroph Frequency[b] | Ratio of HeR[d] | Mean Ratio of HeR |
|---|---|---|---|---|---|---|---|---|
| NLS-MutS[a] | 1 | control | Yep112Tet7x | Strong | High | $4.62 \times 10^{-5}$ | 2.04 | 1.74 |
| | | pTK37 | Yep112Tet7x | Strong | High | $9.42 \times 10^{-5}$ | | |
| | 2 | control | Yep112Tet7x | Strong | High | $1.88 \times 10^{-5}$ | 1.43 | |
| | | pTK37 | Yep112Tet7x | Strong | High | $2.69 \times 10^{-5}$ | | |
| NLS-MutS[a] | 1 | control | YCp22Tet2x | Weak | low | $2.32 \times 10^{-5}$ | 3.88 | 3.88 |
| | | pTK43 | YCp22Tet2x | Weak | low | $8.99 \times 10^{-5}$ | | |
| MutS | 1 | control | Yep112Tet7x | Strong | High | $1.88 \times 10^{-5}$ | 3.15 | 3.15 |
| | | pTK42 | Yep112Tet7x | Strong | High | $5.92 \times 10^{-5}$ | | |

[a]EcMutS encoding the nuclear localization sequence from SV40 T-antigen at the N-terminus.

[b]Homeologous recombination frequency detected by histidine prototrophy resulting from recombination between his4-S8 of *S. carlsbergensis* and his4-644 of *S. cerevisiae* in P119 (Ross-Macdonald and Roeder, 1994).

[c]The combination of vector copy number and promoter strength allows target gene expression to be varied ~5-fold (Gari et al., 1997).

[d]Homeologous recombination ratio represents the frequency of histidine prototrophic spores in P119 expressing the test gene divided by the frequency in P119 possessing the empty expression vector. Each value represents the average of ten replicates with duplicated dilutions.

The data in Table 4 demonstrate that prokaryotic MMR proteins can be used to modify the frequency of recombination between homeologous sequences in the genomes of eukaryotic cells. The results also demonstrate that the frequency of recombination between homeologous sequences present on non-sister chromatids during meiosis can be modified by expressing prokaryotic MMR proteins during meiosis.

In particular, expression of prokaryotic MutS is very effective at increasing HeR frequency during meiosis in eukaryotic cells. Without wishing to be bound by theory, one possible mode of action, as suggested by the inhibitory effect of MutS on the function of endogenous eukaryotic MMR processes in vegetative cells as described above (Table 4, Example 3), is that MutS may also inhibit the function of endogenous MMR processes during meiosis. MutS may bind to mismatches in heteroduplex DNA formed by exchange events involving homeologous sequences. This, in effect, may sequester the mismatch and inhibit recruitment and/or activation of the endogenous eukaryotic MMR processes. Thus formation of a functional cross-over between homeologous sequences may be promoted.

The results in Table 5 demonstrate that expression of wild type MutS (pTK42) is effective at enhancing HeR frequency by greater than 3-fold over natural levels in the eukaryotic model. The effectiveness of MutS at increasing HeR frequency may be enhanced by engineering the protein to encode a NLS. This is reflected by the approximately 25% increase in HeR frequency observed with NLS-MutS (pTK43) versus that of unmodified MutS (pTK42), despite the potential 5-fold lower level of expression by pTK43 ver-

Example 5

Increasing Homeologous Recombination in a *Bracsica* sp.

The method of the present invention is employed to increase homeologous recombination in *B. napus*, or other amphidiploid plants formed from interspecies hybridization between crucifer species and the progenitor species of *B. napus, B. oleracea* and *B. rapa.*

In this example, which is not to be considered limiting in any manner, *B. napus* DH120-75 is transformed with a nucleotide sequence capable of expressing NLS-MutS protein. The transgenic plant is used as one parent (the recipient parent) in an interspecies cross with a donor parent, in this case a resynthesized *B. napus*. The donor parent is preferably from a species related to the recipient parent species. The donor plant carries one or more than one gene encoding one or more than one trait of interest, provided that the donor plant is characterized as having distinct alleles when compared to the recipient plant.

The interspecies hybrid formed from this interspecies cross may then be subjected to chromosome doubling using a compound such as colchicine to produce an amphidiploid hybrid with two copies of each chromosome from each parent; a very much higher proportion of the gametes of the amphidiploid may be viable compared to the gametes of the amphihaploid. Because of the dominant effect of the disruption to the machinery responsible for mismatch repair, the frequency of homeologous recombination in the amphidiploid interspecies hybrid is elevated. This elevated frequency of homeologous recombination improves the probability of a homeologous recombination event occurring in close proximity to the desirable donor gene of interest encoding the trait of interest.

As a result of this cross, a hybrid chromosome, with a segment of chromosome from the recipient crop species closely adjacent to the locus from the homeologous donor chromosome that carries the gene controlling the trait of interest, is obtained. Hybrid chromosomes with the desired genetic composition are identified in the next generation by mapping genetic markers closely linked to the gene encoding the trait of interest and markers to loci in the homeologous region within the genome of the donor species.

The hybrid chromosome allows introduction into a crop plant of a gene controlling a desirable trait without the associated introduction of alleles at linked loci that cause undesirable problems with agronomic performance or quality characteristics.

The present invention has been described with regard to preferred embodiments. However, it will be obvious to persons skilled in the art that a number of variations and modifications can be made without departing from the scope of the invention as described herein. In the specification the word "comprising" is used as an open-ended term, substantially equivalent to the phrase "including but not limited to", and the word "comprises" has a corresponding meaning. Citation of references is not an admission that such references are prior art to the present invention.

All references are herein incorporated by reference.

1. Clark, A B, Cook, M E, Tran, H T, Gordenin, D A, Resnick, M A, Kunkel, T A: Functional analysis of human MutSalpha and MutSbeta complexes in yeast. Nucleic Acids Res. 27: 736-742 (1999).
2. Gari, E, Piedrafita, L, Aldea, M, Herrero, E: A set of vectors with a tetracycline-regulatable promoter system for modulated gene expression in *Saccharomyces cerevisiae*. Yeast 13: 837-848 (1997).
3. Lea, D, Coulson, C. The distribution of the numbers of mutants in bacterial populations. J. Genet. 49, pp. 264-285. 1948.
4. Marsischky, G T, Filosi, N, Kane, M F, Kolodner, R: Redundancy of *Saccharomyces cerevisiae* MSH3 and MSH6 in MSH2-dependent mismatch repair. Genes Dev. 10: 407-420 (1996).
5. Ross-Macdonald, P, Roeder, G S: Mutation of a meiosis-specific MutS homolog decreases crossing over but not mismatch correction. Cell 79: 1069-1080 (1994).
6. Wu, T H, Marinus, M G: Dominant negative mutator mutations in the mutS gene of *Escherichia coli*. J. Bacteriol. 176: 5393-5400 (1994).
7. Datta A, Hendrix M, Lipsitch M, Jinks-Robertson S. Dual roles for DNA sequence identity and the mismatch repair system in the regulation of mitotic crossing-over in yeast. Proc Natl Acad Sci USA. 1997 94(18):9757-62.
8. Kobayashi et al., 1994. DNA Res. 1:15-26.
9. Chu et al., 1998. Science 282:699-705.
10. Klimyuk et al., 1997. Plant J. 11:1-14.
11. Guyer et al., 1998. Genetics 149:633-639.
12. Moore et al., 1998. Proc. Natl. Acad. Sci. U.S.A. 95: 376-381.
13. Labow et al., 1990. Mol. Cell. Biol. 10: 3343-3356.
14. Ainley et al., 1990. Plant Mol. Biol. 14:949-967.
15. Martinez et al., 1999. Plant J. 19: 97-106.
16. Bohner et al., 1999. Plant J. 19:87-95.
17. Gatz et al., 1991. Mol. Gen. Genet. 227:229-237.
18. Weinmann et al., 1994. Plant J. 5: 559-569.
19. Mett et al., 1996 Transgenic Res. 5:105-113.
20. Mett et al., 1993. PNAS 90:4567-4571.

The embodiments of the invention in which an exclusive property of privilege is claimed are defined as follows:

1. A method of increasing recombination between two plants comprising the steps of:

a) providing a first plant with a nucleotide sequence capable of expressing a wild-type prokaryotic MutS, or a mutant form of MutS consisting of a defect in the ATP-binding site, wherein the mutant form of MutS is capable of binding to nucleotide mismatch regions in DNA, within a germ cell undergoing meiosis, b) mating the first plant with a second plant to produce a first progeny with increased recombination, c) mating the first progeny to produce a next generation comprising a hybrid chromosome, and d) identifying the hybrid chromosome in the next generation.

2. The method of claim 1, wherein the first plant and the second plant may be crossed, and are selected from the group consisting of *Brassica, Sinapis, Triticum, Zea, Hordeum, Triticum, Avena, Oryza, Glycine, Linum, Medicago, Lens, Pisum, Cicer, Solanum, Lycopersicon, Secale, Populus, Gossypium, Raphanus, Moricandia, Crambe, Triflorium, Phaseolus, Bromus, Phleum, Agropyron, Helianthus, Beta, Malus, Prunus, Cucurbita, Phoenix, Abies, Acer, Quercus, Olea, Allium, Washingtonia, Papaver, Rosa, Carthamus, Vicia, Fragaria, Lotus, Onobrychis, Trigonelia, Vigna, Citrus, Geranium, Daucus, Arabidopsis, Atropa, Capsicum, Picea, Pyrus, Pinus, Hyoscyamus, Nicotiana, Arachus, Asparagus, Heterocatlis, Nemesia, Pelargonium, Panicum, Penniserum, Ranunculus, Senecio, Salpiglossis, Cucarnis, Browallia, Cedrus, Lolium, Sorghum, Datura, Petunia, Digitalis, Majorana, Cichorium, Lactuca, Antirrhinum, Teosinte* and *Manihot*.

3. The method of claim 2, wherein the first plant and the second plant are selected from the group consisting of *Brassica, Sinapis, Raphanus, Moricandia* and *Crambe*.

4. The method of claim 2, wherein the first plant and the second plant are selected from the group consisting of *Triticum, Hordeum, Avena* and *Oryza*.

5. The method of claim 1, wherein the wild-type prokaryotic MutS is *E. coli* MutS protein, or the mutant form of MutS is *E. coli* $MutS^{501}$ protein.

6. The method of claim 5, wherein the MutS further comprises a nuclear localization signal.

7. The method of claim 1, wherein the nucleotide sequence further comprises one or more regulatory regions for controlling transcription or translation of the wild-type prokaryotic MutS gene, or the mutant form of MutS gene.

8. The method of claim 7, wherein the one or more regulatory regions comprises a constitutive promoter, a meiotic promoter, an S-phase promoter, a pre-meiotic S-phase promoter, a G2-phase promoter, or a preferentially meiotic promoter.

9. The method of claim 1, further comprising the step of expressing one or more additional factors that promote homologous recombination.

10. The method of claim 9, wherein the one or more additional factors are selected from the group consisting of factors that promote double strand breaks in DNA, factors involved in resection of nucleotide strands, factors involved in strand invasion, factors involved in resolution of crossover, factors involved in helicase activity, or chromatin remodeling proteins.

11. The method of claim 10, wherein the factors are selected from the group consisting of SPO11, MRE11, RAD50, XRS2/NBS1, RecA homologues, RAD 52, RAD54, TID1, MSH4, MSH5, BLM, WRN, SGS1, MCM2-7, histone acetylases, synaptonemal complex proteins and any combination thereof.

12. The method of claim 1, wherein the nucleotide sequence further comprises one or more regulatory regions for controlling transcription or translation of the wild-type prokaryotic MutS gene, or the mutant form of MutS gene.

13. The method of claim 1, wherein the method results in an increase in interspecies or intraspecies homeologous recombination.

14. The method of claim 1 wherein the increase in recombination enables achieving a desired combination of alleles in a smaller number of gametes and fewer progeny and a lower number of lineal generations than that occurring when relying on naturally occurring levels of recombination.

15. The method of claim 1 wherein, following the step (b) of mating, the first progeny having increased recombination potential are identified.

* * * * *